(12) United States Patent
Wang et al.

(10) Patent No.: US 7,964,560 B2
(45) Date of Patent: Jun. 21, 2011

(54) HEPATITIS C VIRUS INHIBITORS

(75) Inventors: Alan Xiangdong Wang, Guilford, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 149 days.

(21) Appl. No.: 12/473,188

(22) Filed: May 27, 2009

(65) Prior Publication Data

US 2009/0304626 A1    Dec. 10, 2009

Related U.S. Application Data

(60) Provisional application No. 61/056,875, filed on May 29, 2008.

(51) Int. Cl.
A61K 38/55    (2006.01)
(52) U.S. Cl. .................................................. 514/4.1
(58) Field of Classification Search .................. None
See application file for complete search history.

(56) References Cited

U.S. PATENT DOCUMENTS

| | | | |
|---|---|---|---|
| 5,223,432 A | 6/1993 | Wirz et al. | |
| 7,449,479 B2 * | 11/2008 | Wang et al. | 514/313 |
| 7,582,605 B2 * | 9/2009 | Moore et al. | 514/1.1 |
| 7,601,709 B2 * | 10/2009 | Miao et al. | 514/183 |
| 2005/0209135 A1 | 9/2005 | Busacca et al. | |
| 2006/0199773 A1 | 9/2006 | Sausker et al. | |
| 2006/0257980 A1 | 11/2006 | Li | |
| 2007/0078081 A1 | 4/2007 | Casarez et al. | |
| 2008/0032936 A1 | 2/2008 | Gai et al. | |
| 2008/0039470 A1 | 2/2008 | Niu et al. | |
| 2008/0181868 A1 | 7/2008 | Sun et al. | |
| 2008/0279821 A1 | 11/2008 | Niu et al. | |
| 2009/0202476 A1 | 8/2009 | Perrone et al. | |

FOREIGN PATENT DOCUMENTS

| | | |
|---|---|---|
| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |

(Continued)

OTHER PUBLICATIONS

U.S. Appl. No. 12/202,603, filed Sep. 2, 2008, Wang et al.
U.S. Appl. No. 12/418,677, filed Apr. 6, 2009, Sin et al.
U.S. Appl. No. 12/464,954, filed May 13, 2009, Sun et al.
U.S. Appl. No. 12/465,142, filed May 13, 2009, Sin et al.
U.S. Appl. No. 12/476,741, filed May 28, 2009, Wang et al.
Lauer, G.M. et al., "Hepatitis C Virus Infection", The New England Journal of Medicine, vol. 345, No. 1, pp. 41-52 (2001).
Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).
Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

(Continued)

*Primary Examiner* — Cecilia Tsang
*Assistant Examiner* — Thomas S Heard
(74) *Attorney, Agent, or Firm* — Pamela A. Mingo

(57) ABSTRACT

Hepatitis C virus inhibitors having the general formula

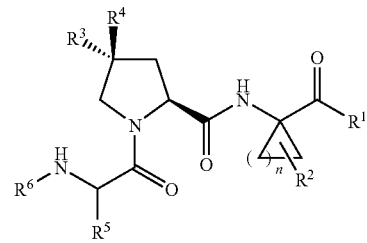

are disclosed. Compositions comprising the compounds and methods for using the compounds to inhibit HCV are also disclosed.

18 Claims, No Drawings

FOREIGN PATENT DOCUMENTS

| | | |
|---|---|---|
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005690 | 1/2009 |
| WO | WO 2009/010804 | 1/2009 |
| WO | WO 2009/014730 | 1/2009 |
| WO | WO 2009/082701 | 7/2009 |
| WO | WO 2009/085659 | 7/2009 |

OTHER PUBLICATIONS

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. at al., "Enzymatic preparation of homochiral 2-isobutyl succinic acid derivatives", Tetrahedron: Asymmetry, vol. 8, No. 2, pp. 187-189 (1997).

Yang, S., "Chemoenzymatic Synthesis of (R)-(—)-Citramalic Acid", Synthesis, pp. 365-366 (1992).

\* cited by examiner

HEPATITIS C VIRUS INHIBITORS

CROSS-REFERENCE TO RELATED APPLICATIONS

This application claims the benefit of U.S. Provisional Application Ser. No. 61/056,875 filed May 29, 2008.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with one or two additional compounds having anti-HCV activity.

In its first aspect the present disclosure provides a compound of Formula (I)

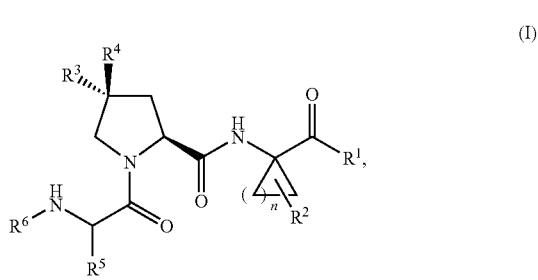

(I)

or a pharmaceutically acceptable salt thereof, wherein
n is 1, 2, or 3;
$R^1$ is selected from hydroxy and —NHSO$_2$R$^7$;
$R^2$ is selected from hydrogen, alkenyl, alkyl, and cycloalkyl; wherein the alkenyl, the alkyl, and the cycloalkyl are optionally substituted with one, two, three, or four halo groups;
$R^3$ is selected from alkenyl, alkyl, aryl, arylalkyl, cycloalkyl, (cycloalkyl)alkyl, heterocyclyl, and heterocyclylalkyl;
$R^4$ is selected from —S—R$^8$, —S(O)—R$^8$, and —S(O)$_2$—R$^8$;
$R^5$ is selected from hydrogen, alkenyl, alkoxyalkyl, alkoxycarbonylalkyl, alkyl, arylalkyl, carboxyalkyl, cyanoalkyl, cycloalkyl, (cycloalkyl)alkyl, haloalkoxyalkyl, haloalkyl, hydroxyalkyl, (NR$^a$R$^b$)alkyl, and (NR$^a$R$^b$)carbonylalkyl;
$R^6$ is selected from hydrogen, alkoxycarbonyl, alkyl, alkylcarbonyl, alkylsulfonyl, cycloalkyloxycarbonyl, cycloalkyl, haloalkoxycarbonyl, haloalkyl, haloalkylcarbonyl, (NR$^a$R$^b$)carbonyl, and (NR$^a$R$^b$)sulfonyl; or
$R^6$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substituents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —NR$^g$R$^h$, (NR$^j$R$^k$)carbonyl, (NR$^j$R$^k$)sulfonyl, and oxo;
$R^7$ is selected from alkyl, aryl, cycloalkyl, (cycloalkyl)alkyl, heterocyclyl, and —NR$^c$R$^d$; wherein the cycloalkyl is optionally substituted with one group selected from alkyl, halo, and haloalkyl;
$R^8$ is selected from alkoxyalkyl, alkyl, arylalkyl, cycloalkyl, (cycloalkyl)alkyl, haloalkoxyalkyl, and haloalkyl;
$R^a$ and $R^b$ are independently selected from hydrogen, alkoxy, alkoxyalkyl, alkyl, aryl, arylalkyl, cycloalkyl, haloalkoxyalkyl, haloalkyl, heterocyclyl, and heterocyclylalkyl;

$R^c$ and $R^d$ are independently selected from alkoxy, alkyl, aryl, arylalkyl, cycloalkyl, (cycloalkyl)alkyl, heterocyclyl, and heterocyclylalkyl; or $R^c$ and $R^d$ together with the nitrogen atom to which they are attached form a five or six-membered monocyclic heterocyclic ring;

$R^g$ and $R^h$ are independently selected from hydrogen, alkoxyalkyl, alkoxycarbonyl, alkyl, alkylcarbonyl, arylalkyl, and haloalkyl; and $R^j$ and $R^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

In a first aspect of the first embodiment the present disclosure provides a compound of Formula (I), or a pharmaceutically acceptable salt thereof, wherein $R^1$ is —$NHSO_2R^7$.

In a second aspect of the first embodiment the present disclosure provides a compound of Formula (I), or a pharmaceutically acceptable salt thereof; wherein n is 1;

$R^2$ is selected from alkenyl, alkyl, and cycloalkyl; wherein the alkenyl, the alkyl, and the cycloalkyl are optionally substituted with one, two, three, or four halo groups;

$R^3$ is selected from alkenyl, alkyl, aryl, arylalkyl, cycloalkyl, (cycloalkyl)alkyl, heterocyclyl, and heterocyclylalkyl;

$R^4$ is selected from —S—$R^8$, —S(O)—$R^8$, and —$S(O)_2$—$R^8$;

$R^5$ is selected from alkenyl, alkyl, and arylalkyl;

$R^6$ is selected from alkoxycarbonyl, cycloalkyloxycarbonyl, haloalkoxycarbonyl, ($NR^aR^b$)carbonyl;

$R^7$ is unsubstituted cycloalkyl; and $R^8$ is alkyl.

In a third aspect of the first embodiment the present disclosure provides a compound of Formula (I), or a pharmaceutically acceptable salt thereof, wherein $R^1$ is —$NHSO_2R^7$;

n is 1;

$R^2$ is selected from alkenyl, alkyl, cycloalkyl, and haloalkyl;

$R^3$ is selected from alkenyl, alkyl, aryl, arylalkyl, cycloalkyl, (cycloalkyl)alkyl, heterocyclyl, and heterocyclylalkyl;

$R^4$ is selected from —S—$R^8$, —S(O)—$R^8$, and —$S(O)_2$—$R^8$;

$R^5$ is alkyl;

$R^6$ is selected from alkoxycarbonyl, cycloalkyloxycarbonyl, haloalkoxycarbonyl, ($NR^aR^b$)carbonyl;

$R^7$ is cycloalkyl; and $R^8$ is alkyl.

In a fourth aspect of the first embodiment the present disclosure provides a compound of Formula (I), or a pharmaceutically acceptable salt thereof, wherein $R^1$ is —$NHSO_2R^7$;

n is 1;

$R^2$ is selected from alkenyl, alkyl, cycloalkyl, and haloalkyl;

$R^3$ is aryl;

$R^4$ is selected from —S—$R^8$, —S(O)—$R^8$, and —$S(O)_2$—$R^8$;

$R^5$ is alkyl;

$R^6$ is selected from alkoxycarbonyl, cycloalkyloxycarbonyl, haloalkoxycarbonyl, ($NR^aR^b$)carbonyl;

$R^7$ is cycloalkyl; and $R^8$ is alkyl

In a second aspect the present disclosure provides a composition comprising the compound of formula (I), or a pharmaceutically acceptable salt thereof, and a pharmaceutically acceptable carrier. In a first embodiment of the second aspect the composition further comprises at least one additional compound having anti-HCV activity. In a second embodiment of the second aspect at least one of the additional compounds is an interferon or a ribavirin. In a third embodiment of the second aspect the interferon is selected from interferon alpha 2B, pegylated interferon alpha, consensus interferon, interferon alpha 2A, and lymphoblastoid interferon tau.

In a fourth embodiment of the second aspect the present disclosure provides a composition comprising the compound of formula (I), or a pharmaceutically acceptable salt thereof a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the second aspect the present disclosure provides a composition comprising the compound of formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of formula (I), or a pharmaceutically acceptable salt thereof. In a first embodiment of the third aspect the method further comprises administering at least one additional compound having anti-HCV activity prior to, after, or simultaneously with the compound of formula (I), or a pharmaceutically acceptable salt thereof. In a second embodiment of the third aspect at least one of the additional compounds is an interferon or a ribavirin. In a third embodiment of the third aspect the interferon is selected from interferon alpha 2B, pegylated interferon alpha, consensus interferon, interferon alpha 2A, and lymphoblastoid interferon tau.

In a fourth embodiment of the third aspect the present disclosure provides a method of treating an HCV infection in a patient, comprising administering to the patient a therapeutically effective amount of a compound of formula (I), or a pharmaceutically acceptable salt thereof and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the third aspect the present disclosure provides a method of treating an HCV infection in a patient, comprising administering to the patient a therapeutically effective amount of a compound of formula (I), or a pharmaceutically acceptable salt thereof and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a composition comprising a compound of formula (I), or a pharmaceutically acceptable salt thereof, one, two, three, four, or five additional compounds having anti-HCV activity, and a pharmaceutically acceptable carrier. In a first embodiment of the fourth aspect the composition comprises three or four additional compounds having anti-HCV activity. In a second embodiment of the fourth aspect the composition comprises one or two additional compounds having anti-HCV activity.

In a fifth aspect the present disclosure provides a method of treating an HCV infection in a patient, comprising administering to the patient a therapeutically effective amount of a compound of formula (I), or a pharmaceutically acceptable salt thereof and one, two, three, four, or five additional compounds having anti-HCV activity prior to, after, or simultaneously with the compound of formula (I), or a pharmaceutically acceptable salt thereof. In a first embodiment of the fifth aspect the method comprises administering three or four additional compounds having anti-HCV activity. In a second embodiment of the fifth aspect the method comprises administering one or two additional compounds having anti-HCV activity.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure can be optionally substituted with one, two, three, four, or five substituents independently selected from alkoxy, alkoxycarbonyl, alkyl, a second aryl group, cyano, halo, haloalkoxy, haloalkyl, heterocyclyl, heterocyclylalkyl, hydroxy, hydroxyalkyl, nitro, —$NR^xR^y$, ($NR^xR^y$)alkoxy, ($NR^xR^y$)alkyl, $NR^xR^y$)carbonyl, and oxo; wherein the second aryl group, the heterocyclyl, and the heterocyclyl part of the heterocyclylalkyl can be further optionally substituted with one, two, three, four, or five substituents independently selected from alkoxy, alkyl, cyano, halo, haloalkoxy, haloalkyl, hydroxy, and nitro.

The term "arylalkyl," as used herein, refers to an alkyl group substituted with one, two, or three aryl groups.

The term "carbonyl," as used herein, refers to —C(O)—.

The term "carboxy," as used herein, refers to —$CO_2H$.

The term "carboxyalkyl," as used herein, refers to an alkyl group substituted with one, two, or three carboxy groups.

The term "cyano," as used herein, refers to —CN.

The term "cyanoalkyl," as used herein, refers to an alkyl group substituted with one, two, or three cyano groups.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3.1.1]heptyl, and adamantyl. The cycloalkyl groups of the present disclosure can be optionally substituted with one, two, three, or four substituents independently selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and ($NR^jR^k$)carbonyl; wherein $R^j$ and $R^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

The term "(cycloalkyl)alkyl," as used herein, refers to an alkyl group substituted with one, two, or three cycloalkyl groups.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxyalkyl," as used herein, refers to an alkyl group substituted with one, two, or three haloalkoxy groups.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylcarbonyl," as used herein, refers to a haloalkyl group attached to the parent molecular moiety through a carbonyl group.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four- to six-membered aromatic or non-aromatic carbocyclic ring or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocyclyl groups of the present disclosure can be optionally substituted with one, two, three, four, or five substituents independently selected from alkoxy, alkoxycarbonyl, alkyl, aryl, cyano, halo, haloalkoxy, haloalkyl, a second heterocyclyl group, heterocyclylalkyl, hydroxy, hydroxyalkyl, nitro, —$NR^xR^y$, ($NR^xR^y$)alkoxy, ($NR^xR^y$)alkyl, ($NR^xR^y$)carbonyl, and oxo; wherein the aryl, the second heterocyclyl group, and the heterocyclyl part of the heterocyclylalkyl can be further optionally substituted with one, two, three, four, or five substituents independently selected from alkoxy, alkyl, cyano, halo, haloalkoxy, haloalkyl, hydroxy, and nitro.

The term "heterocyclylalkyl," as used herein, refers to an alkyl group substituted with one, two, or three heterocyclyl groups.

The term "hydroxy," as used herein, refers to —OH.

The term "hydroxyalkyl," as used herein, refers to an alkyl group substituted with one, two, or three hydroxy groups.

The term "—$NR^aR^b$," as used herein, refers to two groups, $R^a$ and $R^b$, which are attached to the parent molecular moiety through a nitrogen atom. $R^a$ and $R^b$ are each independently selected from hydrogen, alkoxy, alkoxyalkyl, alkyl, aryl, arylalkyl, cycloalkyl, haloalkoxyalkyl, haloalkyl, heterocyclyl, and heterocyclylalkyl.

The term "($NR^aR^b$)alkyl," as used herein, refers to an alkyl group substituted with one, two, or three —$NR^aR^b$ groups.

The term "($NR^aR^b$)carbonyl," as used herein, refers to an —$NR^aR^b$ group attached to the parent molecular moiety through a carbonyl group.

The term "($NR^aR^b$)carbonylalkyl," as used herein, refers to an alkyl group substituted with one, two, or three ($NR^aR^b$)carbonyl groups.

The term "($NR^aR^b$)sulfonyl," as used herein, refers to an —$NR^aR^b$ group attached to the parent molecular moiety through a sulfonyl group.

The term "—$NR^cR^d$," as used herein, refers to two groups, $R^c$ and $R^d$, which are attached to the parent molecular moiety through a nitrogen atom. $R^c$ and $R^d$ are independently selected from alkoxy, alkyl, aryl, arylalkyl, cycloalkyl, (cycloalkyl)alkyl, heterocyclyl, and heterocyclylalkyl; or $R^c$ and $R^d$ together with the nitrogen atom to which they are attached form a five or six-membered monocyclic heterocyclic ring.

The term "—$NR^eR^f$," as used herein, refers to two groups, $R^e$ and $R^f$, which are attached to the parent molecular moiety through a nitrogen atom. $R^e$ and $R^f$ are independently selected from hydrogen, alkyl, and arylalkyl; or $R^e$ and $R^f$, together with the nitrogen atom to which they are attached, form a five or six-membered monocyclic heterocyclic ring optionally containing one additional heteroatom selected from O, $NR^x$, and S; wherein $R^x$ is selected from hydrogen and alkyl; and wherein R' is selected from hydrogen and alkyl.

The term "—$NR^gR^h$," as used herein, refers to two groups, $R^g$ and $R^h$, which are attached to the parent molecular moiety through a nitrogen atom. $R^g$ and $R^h$ are independently selected from hydrogen, alkoxyalkyl, alkoxycarbonyl, alkyl, alkylcarbonyl, arylalkyl, and haloalkyl.

The term "—$NR^jR^k$," as used herein, refers to two groups, $R^j$ and $R^k$, which are attached to the parent molecular moiety through a nitrogen atom. $R^j$ and $R^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

The term "($NR^jR^k$)carbonyl," as used herein, refers to an $NR^jR^k$ group attached to the parent molecular moiety through a carbonyl group.

The term "($NR^jR^k$)sulfonyl," as used herein, refers to an —$NR^eR^f$ group attached to the parent molecular moiety through a sulfonyl group.

The term "—$NR^xR^y$," as used herein, refers to two groups, $R^x$ and $R^y$, which are attached to the parent molecular moiety through a nitrogen atom. $R^x$ and $R^y$ are independently selected from hydrogen and alkyl.

The term "($NR^xR^y$)alkoxy," as used herein, refers to an ($NR^xR^y$)alkyl group attached to the parent molecular moiety through an oxygen atom.

The term "($R^xR^y$)alkyl," as used herein, refers to an alkyl group substituted with one, two, or three —$NR^xR^y$ groups.

The term ($NR^xR^y$)carbonyl," as used herein, refers to an $NR^xR^y$ group attached to the parent molecular moiety through a carbonyl group.

The term "nitro," as used herein, refers to —$NO_2$.

The term "oxo," as used herein, refers to =O.

The term "sulfonyl," as used herein, refers to —$SO_2$—.

The compounds of the present disclosure can exist as prodrugs. The term "prodrug," as used herein, represents compounds which are rapidly transformed in vivo to the parent compounds by hydrolysis in blood. Prodrugs of the present disclosure include esters of hydroxy groups on the parent molecule, esters of carboxy groups on the parent molecule, and amides of amines on the parent molecule.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in *Remington's Pharmaceutical Sciences*, 18th ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e., N-terminus first position); whereas P1 starts the numbering from the left hand side of the C-terminus cleavage site, P2: second position from the C-terminus, etc.). (see Berger, A. et al., *Transactions of the Royal Society London series*, B257:249-264 (1970)].

The following figure shows the designations for the compounds of the present disclosure.

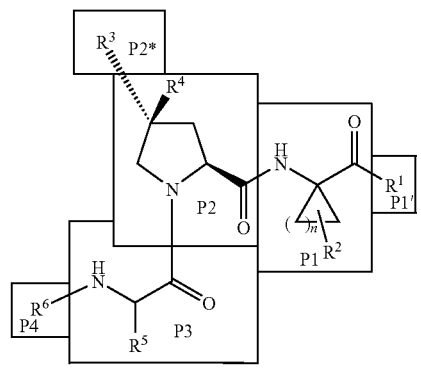

Asymmetric centers exist in the compounds of the present disclosure. For example, the compounds may include P1 cyclopropyl element of formula

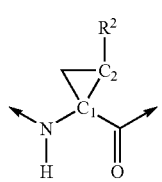

P1 wherein $C_1$ and $C_2$ each represent an asymmetric carbon atom at positions 1 and 2 of the cyclopropyl ring.

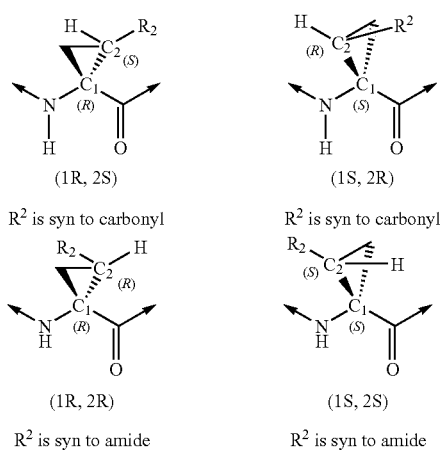

(1R, 2S)
R² is syn to carbonyl (1S, 2R)
R² is syn to carbonyl (1R, 2R)
R² is syn to amide (1S, 2S)
R² is syn to amide It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharm. Res.*, 3(6):318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/ Elan Pharmaceuticals Inc., New York, NY |
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO 2005/047288 26 May 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/ Eli Lilly and Co. Inc., Indianapolis, IN |
| HCV-796 | Antiviral | NS5B replicase inhibitor | Wyeth/Viropharma |
| NM-283 | Antiviral | NS5B replicase inhibitor | Idenix/Novartis |
| GL-59728 | Antiviral | NS5B replicase inhibitor | Gene Labs/Novartis |
| GL-60667 | Antiviral | NS5B replicase inhibitor | Gene Labs/Novartis |
| 2'C MeA | Antiviral | NS5B replicase inhibitor | Gilead |
| PSI 6130 | Antiviral | NS5B replicase inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering-Plough |
| Zadazim | Immune modulator | Immune modulator | SciClone Pharmaceuticals Inc., San Mateo, CA |
| Ceplene | Immunomodulator | Immune modulator | Maxim Pharmaceuticals Inc., San Diego, CA |
| CELLCEPT ® | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |

TABLE 1-continued

| Brand Name | Physiological Class | Type of Inhibitor or Target | Source Company |
|---|---|---|---|
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | Natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering-Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |
| MK-7009 | Antiviral | Serine protease inhibitor | Merck |
| PF-00868554 | Antiviral | Replicase inhibitor | Pfizer |
| ANA598 | Antiviral | Non-nucleoside NS5B polymerase inhibitor | Anadys Pharmaceuticals, Inc., San Diego, CA, USA |
| IDX375 | Antiviral | Non-nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| VCH-759 | Antiviral | NS5B polymerase inhibitor | ViroChem Pharma |
| VCH-916 | Antiviral | NS5B polymerase inhibitor | ViroChem Pharma |
| GS-9190 | Antiviral | NS5B polymerase inhibitor | Gilead |
| Peg-interferon lamda | Antiviral | Interferon | ZymoGenetics/Bristol-Myers Squibb |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: CDI for 1,1'-carbonyldiimidazole; THF for tetrahydrofuran; DBU for 1,8-diazabicyclo[5.4.0]undec-7-ene; TFA for trifluoroacetic acid; HATU for O-(7-azabenzotriazol-1-yl)-N,N,N',N'-tetramethyluronium phosphate; PyBOP for benzotriazol-1-yl-oxytris-pyrrolidino-phosphoniumhexafluorophosphate; MeI for methyl iodide; Boc or BOC for tert-butoxycarbonyl; OtBu for tert-butoxy; TBME for tert-butyl methyl ether; $Et_3N$ for triethylamine; DMSO for dimethylsulfoxide; OAc for acetate; DPPA for diphenylphosphoryl azide; Me for methyl; TBAF for tetrabutylammonium fluoride; DMAP for 4-N,N-dimethylaminopyridine; tBuLi for tert-butyllithium; LiHMDS for lithium hexamethyldisilazide; Tle for tert-butylleucine, also referred to as tert-butyl glycine; 4-BiphMgBr for 4-biphenylmagnesium bromide; DCM for dichloromethane; MeO for methoxy; EDAC or EDC for 1-(3-dimethylaminopropyl)-3-ethylcarbodiimide hydrochloride; and HOBt for 1-hydroxybenzotriazole.

The starting materials useful to synthesize the compounds of the present disclosure are known to those skilled in the art and can be readily manufactured or are commercially available.

The following methods set forth below are provided for illustrative purposes and are not intended to limit the scope of the claimed disclosure. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel ($SiO_2$) according to Still's flash chromatography technique (*J. Org. Chem.*, 43:2923 (1978)).

The intermediates described in the Examples found herein can be employed to synthesize compounds of Formula 1.

Example 1

Preparation of P1' Intermediates

1. Preparation of cyclopropylsulfonamide

Method 1:

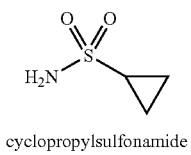

cyclopropylsulfonamide

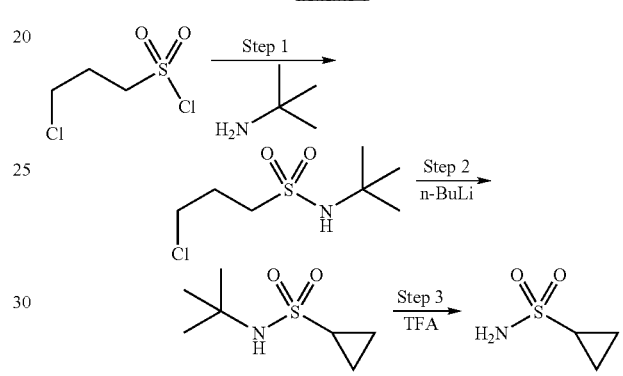

Scheme 1

Step 1 tert-Butylamine (3.0 mol, 315 μL) was dissolved in THF (2.5 L). The solution was cooled to −20° C. 3-Chloropropanesulfonyl chloride (1.5 mol, 182 mL) was added slowly. The reaction mixture was allowed to warm to room temperature and stirred for 24 hours. The mixture was filtered and the filtrate was concentrated in vacuo. The residue was dissolved in $CH_2Cl_2$ (2.0 L). The resulting solution was washed with 1.0M HCl (1.0 L), water (1.0 L), and brine (1.0 L), dried over $Na_2SO_4$, filtered, and concentrated in vacuo to give a slightly yellow solid, which was crystallized from hexane to provide the product as a white solid (316.0 g, 99%). $^1$H NMR ($CDCl_3$) δ 1.38 (s, 9H), 2.30-2.27 (m, 2H), 3.22 (t, J=7.35 Hz, 2H), 3.68 (t, J=6.2 Hz, 2H), 4.35 (b, 1H).

Step 2

To a solution of the product of Step 1 (2.14 g, 10.0 mmol) in THF (100 mL) was added n-BuLi (2.5 M in hexane, 8.0 mL, 20.0 mmol) at −78° C. The reaction mixture was allowed to warm up to room temperature over period of 1 hour and concentrated in vacuo. The residue was partitioned between ethyl acetate and water (200 mL each). The separated organic phase was washed with brine, dried over $Na_2SO_4$, filtered, and concentrated in vacuo. The residue was recrystallized from hexane to provide the desired product as a white solid (1.0 g, 56%). $^1$H NMR ($CDCl_3$) δ 0.98-1.00 (m, 2H), 1.18-1.19 (m, 2H), 1.39 (s, 9H), 2.48-2.51 (m, 1H), 4.19 (b, 1H).

Step 3

A solution of the product of Step 2 (110 g, 0.62 mmol) in TFA (500 mL) was stirred at room temperature for 16 hours.

The volatiles were removed in vacuo. The residue was recrystallized from ethyl acetate/hexane (60 mL/240 mL) to provide the desired product as a white solid (68.5 g, 91%). ¹H NMR (DMSO-d₆) δ 0.84-0.88 (m, 2H), 0.95-0.98 (m, 2H), 2.41-2.58 (m, 1H), 6.56 (b, 2H).

Method 2:

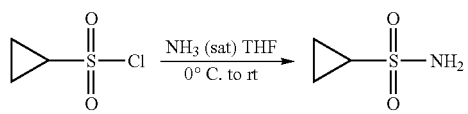

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF. The solution was warmed to room temperature overnight and stirred one additional day. The mixture was concentrated until 1-2 mL of solvent remained and poured onto a 30 g plug of SiO₂ (eluted with 30% to 60% ethyl acetate/hexanes) to provide 3.45 g (100%) of cyclopropylsulfonamide as a white solid. ¹H NMR (methanol-d₄) δ 0.94-1.07 (m, 4H), 2.52-2.60 (m, 1H); ¹³C NMR (methanol-d₄) δ 5.92, 33.01.

2. Preparation of C1-Substituted Cyclopropyl Sulfonamides

2a. Preparation of N-tert-butyl-(1-methyl)cyclopropyl-sulfonamide

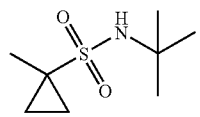

Step 1: Preparation of N-tert-butyl-(3-chloro)propylsulfonamide

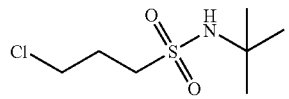

Prepared as described above.

Step 2: Preparation of N-tert-butyl-(1-methyl)cyclopropyl-sulfonamide

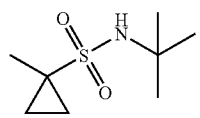

A solution of the product of Step 1 (4.3 g, 20 mmol) was dissolved in dry THF (100 mL) and cooled to −78° C. To this solution was added n-butyllithium (17.6 mL, 44 mmol, 2.5M in hexane) slowly. The dry ice bath was removed and the reaction mixture was warmed to room temperature over a period of 1.5 hours. This mixture was cooled to −78° C. and a solution of n-butyllithium (20 mmol, 8 mL, 2.5M in hexane) was added. The reaction mixture was warmed to room temperature, cooled to −78° C. over a period of 2 hours, and treated with a neat solution of methyl iodide (5.68 g, 40 mmol). The reaction mixture was warmed to room temperature overnight, then quenched with saturated NH₄Cl (100 mL) at room temperature and extracted with ethyl acetate (100 mL). The organic phase was washed with brine (100 mL), dried (MgSO₄), filtered, and concentrated in vacuo to provide a yellow oil which was crystallized from hexane to provide the desired product as a slightly yellow solid (3.1 g, 81%): ¹H NMR (CDCl₃) δ 0.79 (m, 2H), 1.36 (s, 9H), 1.52 (m, 2H), 1.62 (s, 3H), 4.10 (br s, 1H).

Step 3: Preparation of 1-methylcyclopropylsulfonamide

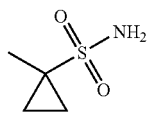

A solution of the product of Step 2 (1.91 g, 10 mmol) was dissolved in TFA (30 mL), and the reaction mixture stirred at room temperature for 16 hours. The solvent was removed in vacuo to provide a yellow oil which was crystallized from ethyl acetate/hexane (1:4, 40 mL) to provide the desired product as a white solid (1.25 g, 96%): ¹H NMR (CDCl₃) δ 0.84 (m, 2H), 1.41 (m, 2H), 1.58 (s, 3H), 4.65 (br s, 2H). Anal. Calcd. For C₄H₉NO₂S: C, 35.54; H, 6.71; N, 10.36. Found: C, 35.67; H, 6.80; N, 10.40.

2b. Preparation of 1-propylcyclopropylsulfonamide

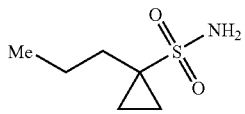

This compound was prepared using the procedure described for the preparation of 1-methylcyclopropylsulfonamide substituting propyl halide for methyl iodide in the second step of this process.

2c. Preparation of 1-allylcyclopropylsulfonamide

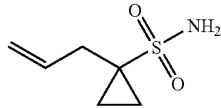

Step 1: Preparation of N-tert-butyl-(1-allyl)cyclopropylsulfonamide

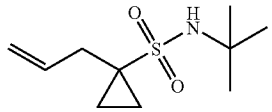

This compound was obtained in 97% yield according to the procedure described in the synthesis of N-tert-butyl-(1-methyl)cyclopropylsulfonamide using 1.25 equivalents of allyl bromide as the electrophile. The compound was used in the next reaction without further purification: $^1$H NMR (CDCl$_3$) δ 0.83 (m, 2H), 1.34 (s, 9H), 1.37 (m, 2H), 2.64 (d, J=7.3 Hz, 2H), 4.25 (br s, 1H), 5.07-5.10 (m, 2H), 6.70-6.85 (m, 1H).

Step 2: Preparation of 1-allylcyclopropylsulfonamide

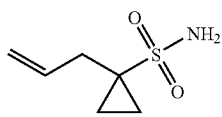

This compound was obtained in 40% yield from the product of Step 1 according to the procedure described in the synthesis of 1-methylcyclopropylsulfonamide. The compound was purified by column chromatography over SiO$_2$ using 2% methanol in dichloromethane as the eluent: $^1$H NMR (CDCl$_3$) δ 0.88 (m, 2H), 1.37 (m, 2H), 2.66 (d, J=7.0 Hz, 2H), 4.80 (s, 2H), 5.16 (m, 2H), 5.82 (m, 1H); $^{13}$C NMR (CDCl$_3$) δ 11.2, 35.6, 40.7, 119.0, 133.6.

2d. Preparation of 1-Benzylcyclopropylsulfonamide

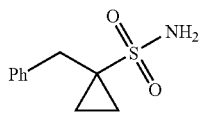

Step 1: Preparation of N-tert-butyl-(1-benzyl)cyclopropyl-sulfonamide

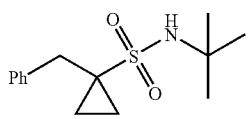

This compound was obtained in 60% yield using the procedure described for the synthesis of N-tert-butyl-(1-methyl) cyclopropylsulfonamide except 1.05 equivalents of benzyl bromide were used, followed by trituration with 10% ethyl acetate in hexane: $^1$H NMR (CDCl$_3$) δ 0.92 (m, 2H), 1.36 (m, 2H), 1.43 (s, 9H), 3.25 (s, 2H), 4.62 (br s, 1H), 7.29-7.36 (m, 5H).

Step 2: Preparation of 1-benzylcyclopropylsulfonamide

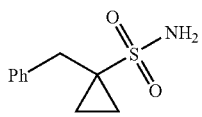

This compound was obtained in 66% yield from N-tert-butyl(1-benzyl)cyclopropylsulfonamide using the procedure described for the synthesis of 1-methylcyclopropylsulfonamide, followed by recrystallization from the minimum amount of 10% ethyl acetate in hexane: $^1$H NMR (CDCl$_3$) δ 0.90 (m, 2H), 1.42 (m, 2H), 3.25 (s, 2H), 4.05 (s, 2H), 7.29 (m, 3H), 7.34 (m, 2H); $^{13}$C NMR (CDCl$_3$) δ 11.1, 36.8, 41.9, 127.4, 128.8, 129.9, 136.5.

2e. Preparation of 1-(1-cyclohexenyl)cyclopropyl-sulfonamide

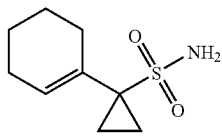

Step 1: Preparation of N-tert-butyl-[1-(1-hydroxy)cyclohexyl]-cyclopropylsulfonamide

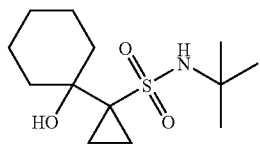

This compound was obtained in 84% yield using to the procedure described for the synthesis of N-tert-butyl-(1-methyl)cyclopropylsulfonamide except 1.30 equivalents of cyclohexanone were used, followed by recrystallization from the minimum amount of 20% ethyl acetate in hexane: $^1$H NMR (CDCl$_3$) δ 1.05 (m, 4H), 1.26 (m, 2H), 1.37 (s, 9H), 1.57-1.59 (m, 6H), 1.97 (m, 2H), 2.87 (br s, 1H), 4.55 (br s, 1H).

Step 2: Preparation of 1-(1-cyclohexenyl)cyclopropyl-sulfonamide

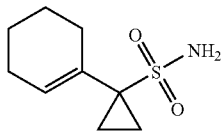

This compound, 1-(1-cyclohexenyl)-cyclopropylsulfonamide was obtained in 85% yield from N-tert-butyl-[1-(1-hydroxy)cyclohexyl]-cyclopropylsulfonamide using the procedure described for the synthesis of 1-methylcyclopropylsulfonamide, followed by recrystallization from the minimum amount of ethyl acetate and hexane: $^1$H NMR (DMSO-d$_6$) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-d$_6$) δ 11.6, 21.5, 22.3, 25.0, 27.2, 46.9, 131.6, 132.2; LR-MS (ESI): 200 (M$^+$−1).

2f. Preparation of 1-benzoylcyclo-propylsulfonamide

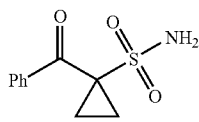

Step 1: Preparation of N-tert-butyl-(1-benzoyl)cyclopropyl-sulfonamide

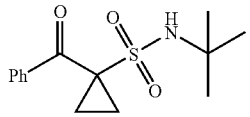

This compound was obtained in 66% yield using the procedure described for the synthesis of N-tert-butyl-(1-methyl) cyclopropylsulfonamide except 1.2 equivalents of methyl benzoate was used as the electrophile. The compound was purified by column chromatography over SiO$_2$ using 30% to 100% dichloromethane in hexane: $^1$H NMR (CDCl$_3$) δ 1.31 (s, 9H), 1.52 (m, 2H), 1.81 (m, 2H), 4.16 (br s, 1H), 7.46 (m, 2l), 7.57 (m, 1H), 8.05 (d, J=8.5 Hz, 2H).

Step 2: Preparation of 1-benzoylcyclo-propylsulfonamide

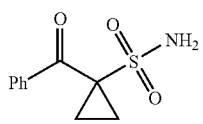

This compound was obtained in 87% yield from N-tert-butyl(1-benzoyl)cyclopropylsulfonamide using the process described for the synthesis of 1-methylcyclopropylsulfonamide, followed by recrystallization from the minimum amount of ethyl acetate in hexane: $^1$H NMR (DMSO-d$_6$) δ 1.39 (m, 2H), 1.61 (m, 2H), 7.22 (s, 2H), 7.53 (t, J=7.6 Hz, 2H), 7.65 (t, J=7.6 Hz, 1H), 8.06 (d, J=8.2 Hz, 2H); $^{13}$C NMR (DMSO-d$_6$) δ 12.3, 48.4, 128.1, 130.0, 133.4, 135.3, 192.0.

2g. Preparation of N-tert-butyl-(1-phenylaminocarboxy)-cyclopropylsulfonamide

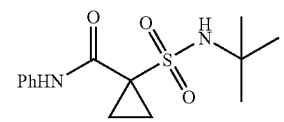

This compound was obtained in 42% yield using the procedure described for the synthesis of N-tert-butyl-(1-methyl) cyclopropylsulfonamide using 1 equivalent of phenylisocyanate, followed by recrystallization from the minimum amount of ethyl acetate in hexane $^1$H NMR (CDCl$_3$) δ 1.38 (s, 9H), 1.67-1.71 (m, 4H), 4.30 (br s, 1H), 7.10 (t, J=7.5 Hz, 1H), 7.34 (t, J=7.5 Hz, 2H), 7.53 (t, J=7.5 Hz, 2H).

3. Preparation of C1-Substituted cyclopropanesulfonamides: The use of an N-Boc protecting group

3a. Preparation of cyclopropylsulfonylamine tert-butyl carbamate, a key intermediate in the preparation of C1-substituted cyclopropylsulfonamides

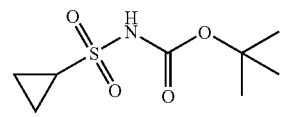

Step 1: Preparation of 3-chloropropylsulfonamide

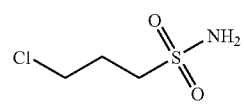

A solution of 3-chloropropanesulfonyl chloride (55 g, 310.7 mmol) was dissolved in THF (200 mL) and added dropwise over 30 minutes to a solution of NH$_4$OH (200 mL) at 0° C. The reaction mixture was warmed to room temperature, stirred 1 hour, and the aqueous layer extracted with dichloromethane (4×500 mL). The combined extracts were washed with 1N HCl (150 mL), water (150 mL), dried over MgSO$_4$, filtered, and concentrated in vacuo. The crude solid was recrystallized from the minimum amount of dichloromethane in hexanes to provide the desired product as a white solid (45.3 g, 93%). $^1$H NMR (CDCl$_3$) δ 2.34 (m, 2H), 3.32 (t, J=7.3 Hz, 2H), 3.70 (t, J=6.2 Hz, 2H), 4.83 (s, 2H); $^{13}$C NMR (CDCl$_3$) δ 27.10, 42.63, 52.57.

Step 2: Preparation of 3-chloropropylsulfonylamine tert-butylcarbamate

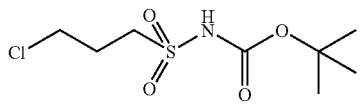

A solution of the product of Step 1 (30.2 g, 191.5 mmol), triethylamine (30.2 mL, 217.0 mmol), and 4-DMAP (2.40 g, 19.6 mmol) in dichloromethane (350 mL) at 0° C. was treated dropwise with a solution of di-tert-butyldicarbonate (47.2 g, 216.9 mmol) in dichloromethane (250 mL) over 30 minutes. The reaction mixture was warmed to room temperature, stirred an additional 3 hours, and was washed with 1N HCl (300 mL), water (300 mL), and brine (300 mL), dried over MgSO$_4$, filtered, and concentrated in vacuo to provide the crude product. This material was triturated with 70 mL of 5% dichloromethane in hexanes to provide the desired product as an off-white solid (47.2 g, 96%): $^1$H NMR (CDCl$_3$) δ 1.51 (s, 9H), 2.33 (m, 2H), 3.60 (t, J=7.3 Hz, 2H), 3.68 (t, J=6.21 Hz, 2H); $^{13}$C NMR (CDCl$_3$) δ 26.50, 27.95, 42.37, 50.40, 84.76, 149.53.

Step 3: Preparation of cyclopropylsulfonylamine tert-butyl carbamate

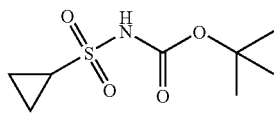

A solution of n-butyllithium (74.7 mL, 119.5 mmol, 1.6M in hexane) was dissolved in dry THF (105 mL) and cooled to −78° C. under an argon atmosphere. To this solution was added a solution of the product of Step 2 (14 g, 54.3 mmol) in dry THF (105 mL) dropwise over 20-30 minutes. The dry ice bath was removed and the reaction mixture was allowed to warm to room temperature over a period of 2 hours. The reaction mixture was quenched with glacial acetic acid (3.4 mL), concentrated in vacuo, and partitioned between dichloromethane (100 mL) and water (100 mL). The organic phase was washed with brine (100 mL), dried (MgSO$_4$), filtered, and concentrated in vacuo to provide the desired product as a waxy off-white solid (12.08 g, 100%): $^1$H NMR (CDCl$_3$) δ 1.10 (m, 2H), 1.34 (m, 2H), 1.50 (s, 9H), 2.88 (m, 1H), 7.43 (s, 1H). $^{13}$C NMR (CDCl$_3$) δ 6.21, 28.00, 31.13, 84.07, 149.82.

3b. Preparation of 1-methoxy-methylcyclopropy-sulfonamide

Step 1: Preparation of 1-methoxymethylcyclopropylsulfonylamine tert-butylcarbamate To a solution of cyclopropylsulfonylamine tert-butyl carbamate (1.0 g, 4.5 mmol) dissolved in THF (30 mL) cooled to −78° C., was added n-butyllithium (6.4 mL, 10.2 mmol, 16M in hexane) and the reaction mixture was stirred for 1 hour. To this solution was added a neat solution of chloromethyl methyl ether (0.40 mL, 5.24 mmol), and the mixture was slowly allowed to warm to room temperature overnight. The solution pH was adjusted to 3 using 1N aqueous HCl and was then extracted with ethyl acetate (4×50 mL portions). The combined extracts were dried (MgSO$_4$), filtered, and concentrated to afford 1-methoxymethylcyclopropylsulfonylamine tert-butylcarbamate, as a waxy solid (1.20 g, 100%) which was taken directly into the next reaction without further purification: $^1$H NMR (CDCl$_3$) δ 1.03 (m, 2H), 1.52 (s, 9H), 1.66 (m, 2H), 3.38 (s, 3H), 3.68 (s, 2H), 7.54 (s, 1H); $^{13}$C NMR (CDCl$_3$) δ 11.37, 28.29, 40.38, 58.94, 73.43, 83.61, 149.57.

Step 2: Preparation of 1-methoxymethylcyclopropysulfonamide

A solution of 1-methoxymethylcyclopropylsulfonylamine tert-butylcarbamate (1.14 g, 4.30 mmol) was dissolved in a solution of 50% TFA/dichloromethane (30 mL) and was stirred at room temperature for 16 hours. The solvent was removed in vacuo and the residue chromatographed over 80 g of SiO$_2$ (eluting with 0% to 60% ethyl acetate/hexanes to 1-methoxymethylcyclopropylsulfonamide as a white solid (0.55 g, 77% overall over two steps): $^1$H NMR (CDCl$_3$) δ 0.95 (m, 2H), 1.44 (m, 2H), 3.36 (s, 3H), 3.65 (s, 2H), 4.85 (s, 2H); $^{13}$C NMR (CDCl$_3$) δ 111.7, 40.87, 59.23, 74.80; LRMS m/z 183 (M$^+$+NH$_4$).

3c. Preparation of 1-cyclopropylmethylcyclopropylsulfonamide

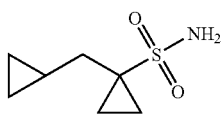

Step 1: Preparation of 1-cyclopropylmethylcyclopropylsulfonylamine tert-butylcarbamate

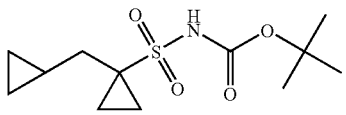

1-Cyclopropylmethylcyclopropylsulfonylamine tert-butylcarbamate was obtained in 92% yield according to the procedure described in the synthesis of 1-methoxymethylcyclopropylsulfonylamine tert-butylcarbamate, except 1.10 equivalents of cyclopropylmethyl bromide were used as electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-cyclopropylmethyl-cyclopropylsulfonamide

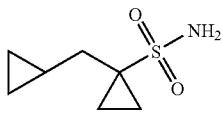

This compound was obtained in 65% yield from 1-cyclopropylmethylcyclopropylsulfonylamine tert-butylcarbamate according to the procedure described for the synthesis of 1-methoxymethylcyclopropylsulfonamide. The compound was purified by column chromatography over SiO$_2$ using 0% to 60% ethyl acetate in hexanes as the eluent: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

3d. Preparation of 1-propylcarbamoylcyclopropane-sulfonamide

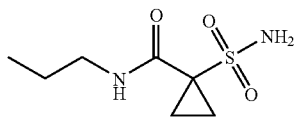

Step 1: Preparation of 1-propylcarbamoylcyclopropanesulfonamide tert-butylcarbamate

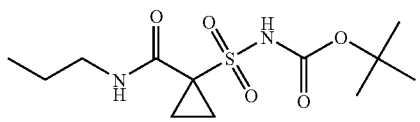

This compound was obtained in a crude 100% yield according to the procedure described for the synthesis of 1-methoxymethylcyclopropylsulfonylamine tert-butyl-carbamate except that 1.10 equivalents of n-propyl isocyanate was used as the electrophile. The compound was taken directly into the next reaction without purification: $^1$H NMR (CDCl$_3$) δ 0.10 (m, 2H), 0.51 (m, 2H), 0.67 (m, 10H), 1.10 (m, 2H), 1.49 (s, 9H), 1.62 (m, 21), 1.87 (d, J=7.0 Hz, 21).

Step 2: Preparation of 1-propylcarbamoylcyclopropane-sulfonamide

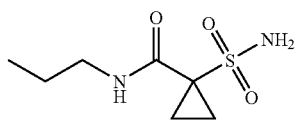

This compound was obtained in 50% yield from 1-propylcarbamoylcyclopropanesulfonamide tert-butylcarbamate according to the procedure described for the synthesis of 1-methoxymethylcyclopropylsulfonamide, except that no chromatography was used as the material was recrystallized from the minimum amount of dichloromethane/hexanes: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

3e. Preparation of 1-(3,5-dimethylisoxazol-4-yl)carbamoylcyclopropanesulfonamide

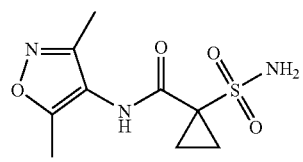

Step 1: Preparation of 1-(3,5-dimethylisoxazol-4-yl)carbamoylcyclopropanesulfonamide tert-butylcarbamate

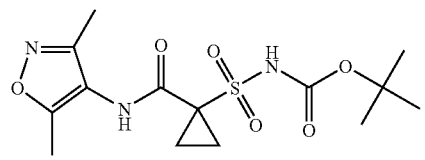

This compound was obtained in a crude 100% yield according to the procedure described for the synthesis of 1-methoxymethylcyclopropylsulfonylamine tert-butylcarbamate except that 1.20 equivalents of 3,5-dimethylisoxazole-4-isocyanate was used as the electrophile. The compound was taken directly into the next reaction without purification.

Step 2: Preparation of 1-(3,5-dimethylisoxazol-4-yl) carbamoylcyclopropanesulfonamide

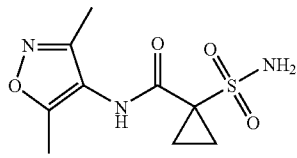

This compound was obtained in 50% yield (580 mg) from 1.62 g (4.52 mmol) of 1-(3,5-dimethylisoxazol-4-yl)carbamoylcyclopropanesulfonamide tert-butylcarbamate using 30 mL (120 mmol) of 4N HCl/dioxanes, stirring overnight, concentration and chromatography over a BIOTAGE® 40M column (eluting with 0% to 5% methanol/dichloromethane: $^1$H NMR (methanol-$d_4$) δ 1.57 (m, 2H), 1.61 (m 2H), 2.15 (s, 3H), 2.30 (s, 3H), 4.84 (s, 3H); $^{13}$C NMR (methanol-$d_4$) δ 9.65, 10.94, 15.01, 46.11, 114.82, 159.45, 165.55, 168.15; LRMS m/z 260 (M$^+$+H).

4. Preparation of Cycloalkylsulfonamides from Cycloalkylbromides

4a. Preparation of Cyclobutylsulfonamide from Cyclobutyl Bromide

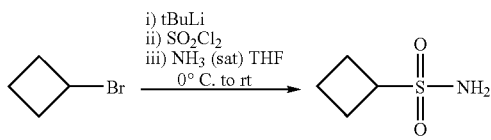

To a solution of 5.0 g (37.0 mmol) of cyclobutyl bromide in 30 mL of anhydrous diethyl ether (diethyl ether) cooled to −78° C. was added 44 mL (74.8 mmol) of 1.7M tert-butyllithium in pentanes. The solution was slowly warmed to −35° C. over 1.5 hours. This mixture was cannulated slowly into a solution of 5.0 g (37.0 mmol) of freshly distilled sulfuryl chloride in 100 mL of hexanes cooled to −40° C., warmed to 0° C. over 1 hour and carefully concentrated in vacuo. This mixture was redissolved in diethyl ether, washed once with some ice-cold water, dried (MgSO$_4$), filtered, and concentrated carefully. This mixture was redissolved in 20 mL of THF, added dropwise to 500 mL of saturated NH$_3$ in THF, and was allowed to stir overnight. The mixture was concentrated in vacuo to a crude yellow solid and was recrystallized from the minimum amount of dichloromethane in hexanes with 1-2 drops of methanol to provide 1.90 g (38%) of the desired product as a white solid. $^1$H NMR (CDCl$_3$) δ 1.95-2.06 (m, 2H), 2.30-2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M−H)$^−$ calcd for C$_4$H$_8$NSO$_2$: 134.0276. found 134.0282.

4b. Preparation of Cyclopentyl Sulfonamide

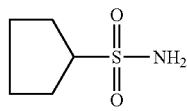

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and the solution was then concentrated. The residue was recrystallized from the minimum amount of dichloromethane in hexanes with 1-2 drops of methanol to provide 2.49 g (41%) of the desired product as a white solid. $^1$H NMR (CDCl$_3$) δ 1.58-1.72 (m, 2H), 1.74-1.88 (m, 2H), 1.94-2.14 (m, 4H), 3.48-3.59 (m, 1H), 4.80 (br s, 2H); $^{13}$C NMR (CDCl$_3$) δ 25.90, 28.33, 63.54; MS m/e 148 (M−H)$^−$.

4c. Preparation of Cyclohexyl Sulfonamide

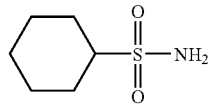

A solution of 18.5 mL (37.0 mmol) of 2M cyclohexylmagnesium chloride (TCI Americas) in diethyl ether was added dropwise to a solution of 3.0 mL (37.0 mmol) freshly distilled sulfuryl chloride in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and was concentrated. The concentrate was recrystallized from the minimum amount of dichloromethane in hexanes with 1-2 drops of methanol to provide 1.66 g (30%) of the desired product as a white solid: $^1$H NMR (CDCl$_3$) δ 1.11-1.37 (m, 3H), 1.43-1.56 (m, 2H), 1.67-1.76 (m, 1H), 1.86-1.96 (m, 2H), 2.18-2.28 (m, 2H), 2.91 (tt, J=12, 3.5 Hz, 1H), 4.70 (br s, 2H); $^{13}$C NMR (CDCl$_3$) δ 25.04, 25.04, 26.56, 62.74; MS m/e 162 (M−1)$^−$.

4d. Preparation of Neopentyl Sulfonamide

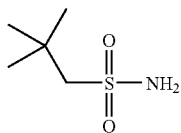

Following the procedure for the preparation of cyclohexylsulfonamide, 49 mL (37 mmol) of 0.75M neopentylmagnesium chloride (Alfa) in diethyl ether was converted to 1.52 g (27%) of the desired product as a white solid. $^1$H NMR (CDCl$_3$) δ 1.17 (s, 9H), 3.12 (s, 2H), 4.74 (brs, 2H); $^{13}$C NMR (CDCl$_3$) δ 29.46, 31.51, 67.38; MS m/e 150 (M−1)$^−$.

4e. Preparation of Cyclobutylcarbinylsulfonamide

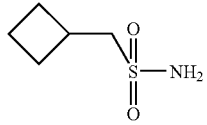

A solution of 12.3 g (83 mmol) of cyclobutylcarbinyl bromide (Aldrich) and 13.7 g (91 mmol) of sodium iodide in 150 mL of acetone was heated to reflux overnight and then cooled to room temperature. The inorganic solids were removed by filtration and the acetone and cyclopropylcarbinyl iodide (8.41 g, 46%) were removed by distillation (ambient temperature and 150 torr at 80° C., respectively).

A solution of 4.0 g (21.98 mmol) of cyclobutyl carbinyl iodide in 30 mL of anhydrous diethyl ether cooled to −78° C. was cannulated into a solution of 17 mL (21.98 mmol) of 1.3M sec-butyllithium in cyclohexanes and the solution was stirred for 5 minutes. To this mixture was cannulated a solution of 3.0 g (21.98 mmol) of freshly distilled sulfuryl chloride in 110 mL of hexanes cooled to −78° C., the mixture warmed to room temperature over 1 hour and was then carefully concentrated in vacuo. This mixture was redissolved in diethyl ether, washed once with some ice-cold water, dried (MgSO$_4$), filtered, and concentrated carefully. This mixture was redissolved in 30 mL of THF, added dropwise to 500 mL of saturated NH$_3$ in THF and was allowed to stir overnight. The mixture was concentrated in vacuo to a crude yellow solid and was recrystallized from the minimum amount of dichloromethane in hexanes with 1-2 drops of methanol to provide 1.39 g (42%) of the desired product as a white solid. $^1$H NMR (CDCl$_3$) δ 1.81-2.03 (m, 4H), 2.14-2.28 (m, 2H), 2.81-2.92 (m, 1H), 3.22 (d, J=7 Hz, 2 μl), 4.74 (brs, 2H); $^{13}$C NMR (CDCl$_3$) δ 19.10, 28.21, 30.64, 60.93. MS m/e 148 (M−H)$^−$.

4f. Preparation of Cyclopropylcarbinylsulfonamide

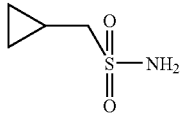

Using the procedure employed for the preparation of cyclobutylcarbinylsulfonamide, cyclopropylcarbinylsulfonamide was prepared from cyclopropylcarbinyl bromide (Aldrich) (see also *JACS* 1981, p. 442-445). $^1$H NMR (CDCl$_3$) δ 0.39-0.44 (m, 2H), 0.67-0.76 (m, 2H), 1.13-1.27 (m, 1H), 3.03 (d, J=7.3 Hz, 2H), 4.74 (brs, 2H); $^{13}$C NMR (CDCl$_3$) δ 4.33, 5.61, 59.93; MS in/c 134 (M−1).

4g. Preparation of 2-thiophenesulfonamide

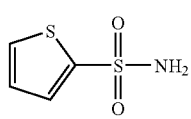

The desired product was prepared from 2-thiophenesulfonyl chloride (purchased from Aldrich) using the method described in *Justus Liebigs Ann. Chem.*, 501:174-182 (1933).

4h. Preparation of 4-bromobenzenesulfonamide

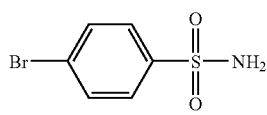

4-Bromophenylsulfonamide was prepared by treatment of commercially available 4-bromosulfonyl chloride with saturated ammonia in THF.

5. General Procedure for the Preparation of Sulfamides

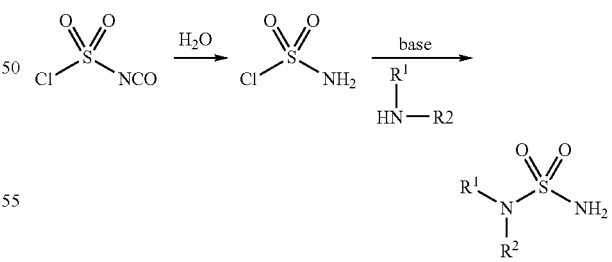

The intermediate sulfamoyl chloride was prepared by addition of water (I equiv) in THF to a cold (−20° C.) stirred solution of chlorosulfonyl isocyanate (1 equiv) in THF and the resulting solution allowed to warm to 0° C. To this solution was added anhydrous triethylamine (1 equiv) followed by requisite secondary amine (1 equiv). The reaction mixture was warmed to room temperature, then filtered and the filtrate was concentrated to afford the desired sulfamides.

Example 2

Preparation of P1 Intermediates

5. 1-tert-Butoxycarbonylaminocyclopropane carboxylic acid is commercially available

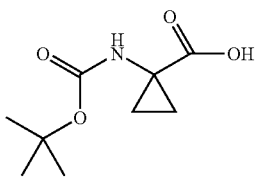

6. Preparation of 1-aminocyclobutanecarboxylic acid methyl ester hydrochloride

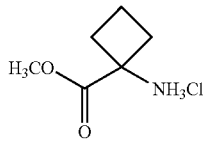

1-Aminocyclobutanecarboxylic acid (100 mg, 0.869 mmol) (Tocris) was dissolved in 10 mL of methanol. HCl gas was bubbled in for 2 hours. The reaction mixture was stirred for 18 hours, and then concentrated in vacuo to give 144 mg of a yellow oil. Trituration with 10 mL of diethyl ether provided 100 mg of the desired product as a white solid. $^1$H NMR (CDCl$_3$) δ 2.10-2.25 (m, 1H), 2.28-2.42 (m, 1H), 2.64-2.82 (m, 4H), 3.87 (s, 3H), 9.21 (br s, 3H).

7a. Preparation of (1R,2R)/(1S,2S) 1-amino-2-ethylcyclopropanecarboxylic acid tert-butyl ester (racemic mixture)

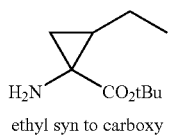

ethyl syn to carboxy

Step 1: Preparation of 2-ethylcyclopropane-1,1-dicarboxylic acid di-tert-butyl ester, shown below

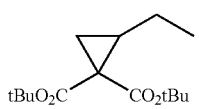

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred for 18 hours at room temperature and treated with a mixture of ice and water. The crude product was extracted with dichloromethane (3×) and sequentially washed with water (3×), and brine. The organic extracts were combined, dried (MgSO$_4$), filtered, and concentrated in vacuo. The resulting residue was purified by flash column chromatography (100 g SiO$_2$, 3% diethyl ether in hexane) to provide the desired product (18.3 g, 67.8 mmol, 73% yield) which was used directly in the next reaction.

Step 2: Preparation of racemic 2-ethylcyclopropane-1,1-dicarboxylic acid tert-butyl ester, shown below

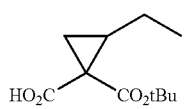

The product of Step 1 (18.3 g, 67.8 mmol) was added to a suspension of potassium tert-butoxide (33.55 g, 299.0 mmol) in dry diethyl ether (500 mL) at 0° C., treated with H$_2$O (1.35 mL, 75.0 mmol), and was vigorously stirred overnight at room temperature. The reaction mixture was poured in a mixture of ice and water and washed with diethyl ether (3×). The aqueous layer was adjusted to acidic pH with a 10% aqueous citric acid solution at 0° C. and extracted with ethyl acetate (3×). The combined organic layers were washed with water (2×), brine, dried (MgSO$_4$), filtered, and concentrated in vacuo to provide the desired product as a pale yellow oil (10 g, 46.8 mmol, 69% yield).

Step 3: Preparation of (1R,2R)/(1S,2S) 2-ethyl-1-(2-trimethylsilanylethoxycarbonylamino)cyclopropane-carboxylic acid tert-butyl ester, shown below

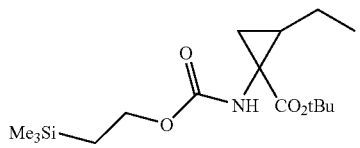

To a suspension of the product of Step 2 (10 g, 46.8 mmol) and 3 g of freshly activated 4 Å molecular sieves in dry benzene (160 mL) was added triethylamine (7.50 mL, 53.8 mmol) and DPPA (11 mL, 10.21 mmol). The reaction mixture was heated to reflux for 3.5 hours, treated with 2-trimethyl-silylethanol (13.5 mL, 94.2 mmol), and heated to reflux overnight. The reaction mixture was filtered, diluted with diethyl ether, washed sequentially with 10% aqueous citric acid solution, water, saturated aqueous NaHCO$_3$, water (2×), and brine (2×), dried (MgSO$_4$), filtered, and concentrated in vacuo. The residue was suspended with 10 g of Aldrich polyisocyanate scavenger resin in 120 mL of dichloromethane, stirred at room temperature overnight, and filtered to provide the desired product (8 g, 24.3 mmol; 52%) as a pale yellow oil: $^1$H NMR (CDCl$_3$) δ 0.03 (s, 9H), 0.97 (m, 5H), 1.20 (br m, 1H), 1.45 (s, 9H), 1.40-1.70 (m, 4H), 4.16 (m, 2H), 5.30 (br s, 1H).

Step 4: Preparation of (1R,2R)/(1S,2S) 1-amino-2-ethylcyclopropanecarboxylic acid tert-butyl ester (racemic mixture), shown below

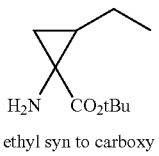

ethyl syn to carboxy

To the product of Step 3 (3 g, 9 mmol) was added a 1.0M TBAF solution in THF (9.3 mL, 9.3 mmol). The mixture was heated to reflux for 1.5 hours, cooled to room temperature, and diluted with 500 mL of ethyl acetate. The solution was successively washed with water (2×100 mL) and brine (2×100 mL), dried (MgSO$_4$), filtered, and concentrated in vacuo to provide the desired product.

8. Preparation of racemic (1R,2S)/(1S,2R)-1-amino-2-vinylcyclopropane carboxylic acid ethyl ester

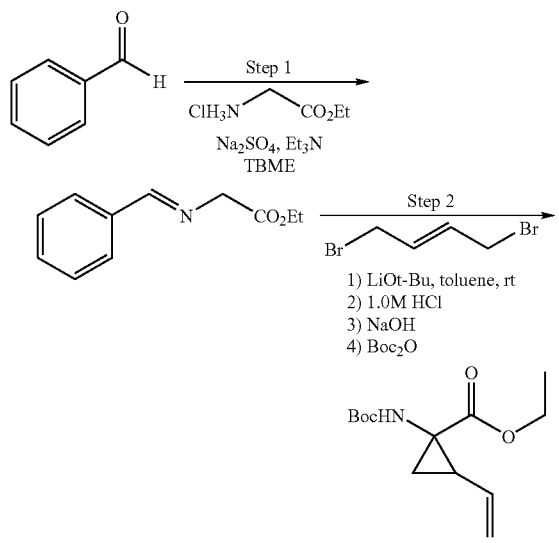

Scheme 1

Racemate:
1:1 mixture of (1R, 2S) and (1S, 2R)

Step 1

Glycine ethyl ester hydrochloride (304 g, 2.16 mole) was suspended in tert-butylmethyl ether (1.6 L). Benzaldehyde (231 g, 2.16 mole) and anhydrous sodium sulfate (155 g, 1.09 mole) were added, and the mixture was cooled to 0° C. using an ice-water bath. Triethylamine (455 mL, 3.26 mole) was added dropwise over 30 minutes and the mixture was stirred for 48 hours at room temperature. The reaction was then quenched by addition of ice-cold water (1 L) and the organic layer was separated. The aqueous phase was extracted with tert-butylmethyl ether (0.5 L) and the organic phases were combined and washed with a mixture of saturated aqueous NaHCO$_3$ (1 L) and brine (1 L). The organic layer was dried over MgSO$_4$, filtered, and concentrated in vacuo to provide 392.4 g of the N-benzyl imine product as a thick yellow oil that was used directly in the next step. $^1$H NMR (CDCl$_3$, 300 MHz) δ 1.32 (t J=7.1 Hz, 3H), 4.24 (q, J=7.1 Hz, 2H), 4.41 (d, J=1.1 Hz, 2H), 7.39-7.47 (m, 3H), 7.78-7.81 (m, 2H), 8.31 (s, 1H).

Step 2

To a suspension of lithium tert-butoxide (84.1 g, 1.05 mol) in dry toluene (1.2 L), was added dropwise a mixture of the N-benzyl imine of glycine ethyl ester (100 g, 0.526 mol) and trans-1,4-dibromo-2-butene (107 g, 0.500 mol) in dry toluene (0.6 L) over 60 minutes. Upon completion of the addition, the deep red mixture was quenched by addition of water (1 L) and tert-butylmethyl ether (TBME, 1 L). The aqueous phase was separated and extracted a second time with TBME (1 L). The organic phases were combined, 10M HCl (1 L) was added and the mixture stirred at room temperature for 2 hours. The organic phase was separated and extracted with water (0.8 L). The aqueous phases were then combined, saturated with salt (700 g), and TBME (1 L) was added and the mixture was cooled to 0° C. The stirred mixture was then made basic to pH=14 by the dropwise addition of 10.0M NaOH, the organic layer was separated, and the aqueous phase was extracted with TBME (2×500 mL). The organic extracts were combined, dried over MgSO$_4$, filtered and concentrated to a volume of 1 L. To this solution of free amine was added Boc$_2$O or di-tert-butyldicarbonate (131 g, 0.600 mol) and the mixture stirred for 4 days at room temperature. Additional di-tert-butyldicarbonate (50 g, 0.23 mol) was added to the reaction and the mixture was refluxed for 3 hours and was then allowed cool to room temperature overnight. The reaction mixture was dried over MgSO$_4$, filtered, and concentrated in vacuo to provide 80 g of crude material. This residue was purified by flash chromatography (2.5 kg of SiO$_2$, eluted with 1% to 2% CH$_3$OH/CH$_2$Cl$_2$) to provide 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR (CDCl$_3$, 300 MHz) δ 1.26 (t, J=7.1 Hz, 3H), 1.46 (s, 9H), 1.43-1.49 (m, 1H), 1.76-1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M−1).

9. Resolution of N-Boc-(1R,2S)/(1S,2R)-1-amino-2-vinylcyclopropane carboxylic acid ethyl ester

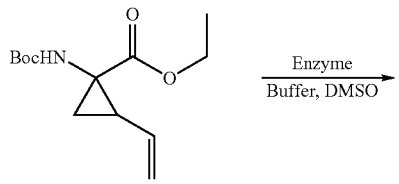

Scheme 2

Racemate:
1:1 mixture of (1R, 2S) and (1S, 2R)

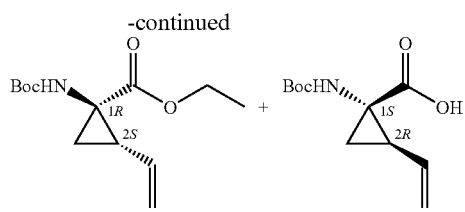

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Alcalase 2.4L (about 425 mL) Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 minutes. The reaction temperature was then maintained at 40° C. for 24.5 hours during which time the pH of the mixture was adjusted to 8.0 at the 1.5 hour and 19.5 hour time points using 50% NaOH in water. After 24.5 hours, the enantio-excess of the ester was determined to be 97.2%, and the reaction was cooled to room temperature (26° C.) and stirred overnight (16 hours) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% $NaHCO_3$ (3×100 mL), water (3×100 mL), and concentrated in vacuo to give the enantiomerically pure N-Boc-(1R,2S)/-1-amino-2-vinylcyclopropane carboxylic acid ethyl ester as light yellow solid (42.55 g; purity: 97% @ 210 nm, containing no acid; 100% enantiomeric excess ("ee")).

The aqueous layer from the extraction process was then acidified to pH 2 with 50% $H_2SO_4$ and extracted with MTBE (2×2 L). The MTBE extract was washed with water (3×100 mL) and concentrated to give the acid as light yellow solid (42.74 g; purity: 99% @ 210 nm, containing no ester).

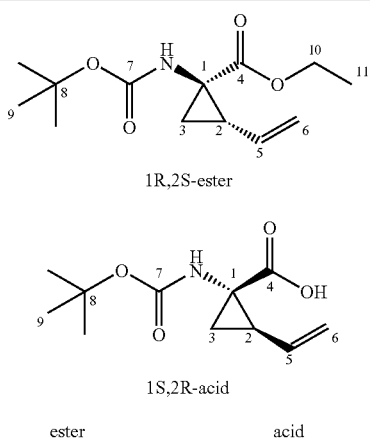

| | ester | acid |
|---|---|---|
| High ResolutionMass Spec | (+) ESI, $C_{13}H_{22}NO_4$, $[M+H]^+$, calcd. 256.1549, found 256.1542 | (−) ESI, $C_{11}H_{16}NO_4$, $[M−H]^−$, calcd. 226.1079, found 226.1089 |

NMR observed chemical shift
  Solvent: $CDCl_3$ (proton δ 7.24 ppm, C-13 δ 77.0 ppm)
  Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = 9.0 Hz) | 35.0 |
| 3a | 1.76 (br) | 23.2 | 1.79 (br) | 23.4 |
| 3b | 1.46 (br) | | 1.51, (br) | |
| 4 | — | 170.8 | — | 175.8 |
| 5 | 5.74 (ddd, J = 9.0, 10.0, 17.0 Hz) | 133.7 | 5.75 (m) | 133.4 |
| 6a | 5.25 (d, J = 17.0 Hz) | 117.6 | 5.28 (d, J = 17.0 Hz) | 118.1 |
| 6b | 5.08 (dd, J = 10.0, 1.5 Hz) | | 5.12 (d, J = 10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J = 7.5 Hz) | 14.2 | — | — |

Resolution B

To 0.5 mL 100 mM Heps.Na buffer (pH 8.5) in a well of a 24 well plate (capacity: 10 mL/well), 0.1 mL of Savinase 16.0L protease from *Bacillus clausii*) Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hours, enantio-excess of the ester was determined to be 44.3% as following: 0.1 mL of the reaction mixture was removed and mixed well with 1 mL ethanol; after centrifugation, 10 microliter ("μL") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μL of the supernatant was analyzed with the chiral HPLC and enantio-excess of the ester was determined to be 100%.

Resolution C

To 0.5 mL 100 mM Heps.Na buffer (pH 8.5) in a well of a 24 well plate (capacity: 10 mL/well), 0.1 mL of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after centrifugation, 10 μL of the supernatant was analyzed with the chiral HPLC. To the remaining reaction mixture, 0.1 mL of DMSO was added, and the plate was incubated for additional 3 days at 250 rpm at 40° C., after which 4 mL of ethanol was added to the well. After centrifugation, 10 μL of the supernatant was analyzed with the chiral HPLC and enantio-excess of the ester was determined to be 100%.

Samples analysis was carried out in the following manner:
1) Sample preparation: About 0.5 mL of the reaction mixture was mixed well with 10 volume of ethanol. After centrifugation, 10 μL of the supernatant was injected onto HPLC column.
2) Conversion determination:
Column: YMC ODS A, 4.6×50 mm, S-5 μm
Solvent: A, 1 mM HCl in water; B, $CH_3CN$
Gradient: 30% B for 1 min; 30% to 45% B over 0.5 min; 45% B for 1.5 min; 45% to 30% B over 0.5 minutes.

Flow rate: 2 mL/min
UV Detection: 210 mm
Retention time: acid, 1.2 min; ester, 2.8 minutes.
3) Enantio-excess determination for the ester:
Column: CHIRACEL OD-RH, 4.6×150 mm, S-5 μm
Mobile phase: $CH_3CN$/50 mM $HClO_4$ in water (67/33)
Flow rate: 0.75 mL/min.
UV Detection: 210 nm.
Retention time:
   (1S,2R)-1-amino-2-vinylcyclopropane carboxylic acid 5.2 min;
   Racemate (1R,2S)/(1S,2R)-1-amino-2-vinylcyclopropane carboxylic acid ethyl ester 18.5 minutes and 20.0 min;
   (1R,2S)-1-amino-2-vinylcyclopropane carboxylic acid ethyl ester 18.5 minutes.

Resolution D

5 L of 0.3 M sodium phosphate buffer (pH 8) was maintained at 38° C. in a 20 Liter jacked reactor, stirred at 130 rpm. Four liters of Alcalase 2.4L (Novozymes North America Inc.) and 1 liter of DI water were added to the reactor. When temperature of the mixture closed to 38° C., pH was adjusted to 7.8 with 10 N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funnel. The reaction temperature was then adjusted to 48° C. After 21 hours, enantio-excess of the ester reached 99.3%. Heating was stopped at 24 hours and the reaction was slowly cooled down to room temperature (about 25° C.) and stirred overnight. The pH of the reaction mixture was adjusted to 8.5 with 10 N NaOH and the mixture was extracted with MTBE (2×4 L). The combined MTBE extract was washed with 5% $NaHCO_3$ (3×400 mL) and water (3×400 mL), and concentrated to give enantiomerically pure N-Boc-(1R,2S)/-1-amino-2-vinylcyclopropane carboxylic acid ethyl ester as light yellow crystal (259 g; purity: 96.9% @ 210 nm, containing no acid; 100% ee).

Resolution E

10 L of 0.1 M sodium phosphate buffer (pH 8) was maintained at 40° C. in a 20 Liter jacked reactor, stirred at 360 rpm. 1.5 liters of Alcalase 2.4L Novozymes North America Inc.) was added to the reactor. When the temperature of the mixture closed to 38° C., the pH was adjusted to 8.0 with 10 N NaOH. A solution of the racemic N-Boc-(1R,2S)(1S,2R)-1-amino-2-vinylcyclopropane carboxylic acid ethyl ester (200 grams) in 2 liters DMSO was added to the reactor over a period of 1 hour via an addition funnel. The reaction temperature was then adjusted to 40° C. After 3 hours, the pH was adjusted to 8.0 with 10 N NaOH. After 21 hours, the reaction was cooled down to 25° C., the pH of the reaction mixture was adjusted to 8.5 with 10 N NaOH and the mixture was extracted with MTBE (2×5 L). The combined MTBE extract was washed with 5% $NaHCO_3$ (3×500 mL) and water (3×200 mL), and concentrated to give 110 gram of yellow oil. The oil was set at room temperature under house vacuum and gave enantiomerically pure N-Boc-(1R,2S)/-1-amino-2-vinylcyclopropane carboxylic acid ethyl ester as colorless long rod crystal (101 g; purity: 97.9% @ 210 nm, containing no acid; 100% ee).

The crystal structure enantiomerically pure N-Boc-(1R, 2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N . . . O 3.159 Å).

Structure of N-Boc-(1R,2S)-1-amino-2-vinylcyclopropane carboxylic acid ethyl ester:

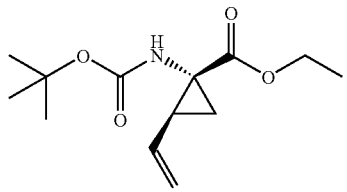

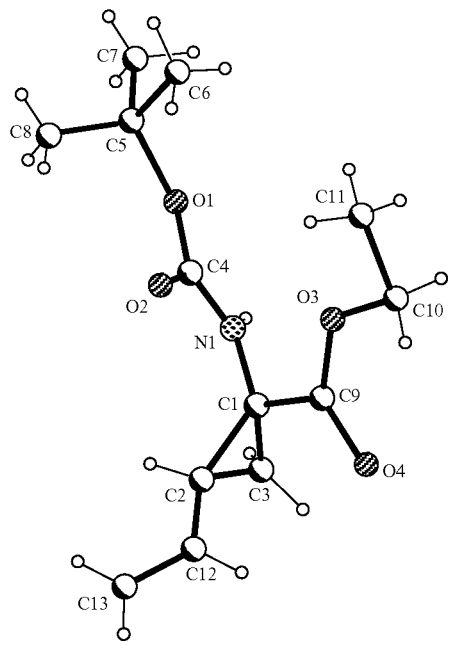

| Crystal Data | Experimental |
|---|---|
| Chemical formula: $C_{13}H_{21}N_1O_4$ | Crystallization |
| Crystal system: Othorhombic | Crystal source: MTBE |
| Space Group: $P2_12_12_1$ | Crystal description: Colorless rod |
| a = 5.2902(1) Å α = 90° | Crystal size (mm): 0.12 × 0.26 × 0.30 |
| b = 13.8946(2) Å β = 90° | Data Collection |
| c = 19.9768(3) Å γ = 90° | Temperature (K): 293 |
| V = 1468.40(4) Å$^3$ | $θ_{max}$ (°): 65.2 (Cu Kα) |
| Z = 4 $d_x$ = 1.155 g cm$^{-3}$ | No. of reflections measured: 7518 |
| No. of reflections for lattice parameters: 6817 | No. of independent refections: 2390 ($R_{int}$ = 0.0776) |
| θ range for lattice parameters (°): 2.2-65.2 | No. of observed reflections (I ≥ 2 σ: 2284 |
| Absorption coefficient (mm$^{-1}$): 0.700 | Absorption correction ($T_{min}$-$T_{max}$): 0.688-1.000 |

Resolution F

5 L of 0.2 M sodium borate buffer (pH 9) was maintained at 45° C. in a 20 liter jacked reactor, and stirred at 400 rpm. Three liter of DI water and four liters of Savinase 16L, type EX (Novozymes North America Inc.) were added to the reactor. When temperature of the mixture closed to 45° C., pH was adjusted to 8.5 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 40 minutes, via an addition funnel. The reaction temperature was then adjusted to 48° C. After 2 hours, pH was adjusted to pH 9.0 with 10 N NaOH. At 18 hour, enantio-excess of the ester reached 72%, pH was adjusted to 9.0 with 10 N NaOH. At 24 hours, temperature was lowered to 35° C. At 42 hours, the temperature was raised to 48° C. and the pH was adjusted to 9.0 with 10 N NaOH. Heating was stopped at 48 hours and the reaction was slowly cooled down to room temperature (about 25° C.) and stirred overnight. At 66 hour, pH of the reaction mixture was 8.6. The mixture was extracted with MTBE (2×4 L). The combined MTBE extract was washed with 5% NaHCO₃ (6×300 mL) and water (3×300 mL), and concentrated to give enantiomerically pure N-Boc-(1R,2S)/-1-amino-2-vinylcyclopropane carboxylic acid ethyl ester as light yellow crystal (101A g; purity: 95.9% @ 210 nm, containing no acid; 98.6% ee).

10. Preparation of chiral (1R,2S)-1-amino-2-vinylcyclopropane carboxylic acid ethyl ester hydrochloride

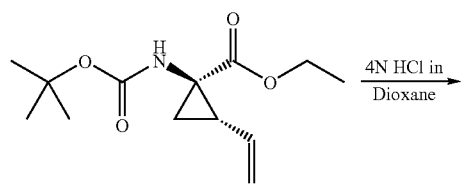

(1R,2S)N-Boc-1-amino-2-vinylcyclopropanecarboxylic acid ethyl ester (8.5 g, 33.3 mmol) was stirred under a nitrogen atmosphere with 200 mL of 4N HCl/dioxane (Aldrich) at room temperature for 3 hours. The solvent was removed under reduced pressure keeping the temperature below 40° C. This gave 6.57 g (~100%) of (1R,2S)-1-amino-2-vinylcyclopropanecarboxylic acid ethyl ester hydrochloride as a light tan solid. ¹H NMR (300 MHz, CD₃OD) δ 1.31 (t, J=7.0 Hz, 3H), 1.69-1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69-5.81 (m, 1H). MS m/z 156 (M⁺+1).

11. Preparation of N-Boc-(1R,2S)-1-amino-2-cyclopropylcyclopropane carboxylic acid ethyl ester

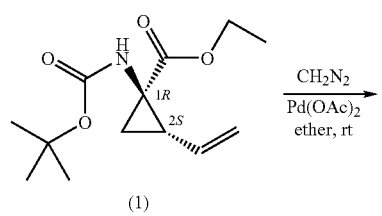

(1)

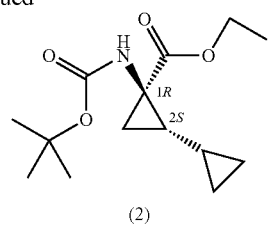

(2)

A solution of N-Boc-(1R,2S)-1-amino-2-vinylcyclopropane carboxylic acid (255 mg, 1.0 mmol) in diethyl ether (10 mL) was treated with palladium acetate (5 mg, 0.022 mmol). The orange/red solution was placed under a nitrogen atmosphere. An excess of diazomethane in diethyl ether was added dropwise over the course of 1 hour. The resulting solution was stirred at room temperature for 18 hours. The excess diazomethane was removed using a stream of nitrogen and the resulting solution was concentrated by rotary evaporation to give the crude product. Flash chromatography (10% ethyl acetate/hexane) provided 210 mg (78%) of (1R,2S)—N-Boc-1-amino-2-cyclopropylcyclopropane carboxylic acid ethyl ester as a colorless oil. MS m/z 270 (M⁺+H).

Preparation of P1'-P1 Intermediates

12. Preparation of P1P1'

Scheme 1

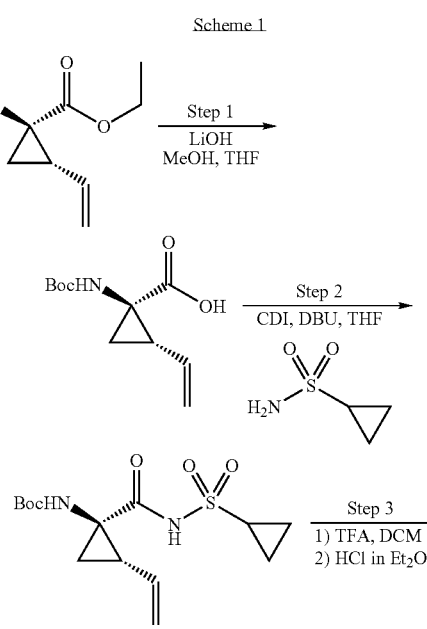

Enzymatically resolved single isomer

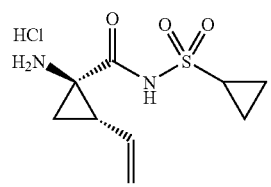

Step 1

To a solution of 1(R)-tert-butoxycarbonylamino-2(S)-vinyl-cyclopropanecarboxylic acid ethyl ester (3.28 g, 13.2 mmol) in THF (7 mL) and methanol (7 mL) was added a suspension of LiOH (1.27 g, 53.0 mmol) in water (14 mL). The mixture was stirred overnight at room temperature. To the mixture was added 10M NaOH (15 mL), water (20 mL) and ethyl acetate (20 mL). The mixture was shaken, the phases were separated, and the organic phase was again extracted with 20 mL 0.5M NaOH. The combined aqueous phases were acidified with 1.0M HCl until pH=4 and extracted with ethyl acetate (3×40 mL). The combined organic extracts were washed with brine, dried (MgSO$_4$), and filtered to provide the desired product as a white solid (2.62 g, 87%). $^1$H NMR: (DMSO-d$_6$) δ1.22-1.26 (m, 1H), 1.37 (s, 9H), 1.50-1.52 (m, 1H), 2.05 (q, J=9 Hz, 1H), 5.04 (d, J=10 Hz, 1H), 5.22 (d, J=17 Hz, 1H), 5.64-5.71 (m, 1H), 7.18, 7.53 (s, NH (rotamers), 12.4 (br s, 1H)); LC-MS MS m/z 228 (M$^+$+H).

Step 2

A solution of the product of Step 1 (2.62 g, 11.5 mmol) and CDI (2.43 g, 15.0 mmol) in THF (40 mL) was heated at reflux for 50 minutes under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 hours. The mixture was quenched with 1.0M HCl to pH 1, and THF was evaporated in vacuo. The suspension was extracted with ethyl acetate (2×50 mL) and the organic extracts were combined and dried (Na$_2$SO$_4$). Filtration, concentration, and purification by recrystallization from hexanes-ethyl acetate (1:1) provided the desired product (2.4 g) as a white solid. The mother liquor was purified by a BIOTAGE®40S column (eluted 9% acetone in dichloromethane) to give a second batch of the desired product (1.1 g). Both batches were combined (total yield 92%). $^1$H NMR: (DMSO-d$_6$) δ 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers)); LC-MS, MS m/z 331 (M$^+$+H).

Step 3

A solution of the product of Step 2 (3.5 g, 10.6 mmol) in dichloromethane (35 mL) and TFA (32 mL) was stirred at room temperature for 1.5 hours. The volatiles were removed in vacuo and the residue suspended in 1.0M HCl in diethyl ether (20 mL) and concentrated in vacuo. This procedure was repeated once. The resulting mixture was triturated with pentane and filtered to give the title compound as a hygroscopic, off-white solid (2.60 g, 92%). $^1$H NMR (DMSO-d$_6$) δ 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, TH), 5.52-5.59 (m, 1H), 9.17 (br s, 3H); LC-MS, MS m/z 231 (M$^+$+H).

13. Preparation of P1-P1' Sulfamide Derivative

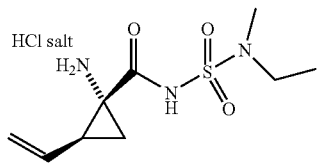

To a solution of (1R,2S) 1-tert-butoxycarbonylamino-2-vinyl-cyclopropanecarboxylic acid (217 mg, 1.194 mmol) in THF (5 mL), was added CDI (290 mg, 1.791 mmol) and the reaction mixture was heated to reflux for 45 minutes. In another round-bottomed flask, LiHMDS (10M solution in hexanes, 2.4 mL, 2.4 mmol) was added to a solution of N-ethylmethylsulfamide (330 mg, 2.388 mmol) in THF (5 mL) and the reaction mixture was stirred at room temperature for 1 hour. The two reaction mixtures were combined and stirred at room temperature for 2 hours. Water was added to quench the reaction and the reaction solution was extracted with ethyl acetate. The organic layer was separated and dried over MgSO$_4$. Filtration and concentration gave crude product which was purified by preparative HPLC to provide the desired N-Boc protected N-acylsulfamide. The Boc protecting group was then removed as the compound was dissolved in 4H HCl solution in dioxane (2 mL) and stirred at room temperature for 4 hours. Concentration provided a brownish oil as the HCl salt. (112 mg, 33% yield). 1H NMR (400 Mz, CD$_3$OD) g1.16 (t, J=7.21 Hz, 3H), 1.68 (dd, J=10.03, 7.83 Hz, 1H), 2.15 (m, 1H), 2.37 (m, 1H), 2.89 (s, 3H), 3.30 (m, 2H), 5.31 (d, J=10.27 Hz, 1H), 5.42 (d, J=17.12 Hz, 3H), 5.68 (m, 1H). LC-MS (retention time: 0.883 minutes), MS m/z 270 (M+Na$^+$).

Compound Preparation

Example 1

Compound 1

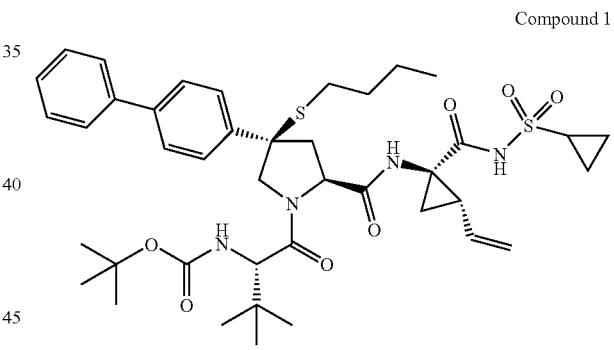

Scheme 1

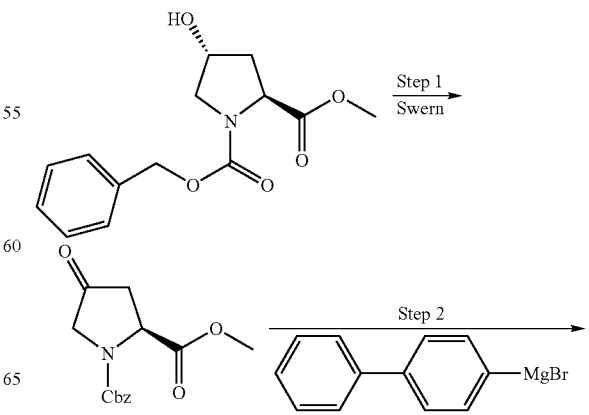

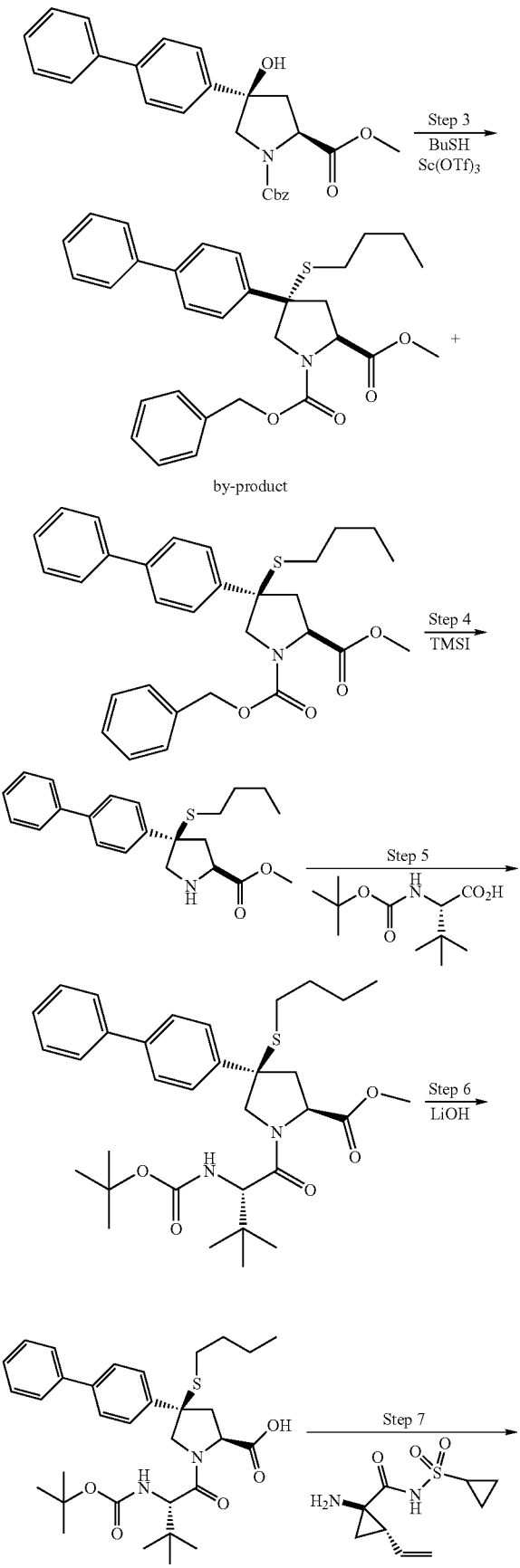

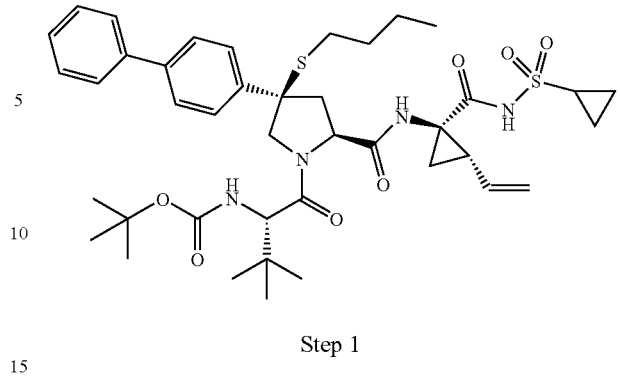

Step 1

To solution of methyl sulfoxide (28.0 ml, 395 mmol) in DCM (150 ml) at −78° C. was added oxalyl chloride (99 ml, 198 mmol) dropwise. The formed solution was stirred at this temperature for 30 min. A solution of (2S,4R)-1-benzyl 2-methyl 4-hydroxypyrrolidine-1,2-dicarboxylate (25.08 g, 90 mmol) in DCM (150 ml) was added dropwise at −78° C. The formed white slurry was stirred at −78° C. for 2 hr before addition of N,N-diisopropylethylamine (78 ml, 449 mmol) dropwise. The final pink solution was stirred at room temperature for 3 h. Washed with iced 1M HCl, 5% citric acid, and brine, dried over MgSO₄, filtered, evaporated. The residual light brown oil was purified by column, eluted with 4:1, 3:1, then 2:1 hexane-EtOAc to afford the desired product (17.8 g, 72% yield) as light brown viscous oil. $^1$H NMR (CDCl₃) δ 2.58-2.63 (m, 1H), 2.90-2.99 (m, 1H), 3.62, 3.77 (s, 3H, rotamers), 3.95-4.02 (m, 2H), 4.82-4.89 (m, 1H), 5.11-5.24 (m, 2H), 7.32-7.39 (m, 5H).

Step 2

To a solution of (S)-1-benzyl 2-methyl 4-oxopyrrolidine-1,2-dicarboxylate (13.24 g, 47.8 mmol) in toluene (400 mL) at 0° C. was added biphenyl-4-ylmagnesium bromide (124 mL, 62.1 mmol) dropwise. The formed light yellow solution was stirred at this temperature for 1 h. Quenched with NH4Cl, separated the organic layer. The aqueous was extracted with EtOAc. Washed the combined organic layers with brine, dried over MgSO₄, filtered, evaporated. The residue was purified by passing through silica gel plug, eluted with 4:1, 3:1 then 2:1, and finally 3:2 hexane-EtOAc to provide 10.50 g white solid, which was recrystallized from EtOAc-Hexane (50 ml-150 ml) to afford 7.50 g of the desired product as a small pink needle. The mother liquor was concentrated and purified by BIOTAGE® column, eluted with 5%~50% EtOAc-hexane to yield additional 1.89 g of the desired product. $^1$H NMR (CDCl₃) δ 2.39-2.45 (m, 1H), 2.70-2.75 (m, 1H), 3.66, 3.86 (s, 3H, rotamers), 3.80-3.90 (m, 1H), 4.00-4.07 (m, 1H), 4.62 (dd, $J_{1,2}$=9.5, 28 Hz, 1H), 5.09-5.15 (m, 1H), 5.21-5.25 (m, 1H), 7.31-7.38 (m, 6H), 7.42-7.45 (m, 2H), 7.54-7.59 (m, 6H); LC-MS (retention time: 2.77 min, method B), MS m/z 414 (M$^+$−H₂O), 370 (M$^+$−H₂O—CO₂).

Step 3

To a clear solution of (2S,4R)-1-benzyl 2-methyl 4-(biphenyl-4-yl)-4-hydroxypyrrolidine-1,2-dicarboxylate (2.59 g, 6 mmol) and 1-butanethiol (0.773 mL, 7.20 mmol) in acetonitrile (30 mL) was added Scandium(III) trifluoromethanesulfonate (0.295 g, 0.600 mmol) as solid by one portion at room temperature. The formed pink solution was stirred at this temperature for 26 h. TLC analysis showed starting material was completely consumed. Quenched with sat. ammonium chloride, extracted with EtOAc. Washed the organic with brine, dried over MgSO$_4$, filtered, evaporated in vacuo. The residue was purified by BIOTAGE® column, eluted with gradient 5~40% EtOAc-hexane to afford the mixture of diastereomers 2.54 g (84%). This oily mixture was purified by BIOTAGE® again, eluted with gradient 0~20% EtOAc-toluene. The first peak collected from the column afforded by-product (2S,4S)-1-benzyl 2-methyl 4-(biphenyl-4-yl)-4-(butylthio)pyrrolidine-1,2-dicarboxylate (1.54 g, 2.60 mmol, 43.3% yield) as a wax. $^1$H NMR (500 MHz, CHLOROFORM-d) δppm 0.77 (t, J=7.17, 3H), 1.21-1.24 (m, 2H), 1.28-1.34 (m, 2H), 2.20-2.29 (m, 2H), 2.41-2.46 (m, 1H), 2.86 (dd, J=12.82, 7.32 Hz, 1H), 3.53, 3.75 (s, rotomer, 3H), 3.89 (dd, J=17.09, 11.29 Hz, 1H), 4.23-4.36 (m, 1H), 4.69-4.77 (m, 1H) 5.22-5.30 (m, 2H) 7.28-7.44 (m, 10H), 7.53-7.60 (m, 4H). LC-MS (retention time: 3.28 min, method B), MS m/z 504 (M+H).

The desired product (2S,4R)-1-benzyl 2-methyl 4-(biphenyl-4-yl)-4-(butylthio)pyrrolidine-1,2-dicarboxylate (0.96 g, 1.620 mmol, 27.0% yield) was collected as the second peak from the column as a wax. $^1$H NMR (500 MHz, CHLOROFORM-d) δ ppm 0.77 (t, J=7.17, 3H), 1.18-1.26 (m, 2H), 1.27-1.35 (m, 2H), 2.15-2.24 (m, 2H), 2.64-2.73 (m, 1H), 2.76-2.84 (m, 1H), 3.61, 3.77 (s, rotomer, 3H), 3.93-3.95 (m, 1H), 4.16-4.30 (m, 1H), 4.35-4.45 (m, 1H), 5.03-5.15 (m, 1H), 5.22 (dd, J=16.02-12.36 Hz, 1H), 7.25-7.41 (m, 3H), 7.33-7.39 (m, 4H), 7.41-7.46 (m, 3H), 7.51-7.60 (m, 4H). LC-MS (retention time: 3.28 min, method B), MS m/z 504 (M+H).

Step 4

To an iced solution of (2S,4R)-1-benzyl 2-methyl 4-(biphenyl-4-yl)-4-(butylthio)pyrrolidine-1,2-dicarboxylate (1.19 g, 2.363 mmol) in Acetonitrile (20 mL) was added Iodotrimethylsilane (0.404 mL, 2.84 mmol). The formed light brown solution was stirred at room temperature for 2 h. Cooled with ice bath, quenched with thiophenol (0.314 mL, 3.07 mmol) and sat. ammonium chloride, extracted with EtOAc. The organic layer was washed with brine, dried over MgSO$_4$, filtered. The filtrate was treated with hydrochloric acid (3.54 mL, 7.09 mmol) and evaporated in vacuo. The residual oil was triturated with ether, decanted the ether layer. The remaining gum was pumped to dryness to afford the desired product (2S,4R)-methyl 4-(biphenyl-4-yl)-4-(butylthio)pyrrolidine-2-carboxylate, HCl (952 mg, 1.876 mmol, 79% yield) as a light yellow solid. $^1$H NMR (500 MHz, MeOD) δppm 0.78 (t, J=7.22 Hz, 3H), 1.23-1.32 (m, 4H), 2.33 (dt, J=11.67, 7.13 Hz, 1H), 2.37-2.43 (m, 1H), 2.98 (dd, J=14.19, 10.22 Hz, 1H), 3.13 (dd, J=14.04, 1.83 Hz, 1H), 3.81 (d, J=11.90 Hz, 1H), 3.96 (s, 3H), 4.02 (d, J=1.90 Hz, 1H), 4.79 (dd, J=10.38, 2.75 Hz, 1H), 7.38 (m, 1H), 7.44-7.52 (m, 4H), 7.63-7.71 (m, 4H). LC-MS (retention time: 2.27 min, method B), MS m/z 370 (M+H).

Step 5

To an iced slurry of (2S,4R)-methyl 4-(biphenyl-4-yl)-4-(butylthio)pyrrolidine-2-carboxylate, HCl (700 mg, 1.724 mmol), (S)-2-(tert-butoxycarbonylamino)-3,3-dimethylbutanoic acid (439 mg, 1.897 mmol), and HATU (983 mg, 2.586 mmol) in DCM (20 mL) was added N,N-diisopropylethylamine (0.903 mL, 5.17 mmol). The formed colorless slurry was stirred at room temperature for 5 h (it became light brown solution). Diluted with DCM, quenched with 5% citric acid. The organic layer was washed with 0.1 M NaOH and brine, dried over MgSO$_4$, filtered, evaporated in vacuo. The residue was purified by BIOTAGE® column, eluted with 5~35% etOAc-Hexane to yield a white foam. TLC analysis (toluene-EtOAc) showed there was still small amount of the undesired by product in it. Therefore, purification by BIOTAGE® column, eluted with 5~25% EtOAc-toluene was carried out to yield the desired product (2S,4R)-methyl 4-(biphenyl-4-yl)-1-((S)-2-(tert-butoxycarbonylamino)-3,3-dimethylbutanoyl)-4-(butylthio)pyrrolidine-2-carboxylate (600 mg, 0.875 mmol, 50.8% yield) as a white foam. $^1$H NMR (500 MHz, MeOD) δppm 0.78 (t, J=7.22 Hz, 3H), 1.12 (s, 9H), 1.24-1.33 (m, 2H), 1.32-1.40 (m, 2H), 1.47 (s, 9H), 2.22-2.40 (m, 2H), 2.56 (dd, J=12.82, 7.32 Hz, 1H), 2.92 (dd, J=12.97, 7.78 Hz, 1H), 3.74 (s, 3H), 4.09 (d, J=10.99 Hz, 1H), 4.36 (t, J=7.48 Hz, 1H), 4.41-4.51 (m, 1H), 4.76 (d, J=10.99 Hz, 1H), 7.36 (t, J=7.32 Hz, 1H), 7.45 (t, J=7.63 Hz, 3H), 7.52-7.73 (m, 5H). LC-MS (retention time: 3.63 min, method B), MS m/z 583 (M+H).

Step 6

To a solution of (2S,4R)-methyl 4-(biphenyl-4-yl)-1-((S)-2-(tert-butoxycarbonylamino)-3,3-dimethylbutanoyl)-4-(butylthio)pyrrolidine-2-carboxylate (430 mg, 0.738 mmol) in THF (4 mL) and MeOH (4.00 mL) was added pre-made solution of lithium hydroxide monohydrate (61.9 mg, 1.476 mmol) in water (4 mL). The formed cloudy solution was stirred at room temperature for 5 h. Quenched with 5% citric acid, extracted with EtOAc. The organic layer was washed with brine, dried over MgSO$_4$, filtered, evaporated, to afford the desired product (2S,4R)-4-(biphenyl-4-yl)-1-((S)-2-(tert-butoxycarbonylamino)-3,3-dimethylbutanoyl)-4-(butylthio)pyrrolidine-2-carboxylic acid (409 mg, 0.611 mmol, 83% yield) as a white foam. LC-MS (retention time: 3.49 min, method B), MS m/z 569 (M+H).

Step 7

To an iced slurry of (2S,4R)-4-(biphenyl-4-yl)-1-((S)-2-(tert-butoxycarbonylamino)-3,3-dimethylbutanoyl)-4-(butylthio)pyrrolidine-2-carboxylic acid (60 mg, 0.105 mmol), (1R,2S)-1-amino-N-(cyclopropylsulfonyl)-2-vinylcyclopropanecarboxamide, p-toluenesulfonate salt, H$_2$O (53.1 mg, 0.127 mmol), and HATU (60.1 mg, 0.158 mmol) in DCM (2 mL) was added N,N-diisopropylethylamine (0.055 mL, 0.316 mmol). The formed colorless slurry was stirred at room temperature for 5 h (it became light yellow solution). Diluted with DCM, quenched with 5% citric acid. The separated organic layer was washed with sat. sodium citrate and brine, dried over MgSO$_4$, filtered, evaporated in vacuo. The residue was purified by BIOTAGE® column, eluted with gradient 5%-40% acetone-hexane to yield the desired product tert-butyl (S)-1-((2S,4R)-4-(biphenyl-4-yl)-4-(butylthio)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylcarbamate (69 mg, 0.082 mmol, 78% yield) as a white solid. $^1$H NMR (500 MHz, MeOD) δppm 0.83 (t, J=7.32 Hz, 3H), 1.03-1.12 (m, 10H), 1.19-1.36 (m, 4H), 1.35-1.49 (m, 4H), 1.48 (s, 9H), 1.88 (s, J=7.93, 5.49 Hz, 3H), 2.14-2.24 (m, 1H), 2.23-2.30 (m, 1H), 2.35 (t, J=11.60 Hz, 1H), 2.39-2.53 (m, 1H), 2.76-2.87 (m, 1H), 2.89-3.00 (m, 1H), 3.93 (dd, J=10.68, 641 Hz, 1H), 3.99 (d, J=10.99 Hz, 1H), 4.51 (d, J=10.07 Hz, 1H), 5.06 (d, J=10.99 Hz, 1H), 5.10-5.19 (m, 1H), 5.29 (d, J=17.09 Hz, 1H), 5.69-5.83 (m, 1H), 7.37 (t, J=7.32 Hz, 1H), 7.46 (t, J=7.78 Hz, 2H), 7.55-7.63 (m, 4H) 7.64-7.77 (m, 2H). LC-MS (retention time: 3.48 min, method B), MS m/z 781 (M+H).

Example 2

Compound 2

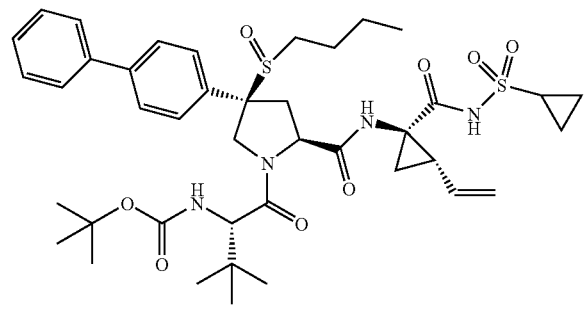

Compound 2

Scheme 2

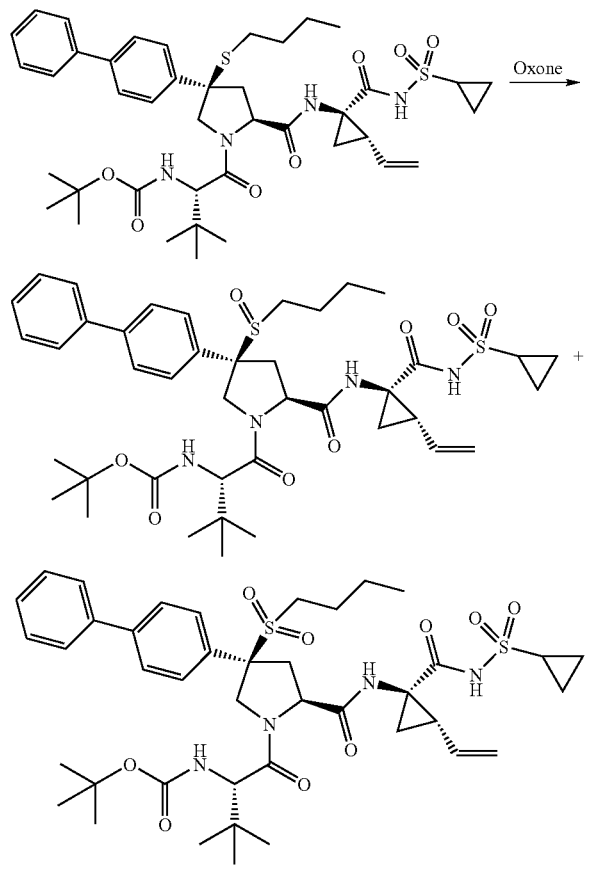

To a solution of tert-butyl (S)-1-((2S,4R)-4-(biphenyl-4-yl)-4-(butylthio)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylcarbamate (25 mg, 0.032 mmol) in MeOH (2 mL) was added pre-made solution of potassium peroxomonosulfate compound (89 mg, 0.144 mmol) in water (4 mL). The formed slurry was stirred at room temperature overnight. Quenched with 5% citric acid, extracted with EtOAc. Washed the organic with brine, dried over MgSO$_4$, filtered, evaporated in vacuo. The residue was purified by prep-HPLC. The first peak collected from the prep-HPLC column afforded tert-butyl (S)-1-((2S,4R)-4-(biphenyl-4-yl)-4-((R)-butylsulfinyl)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylcarbamate (2.3 mg, 2.89 µmol, 9.02% yield) and tert-butyl (S)-1-((2S,4R)-4-(biphenyl-4-yl)-4-(butylsulfonyl)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylcarbamate (1.9 mg, 2.337 µmol, 7.30% yield) as white solid. $^1$H NMR (500 MHz, MeOD) δ ppm 0.86 (t, J=7.48 Hz, 3H), 1.01-1.16 (m, 12H), 1.20-1.29 (m, 2H), 1.28-1.48 (m, 3H), 1.54 (s, 9H), 1.66-1.71 (m, 1H), 1.87 (dd, J=7.93, 5.49 Hz, 1H), 2.17-2.22 (m, 1H), 2.35-2.42 (m, 1H), 2.46-2.53 (m, 1H), 2.74-2.83 (m, 2H), 2.92-2.97 (m, 1H), 3.97-4.13 (m, 1H), 4.35 (d, J=10.99 Hz, 1H), 4.50-4.61 (m, 1H), 4.98 (d, J=10.99 Hz, 1H), 5.12 (d, J=10.38 Hz, 1H), 5.28 (d, J=17.09 Hz, 1H), 5.74-5.81 (m, 1H), 7.40 (t, J=7.17 Hz, 1H), 7.48 (t, J=7.63 Hz, 2H), 7.61 (d, J=7.63 Hz, 2H), 7.66-7.82 (m, 4H). LC-MS (retention time: 3.22 min, method B), MS m/z 797 (M+H).

Example 3

Compound 3

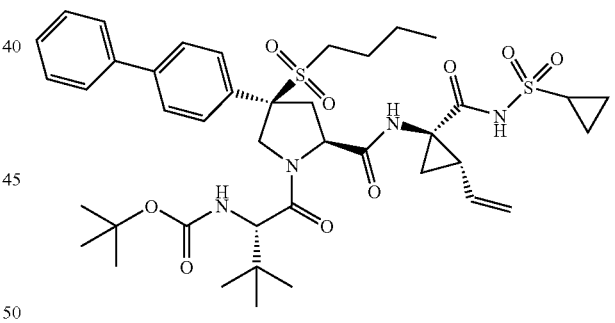

Compound 3

Compound 3, tert-butyl (S)-1-((2S,4R)-4-(biphenyl-4-yl)-4-(butylsulfonyl)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylcarbamate (1.9 mg, 2.337 µmol, 7.30% yield) was also obtained from Scheme 2 during HPLC separation process by collecting the second peak from the column as white solid. $^1$H NMR (500 MHz, MeOD) δ ppm 0.87 (t, J=7.32 Hz, 3H), 0.98-1.14 (m, 11H), 1.19-1.29 (m, 2H), 1.29-1.43 (m, 3H), 1.49 (s, 9H), 1.51-1.74 (m, 2H), 1.90 (dd, J=8.24, 5.49 Hz, 1H), 2.24 (q, J=8.85 Hz, 1H), 2.69-2.84 (m, 1H), 2.84-3.00 (m, 3H), 3.11 (dd, J=12.82, 6.41 Hz, 1H), 3.99 (dd, J=10.83, 6.56 Hz, 1H), 4.37 (d, J=10.99 Hz, 1H), 4.50 (d, J=9.77 Hz, 1H), 5.06-5.24 (m, 2H), 5.31 (dd, J=17.09, 1.22 Hz, 1H), 5.71-5.85 (m, 1H), 7.40 (t, J=7.32 Hz, 1H), 7.49 (t J=7.63 Hz, 2H), 7.63 (d, J=7.32 Hz, 2H), 7.73 (d, J=8.55 Hz, 2H), 7.91 (d, J=8.55 Hz, 2H). LC-MS (retention time: 3.51 min, method B), MS m/z 813 (M+H).

Example 4

Compound 4

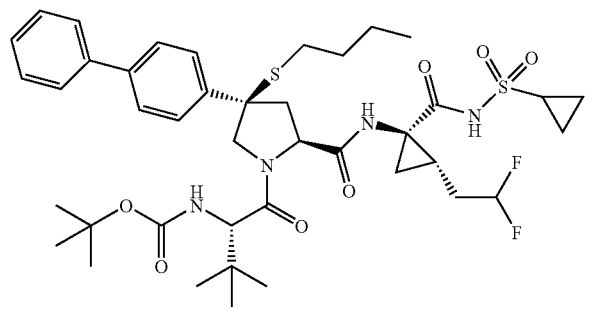

Compound 4

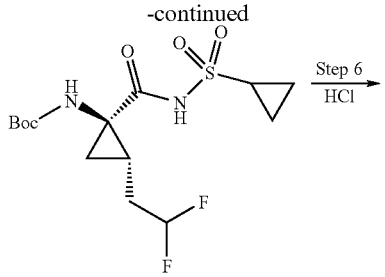

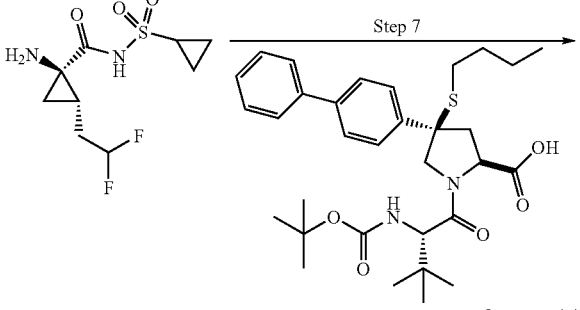

Compound 4

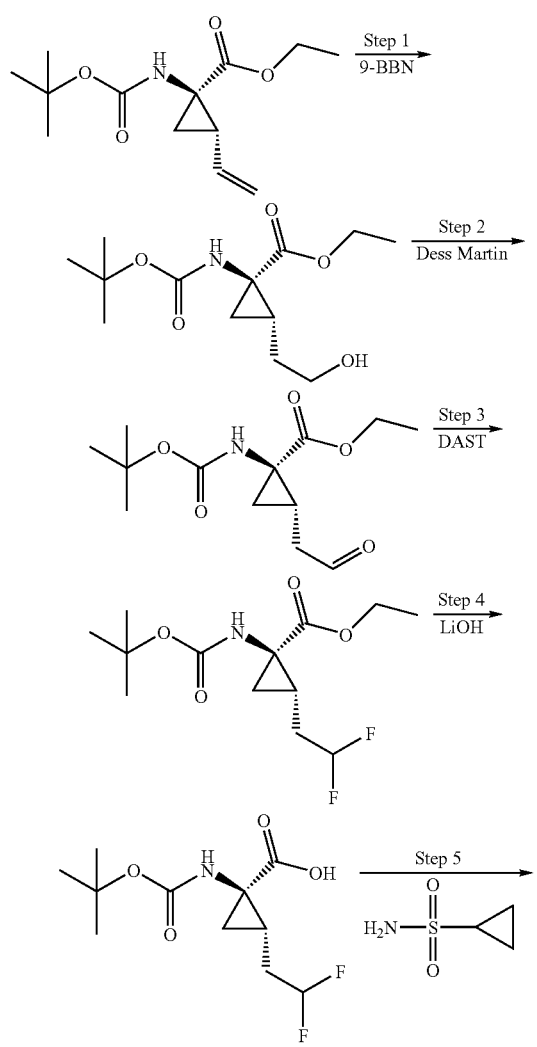

Scheme 3

Step 1

To a solution of (1R,2S)-ethyl 1-(tert-butoxycarbonylamino)-2-vinylcyclopropanecarboxylate (15.3 g, 59.9 mmol) in THF (100 ml) was added 9-BBN (180 ml, 90 mmol) dropwise at 0° C. The formed solution was stirred at room temperature for 2 hr. The final solution was cooled back to 0° C. while 3 M acetic acid, sodium salt (180 ml, 540 mmol) was added. To this well stirred mixture, hydrogen peroxide (89 ml, 869 mmol) was added dropwise (Caution should be exercised since the addition was exothermic). The formed warm two layer mixture was stirred overnight. Separated the upper organic layer. The aqueous layer was extracted with EtOAc. The combined organic layers were washed with brine. Dried over MgSO₄, filtered, evaporated. The residue was purified by silica gel column, eluted with 4:1, 3:1, 2:1, then 3:2 Hexane-EtOAc to afford the desired product (1R,2S)-ethyl 1-(tert-butoxycarbonylamino)-2-(2-hydroxyethyl)cyclopropanecarboxylate (11.50 g, 42.1 mmol, 70.2% yield) as a viscous oil, which solidified upon standing on the bench. $^1$H NMR (CDCl$_3$) δ 1.18-1.21 (m, 1H), 1.25 (t, J=7 Hz, 3H), 1.35-1.40 (m, 1H), 1.44 (s, 9H), 1.61-1.65 (m, 1H), 1.70-1.75 (m 1H), 1.91-1.98 (m, 1H), 3.61-3.65 (m, 1H), 3.71-3.75 (m, 1H), 4.10-4.21 (m, 2H), 5.17 (b, 1H).

Step 2

To a solution of (1R,2S)-ethyl 1-(tert-butoxycarbonylamino)-2-(2-hydroxyethyl)cyclopropanecarboxylate (1.37 g, 5.01 mmol) in DCM (50 ml) at 0° C. was added Dess-Martin periodinane (2.55 g, 6.01 mmol). The formed slurry was stirred at room temperature overnight. Filtered through CELITE®. The filtrated was concentrated and filtered again. The filtrate was transferred on a silica gel column, eluted with 2:1 hexane-EtOAc to afford the desired product (1.01 g, 74% yield) as a colorless oil, which solidified upon standing on the bench. $^1$H NMR (CDCl$_3$) δ 1.24 (t, J=7 Hz, 3H), 1.40-1.45 (m, 11H), 1.65-1.69 (m, 1H), 2.75-2.80 (m, 2H), 4.09-4.19 (m, 2H), 5.17 (b, 1H), 9.76 (s, 1H).

Step 3

To a solution of (1R,2S)-ethyl 1-(tert-butoxycarbonylamino)-2-(2-oxoethyl)cyclopropanecarboxylate (862 mg, 3.18 mmol) in DCM (30 ml) at 0° C. was added (diethylamino)sulfur trifluoride (0.840 ml, 6.35 mmol). The formed slurry was stirred at room temperature overnight. Quenched with conc. ammonia chloride, extracted with EtOAc. The organic layer was washed with brine, dried over MgSO$_4$, evaporated. The residue was transferred on a silica gel column, eluted with 4:1 then 2:1 hexane-EtOAc to afford the desired product (210 mg, 22% yield) as a light yellow oil. 300 mg of starting material was also recovered after column separation. $^1$H NMR (CDCl$_3$) δ 1.26 (t, J=7 Hz, 3H), 1.35-1.39 (m, 1H), 1.44 (s, 9H), 1.46-1.50 (m, 1H), 1.55-1.60 (m, 1H), 2.18-2.24 (m, 2H), 4.15-4.21 (m, 2H), 5.17 (b, 1H), 5.73, 5.85, 5.99 (b, 1H).

Step 4

To a solution of (1R,2S)-ethyl 1-(tert-butoxycarbonylamino)-2-(2,2-difluoroethyl)cyclopropanecarboxylate (210 mg, 0.716 mmol) in THF (2 ml) and MeOH (2.000 ml) at 25° C. was added pre-made solution of Lithium hydroxide monohydrate (0.040 ml, 1.432 mmol) in water (2 ml). The formed cloudy suspension was stirred at room temperature overnight. Removed the volatiles in vacuo. Diluted with 5% citric acid, extracted with EtOAc. The organic layer was washed with brine, dried over MgSO$_4$. The residue was pumped overnight to afford the desired product (172 mg, 91% yield) as off-white solid and was used as crude. $^1$H NMR (CD$_3$OD) δ 1.25-1.28 (m, 1H), 1.42-1.43 (m, 10H), 1.46-1.53 (m, 1H), 2.12-2.14 (m, 2H), 4.15-4.21 (m, 2H), 5.73, 5.85, 6.00 (b, 1H).

Step 5

To a solution of (1R,2S)-1-(tert-butoxycarbonylamino)-2-(2,2-difluoroethyl)cyclopropanecarboxylic acid (1.50 g, 5.6 mmol) in THF (50 ml) was added CDI (1.14 g, 7.0 mmol) at room temperature. The resulting solution was stirred at this temperature for 3 h. Cyclopropanesulfonamide (1.37 g, 11.2 mmol) and DBU (1.65 ml, 11.2 mmol) were added sequentially. The final mixture was stirred at room temperature overnight. Diluted with EtOAc, extracted with 5% citric acid. The organic layer was washed with brine, dried over MgSO$_4$, evaporated. The residue was transferred on a silica gel column, eluted with 1-5% iPrOH/CHCl$_3$ to afford the desired product (1.20 g, 58% yield) as an off-white solid. $^1$H NMR (CDCl$_3$) δ 1.08-1.10 (m, 2H), 1.28-1.35 (m, 2H), 1.45-1.46 (m, 1H), 1.47 (s, 9H), 1.60-1.65 (m, 1H), 1.70-1.71 (m, 1H), 2.07-2.15 (m, 2H), 2.92-2.94 (m, 1H), 5.16 (b, 1H), 5.79, 5.89, 6.02 (b, 1H), 9.35 (b, 1H). LC-MS (retention time: 0.1.80 min, method B), MS m/z 369 (M$^+$+H).

Step 6

To a solution of tert-butyl (1R,2S)-1-(cyclopropylsulfonylcarbamoyl)-2-(2,2-difluoroethyl)cyclopropylcarbamate (55 mg, 0.149 mmol) in 1,4-dioxane (1.3 ml) was added 4M HCl (0.746 ml, 2.99 mmol) in 1,4-dioxane. The formed solution was stirred at 25° C. for 3 h. LC/MS analysis showed the starting material was completely converted into the desired product. Removed the solvent in vacuo. The residue was pumped overnight and was used for the next reaction without further purification. LC-MS (retention time: 0.38 min, method B), MS m/z 269 (M$^+$+H).

Step 7

To a solution of (2S,4R)-4-(biphenyl-4-yl)-1-((S)-2-(tert-butoxycarbonylamino)-3,3-dimethylbutanoyl)-4-(butylthio)pyrrolidine-2-carboxylic acid (15 mg, 0.026 mmol), (1R,2S)-1-amino-N-(cyclopropylsulfonyl)-2-(2,2-difluoroethyl)cyclopropanecarboxamide (8.84 mg, 0.029 mmol), and HATU (15.03 mg, 0.040 mmol) in DMF (1 mL) was added N,N-Diisopropylethylamine (0.014 mL, 0.079 mmol). The formed light yellow solution was stirred at room temperature for 5 h. Diluted with MeOH, purified by prep-HPLC to yield the desired product tert-butyl (S)-1-((2S,4R)-4-(biphenyl-4-yl)-4-(butylthio)-2-((1R,2S)-1-(cyclopropylsulfonylcarbamoyl)-2-(2,2-difluoroethyl)cyclopropylcarbamoyl)pyrrolidin-1-yl)-3,3-dimethyl-1-oxobutan-2-ylcarbamate (14 mg, 0.015 mmol, 58.3% yield) as a white solid. $^1$H NMR (500 MHz, MeOD) δppm 0.83 (t, J=7.17 Hz, 3H), 1.09-1.12 (m, 10H), 1.22-1.45 (m, 7H) 1.47-1.52 (m, 10H), 1.66 (s, 2H), 2.07-2.38 (m, 4H), 2.37-2.51 (m, 1H), 2.76-2.87 (m, 1H), 2.91-3.04 (m, 11H), 3.85-4.06 (m, 2H), 4.51 (d, J=9.77 Hz, 1H), 5.05 (d, J=11.29 Hz, 1H), 5.73-6.09 (m, 1H), 7.37 (t, J=7.02 Hz, 1H), 7.46 (t, J=7.48 Hz, 2H), 7.54-7.64 (m, 4H), 7.68 (d, J=8.24 Hz, 2H). LC-MS (retention time: 3.48 min, method B), MS m/z 819 (M+H).

Example 5

Compound 5

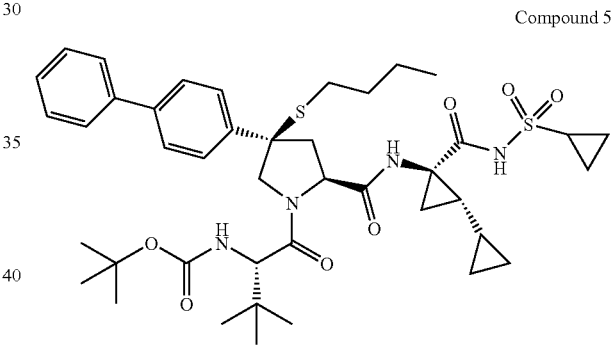

Compound 5

To a solution of (2S,4R)-4-(biphenyl-4-yl)-1-((S)-2-(tert-butoxycarbonylamino)-3,3-dimethylbutanoyl)-4-(butylthio)pyrrolidine-2-carboxylic acid (14 mg, 0.025 mmol), (1S,2R)-2-amino-N-(cyclopropylsulfonyl)bi(cyclopropane)-2-carboxamide, HCl (7.60 mg, 0.027 mmol), and HATU (14.03 mg, 0.037 mmol) in DMF (1 mL) was added N,N-diisopropylethylamine (0.013 mL, 0.074 mmol). The formed light yellow solution was stirred at room temperature overnight. Diluted with MeOH, purified by prep-HPLC to yield the desired product tert-butyl (S)-1-((2S,4R)-4-(biphenyl-4-yl)-4-(butylthio)-2-((1S,2R)-2-(cyclopropylsulfonylcarbamoyl)bi(cyclopropan)-2-ylcarbamoyl)pyrrolidin-1-yl)-3,3-dimethyl-1-oxobutan-2-ylcarbamate (6 mg, 7.02 μmol, 28.5% yield) as a white solid and recovered about 30% starting material as well. $^1$H NMR (500 MHz, MeOD) δppm 0.25-0.35 (m, 2H), 0.47-0.55 (m, 1H), 0.55-0.64 (m, 1H), 0.79-0.87 (m, 3H), 1.02-1.14 (m, 1H), 1.19-1.50 (m, 9H), 1.50-1.55 (m, 9H), 1.76 (dd, J=8.24, 5.49 Hz, 1H), 2.16-2.37 (m, 2H), 2.37-2.51 (m, 1H), 2.79 (dd, J=12.05, 6.26 Hz, 1H), 2.92-3.03 (m, 1H), 3.91 (dd, J=10.68, 6.41 Hz, 1H), 3.98 (d, J=10.99 Hz, 1H), 4.50 (d, J=9.77 Hz, 1H), 5.05 (d, J=10.99 Hz, 1H), 7.37 (t, J=7.48 Hz, 1H), 7.46 (t, J=7.63 Hz, 2H), 7.55-7.63 (m, 4H), 7.64-7.75 (m, 2H). LC-MS (retention time: 3.57 min, method B), MS m/z 795 (M+H).

Example 6

Compound 6

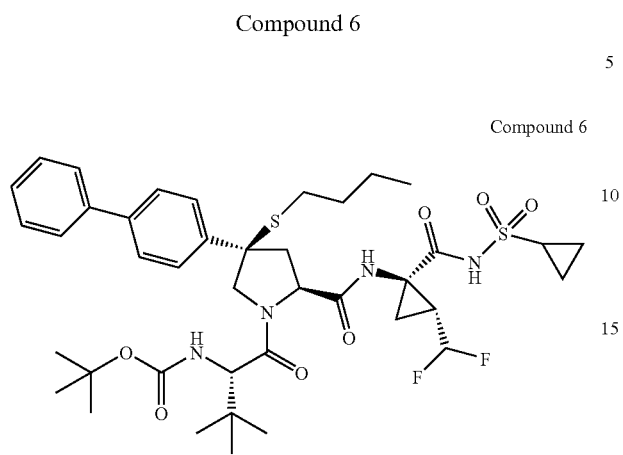

Compound 6

To a solution of (2S,4R)-4-(biphenyl-4-yl)-1-((S)-2-(tert-butoxycarbonylamino)-3,3-dimethylbutanoyl)-4-(butylthio)pyrrolidine-2-carboxylic acid (15 mg, 0.026 mmol), (1R,2R)-1-amino-N-(cyclopropylsulfonyl)-2-(difluoromethyl)cyclopropanecarboxamide, HCl (7.67 mg, 0.026 mmol), and HATU (15.03 mg, 0.040 mmol) in DMF (1 mL) was added N,N-Diisopropylethylamine (0.014 mL, 0.079 mmol). The formed light yellow solution was stirred at room temperature overnight. Diluted with MeOH, purified by prep-HPLC to yield the desired product tert-butyl (S)-1-(((2S,4R)-4-(biphenyl-4-yl)-4-(butylthio)-2-(((1R,2R)-1-(cyclopropylsulfonylcarbamoyl)-2-(difluoromethyl)cyclopropylcarbamoyl)pyrrolidin-1-yl)-3,3-dimethyl-1-oxobutan-2-ylcarbamate (12 mg, 0.015 mmol, 56.5% yield) as a white solid. $^1$H NMR (500 MHz, MeOD) δppm 0.83 (t, J=7.02 Hz, 3H), 1.04-1.16 (m, 11H), 1.23-1.45 (m, 6H), 1.45-1.59 (m, 10H), 1.96-2.10 (m, 2H), 2.20-2.38 (m, 2H), 2.38-2.51 (m, 1H), 2.81 (dd, J=12.36, 6.26 Hz, 1H), 2.90-3.02 (m, 1H), 3.91 (dd, J=10.38, 6.41 Hz, 1H), 3.99 (d, J=10.99 Hz, 1H), 4.51 (d, J=9.77 Hz, 1H), 5.07 (d, J=10.99 Hz, 1H), 5.79-6.02 (m, 1H), 7.37 (t, J=7.02 Hz, 1H), 7.46 (t, J=7.48 Hz, 2H), 7.55-7.65 (m, 4H), 7.66-7.75 (m, 2H). LC-MS (retention time: 3.50 min, method B), MS m/z 805 (M+H).

Example 7

Compound 7

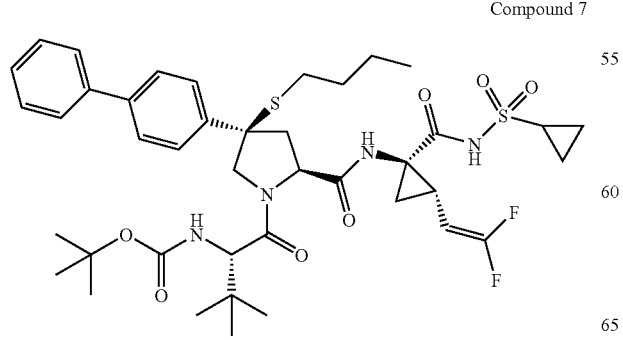

Compound 7

Scheme 4

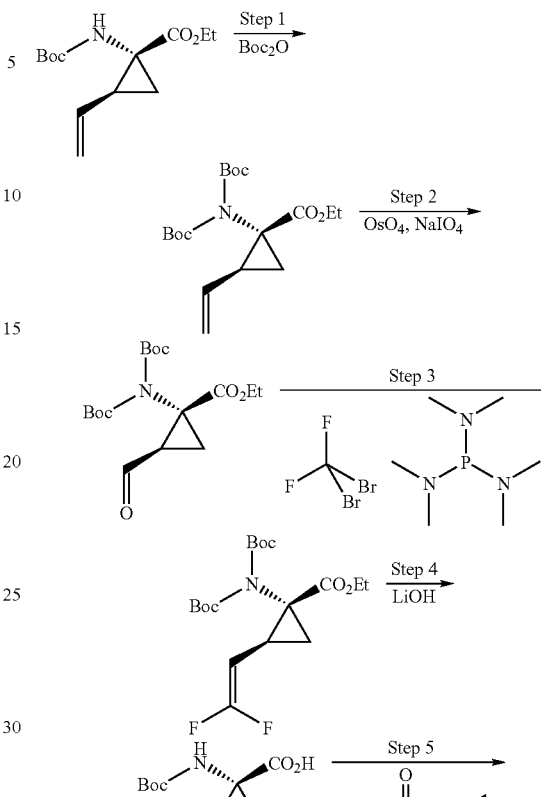

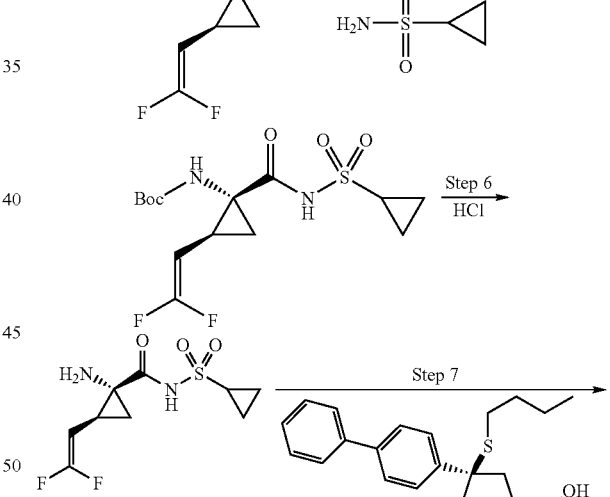

Compound 7

Step 1

A solution of (1R,2S)-ethyl 1-(tert-butoxycarbonylamino)-2-vinylcyclopropanecarboxylate (24 g, 94 mmol), BOC$_2$O (39.3 mL, 169 mmol), and DMAP (2.297 g, 18.80 mmol) in acetonitrile (200 μL) was heated to 65° C. overnight (when heating the reaction up carbon dioxide evolution begins around 50-60° C.). The reaction was then cooled, concentrated and purified on the BIOTAGE® (15-25% EtOAc/hexanes) to give the desired product as a lightly colored oil (32.6 g, 98%). $^1$H NMR (500 MHz, CHLOROFORM-d) ppm 1.24 (t, J=7.17 Hz, 3H) 1.38-1.56 (m, 19H) 1.89 (dd, J=8.70, 5.95 Hz, 1H) 2.26 (q, J=9.05 Hz, 1H) 4.08-4.28 (m, 2H) 5.15 (dd, J=10.38, 1.53 Hz, 1H) 5.28 (dd, J=17.24, 1.68 Hz, 1H) 5.87 (ddd, J=17.17, 10.15, 9.00 Hz, 1H).

Step 2

OsO$_4$ (4% wt in water) (1.7 mL, 0.281 mmol) was added to a solution of (1R,2S)-ethyl 1-(bis(tert-butoxycarbonyl)amino)-2-vinylcyclopropanecarboxylate (10 g, 28.1 mmol) in THF (50 mL) and t-butanol (500 mL) stirred with a mechanical stirrer at 0° C. To this was added a solution of NaIO$_4$ (15.04 g, 70.3 mmol) in water (40 mL). The reaction turned to a thick slurry of white precipitate. After 15 min. the ice bath was removed and the reaction allowed to warm to r.t. and stirred overnight. The reaction was filtered through CELITE® with EtOAc and then concentrated. The residue was taken up in EtOAc and washed with brine. The organics were dried, filtered and evaporated to give crude material. The crude was purified on the BIOTAGE® (15-20% EtOAc/hexanes) to give the desired product as a colorless oil (8.05 g, 80%). $^1$H NMR (300 MHz, CHLOROFORM-d) δ ppm 1.27 (t, J=7.14 Hz, 3H) 1.50 (s, 18H) 1.78 (dd, J=9.51, 6.22 Hz, 1H) 2.30 (td, J=9.06, 5.67 Hz, 1H) 2.48 (dd, J=8.42, 6.22 Hz, 1H) 4.16-4.33 (m, 2H) 9.47 (d, J=5.86 Hz, 1H).

Step 3

Hexamethylphosphorous triamide (16.42 mL, 90 mmol) was added slowly to a mixture of Dibromodifluoromethane (4.09 mL, 44.8 mmol) and 4A molecular sieves (2 g) in THF (100 ml) at −78° C. This was stirred for 30 min. at −78° C. (the mixture turned to a thick sludge) and then warmed to 0° C. (1R,2R)-ethyl 1-(bis(tert-butoxycarbonyl)amino)-2-formylcyclopropanecarboxylate (8 g, 22.38 mmol) in THF (30 mL) was added and stirring continued at 0° C. for 1 hr and then at r.t. for 1 hr. TLC analysis showed consumption of starting material. The reaction was diluted with ether and phosphate buffer (pH 7). The aqueous layer was extracted with ether and the combined organics were dried, filtered and evaporated to give crude (stinky) material. This was purified on the BIOTAGE® (5-15% EtOAc/hexanes) to give the desired product as a colorless oil (4.7 g, 54%). $^1$H NMR (300 MHz, CHLOROFORM-d) δ ppm 1.26 (t, J=7.14 Hz, 3H) 1.39-1.54 (m, 19H) 1.81 (dd, J=8.60, 6.04 Hz, 1H) 2.26 (q, J=9.51 Hz, 1H) 4.10-4.29 (m, 2H) 4.50 (ddd, J=24.88, 9.51, 1.83 Hz, 1H).

Step 4

2.0M LiOH (24 mL, 48.0 mmol) was added to a solution of (1R,2S)-ethyl 1-(bis tert-butoxycarbonyl(amino)-2-(2,2-difluorovinyl)cyclopropanecarboxylate (4.7 g, 12.01 mmol) in THF (50 mL) and MeOH (50 mL). This was stirred at r.t. overnight. The reaction was diluted with Et$_2$O and 1.0M HCl. The aqueous layer was extracted with Et$_2$O (2×) and the combined organics were dried, filtered and evaporated to give crude product. The crude was purified on the BIOTAGE® (5-20% acetone/hexanes) to give the desired product as a white foam (2.6 g, 82%). $^1$H NMR (300 MHz, DMSO-d$_6$) δ ppm 1.25-1.40 (m, 10H) 1.40-1.51 (m, 1H) 1.99 (q, J=8.78 Hz, 1H) 4.32-4.61 (m, 1H) 7.24 & 7.58 (NHBoc, 1H) 12.64 (br. s., 1H).

Step 5

((1R,2S)-1-(tert-Butoxycarbonylamino)-2-(2,2-difluorovinyl)cyclopropanecarboxylic acid (1.1 g, 4.18 mmol) and di(1H-imidazol-1-yl)methanone (0.813 g, 5.01 mmol) were dissolved in THF (30 ml) at rt, light yellow solution formed. Stirred for 2 hrs. Cyclopropanesulfonamide (0.861 g, 7.10 mmol)) was added to the solution followed by 2,3,4,6,7,8,9,10-octahydropyrimido[1,2-a]azepine (1.260 mL, 8.36 mmol). Stirred for 1 h at rt. Diluted with water-10 ml, cooled in an ice bath, acidified with 6N HCl to PH~1, extracted with ethyl acetate twice (2×10 mL). Dried over Na$_2$SO$_4$. The resulted brown solid was purified by silica, eluted with gradient 5-20% acetone/hexanes. 1.25 g (78%) of the desired product was obtained. $^1$H NMR (400 MHz, CHLOROFORM-d) δppm 9.44 (1H, br. s.), 5.26 (1H, m), 2.86-2.98 (1H, m), 2.09-2.20 (1H, m), 1.77-1.89 (1H, 1.38-1.49 (11H, m), 1.02-1.14 (2H, m).

Step 6

4.0M HCl in dioxane (25 mL, 100 mmol) was added to tert-butyl (1R,2S)-1-(cyclopropylsulfonylcarbamoyl)-2-(2,2-difluorovinyl)cyclopropylcarbamate (1.5 g, 4.09 mmol) and stirred at r.t. for 2 hrs. The reaction was concentrated and dried under vacuum to give the desired product as a lightly colored crunchy foam (1.20 g, 97%). LC-MS (retention time: 0.52 min, method B), MS m/z 267 (M+H).

Step 7

To an iced solution of (2S,4R)-4-(biphenyl-4-yl)-1-((S)-2-(tert-butoxycarbonylamino)-3,3-dimethylbutanoyl)-4-(butylthio)pyrrolidine-2-carboxylic acid (15 mg, 0.026 mmol), (1R,2S)-1-amino-N-(cyclopropylsulfonyl)-2-(2,2-difluorovinyl)cyclopropanecarboxamide, HCl (8.78 mg, 0.029 mmol), and HATU (15.04 mg, 0.040 mmol) in DMF was added N,N-Diisopropylethylamine (0.018 mL, 0.105 mmol). The formed light brown solution was stirred at room temperature overnight. Diluted with MeOH, purified by prep-HPLC to afford the desired product tert-butyl (S)-1-((2S,4R)-4-(biphenyl-4-yl)-4-(butylthio)-2-((1R,2S)-1-(cyclopropylsulfonylcarbamoyl)-2-(2,2-difluorovinyl)cyclopropylcarbamoyl)pyrrolidin-1-yl)-3,3-dimethyl-1-oxobutan-2-ylcarbamate (8 mg, 9.11 μmol, 34.5% yield) as a white solid. $^1$H NMR (500 MHz, MeOD) δ ppm 0.83 (t, J=7.17 Hz, 3H), 1.02-1.14 (m, 11H), 1.21-1.35 (m, 4H), 1.36-1.45 (m, 2H), 1.50 (s, 9H), 1.74-1.83 (m, 1H), 2.16-2.30 (m, 2H), 2.35 (t, J=11.44 Hz, 1H), 2.44 (dd, J=12.36, 6.56 Hz, 1H), 2.75-2.87 (m, 1H), 2.92-3.00 (m, 1H), 3.93 (dd, J=10.22, 6.26 Hz, 1H), 3.99 (d, J=10.99 Hz, 1H), 4.38-4.53 (m, 2H), 5.06 (d, J=10.99 Hz, 1H), 7.37 (t, J=6.87 Hz, 1H), 7.46 (t, J=7.63 Hz, 2H), 7.54-7.64 (m, 4H), 7.65-7.73 (m, 2H). LC-MS (retention time: 3.60 min, method B), MS m/z 817 (M+H).

Example 8
Compound 8
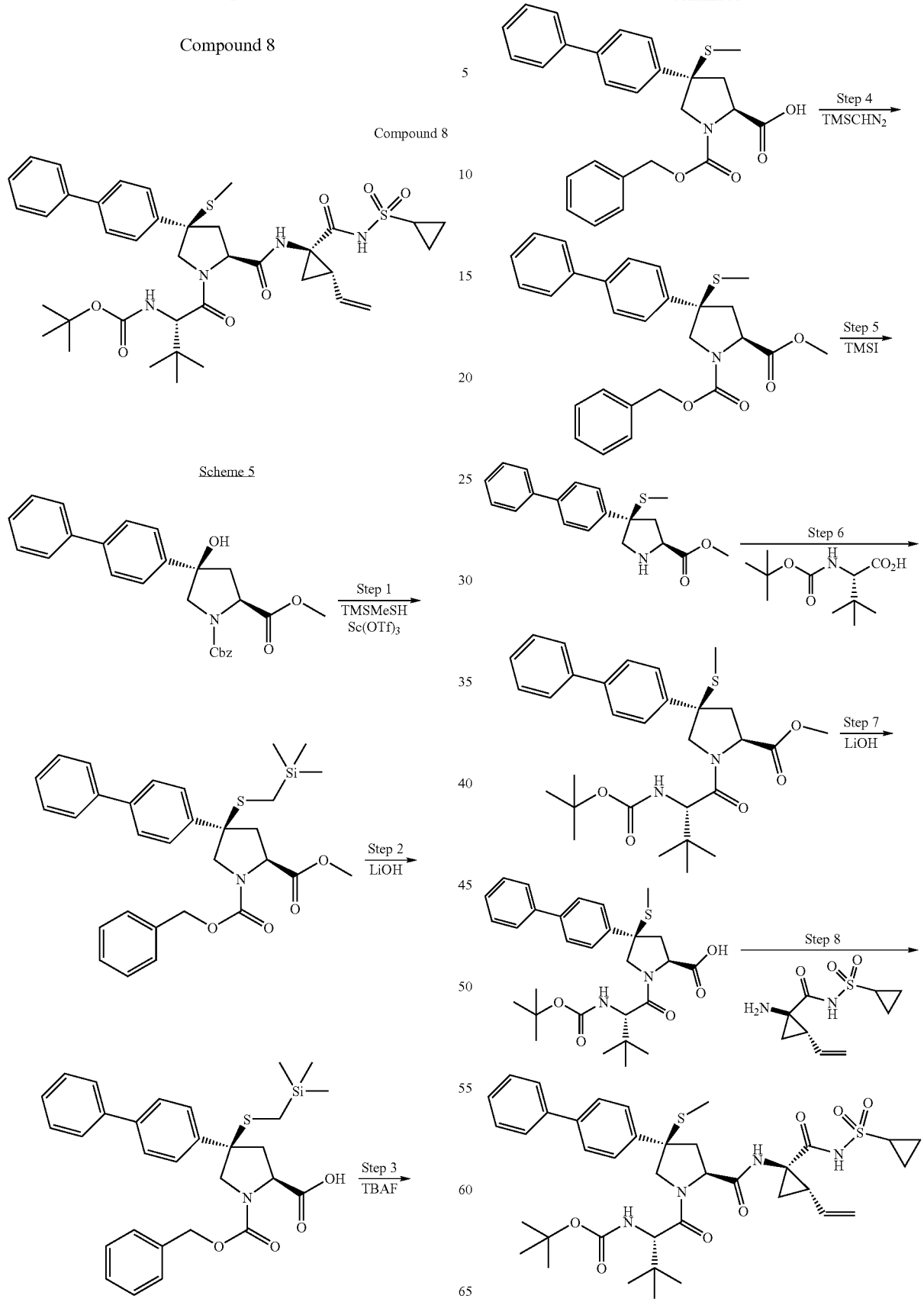
Scheme 5

Step 1

To a clear solution of (2S,4R)-1-benzyl 2-methyl 4-(biphenyl-4-yl)-4-hydroxypyrrolidine-1,2-dicarboxylate (2.59 g, 6.00 mmol) and trimethylsilylmethanethiol (1.019 mL, 7.20 mmol) in Acetonitrile (30 mL) was added Scandium(III) trifluoromethanesulfonate (0.295 g, 0.600 mmol) as solid by one portion at room temperature. The formed pink solution was stirred at this temperature for 26 h. TLC analysis showed starting material was completely consumed. Quenched with sat. ammonium chloride, extracted with EtOAc. Washed the organic with brine, dried over $MgSO_4$, filtered, evaporated in vacuo. The residue was purified by BIOTAGE® column, eluted with gradient 5~40% EtOAc-hexane to afford the mixture of diastereomers 3.10 g (97%). This oily mixture was purified by BIOTAGE® again, eluted with gradient 0~20% EtOAc-toluene to yield the by-product (2S,4S)-1-benzyl 2-methyl 4-(biphenyl-4-yl)-4-((trimethylsilyl)methylthio) pyrrolidine-1,2-dicarboxylate (1.40 g, 2.62 mmol, 43.7% yield) as a wax and the desired product (2S,4R)-1-benzyl 2-methyl 4-(biphenyl-4-yl)-4-((trimethylsilyl)methylthio) pyrrolidine-1,2-dicarboxylate (1.25 g, 2.108 mmol, 35.1% yield) as a white foam. $^1$H NMR (500 MHz, CHLOROFORM-d) δppm −0.03 (s, 9H), 1.33 (dd, J=28.08, 11.29 Hz, 1H), 1.49 (dd, J=17.70, 11.29 Hz, 1H), 2.62-2.85 (m, 2H), 3.62, 3.77 (s, 3H), 3.97 (t, J=11.60 Hz, 1H), 4.16 (dd, J=74.62, 11.44 Hz, 1H), 4.35-4.56 (m, 1H), 4.99-5.19 (m, 1H), 5.17-5.27 (m, 1H), 7.27-7.40 (m, 8H), 7.39-7.49 (m, 2H), 7.49-7.67 (m, 4H). LC-MS (retention time: 3.62 mm, method B), MS m/z 534 (M+H).

Step 2

To a solution of (2S,4R)-1-benzyl 2-methyl 4-(biphenyl-4-yl)-4-((trimethylsilyl)methylthio)pyrrolidine-1,2-dicarboxylate (472 mg, 0.884 mmol) in THF (10 mL) and MeOH (10 mL) was added premade solution of Lithium hydroxide monohydrate (74.2 mg, 1.769 mmol) in Water (10 mL). The formed white slurry was stirred at room temperature for 3 days. Quenched with 5% citric acid, extracted with EtOAc. The organic layer was washed with brine, dried over $MgSO_4$, filtered, evaporated to afford the desired product (2S,4R)-1-(benzyloxycarbonyl)-4-(biphenyl-4-yl)-4-((trimethylsilyl) methylthio)pyrrolidine-2-carboxylic acid (460 mg, 0.797 mmol, 90% yield) as a wax. This product was used for the next reaction without further purification. LC-MS (retention time: 3.43 min, method B), MS m/z 520 (M+H).

Step 3

To a solution of (2S,4R)-1-(benzyloxycarbonyl)-4-(biphenyl-4-yl)-4-((trimethylsilyl)methylthio)pyrrolidine-2-carboxylic acid (453 mg, 0.872 mmol) in THF (10 mL) was added Tetrabutylammonium fluoride (2.61 mL, 2.61 mmol). The formed light yellow solution was stirred at room temperature overnight. Diluted with EtOAc, washed with 5% citric acid, and brine, dried over $MgSO_4$, filtered, evaporated, to afford the desired product (2S,4R)-1-(benzyloxycarbonyl)-4-(biphenyl-4-yl)-4-(methylthio)pyrrolidine-2-carboxylic acid (390 mg, 0.784 mmol, 90% yield) as a white foam. LC-MS (retention time: 3.14 min, method B), MS m/z 448 (M+H), 400 (M-MeSH).

Step 4

To an iced colorless solution of (2S,4R)-1-(benzyloxycarbonyl)-4-(biphenyl-4-yl)-4-(methylthio)pyrrolidine-2-carboxylic acid (288 mg, 0.644 mmol) in MeOH (5 mL) was added (trimethylslyl)diazomethane (3.54 mL, 7.08 mmol) dropwise until it turned into light yellow (bubble was generated). The formed light yellow solution was stirred at room temperature overnight. Diluted with EtOAc, washed with 5% citric acid, and brine, dried over $MgSO_4$, filtered, evaporated, to afford the desired product (2S,4R)-1-benzyl 2-methyl 4-(biphenyl-4-yl)-4-(methylthio)pyrrolidine-1,2-dicarboxylate (267 mg, 0.578 mmol, 90% yield) as a white wax. LC-MS (retention time: 3.25 min, method B), MS m/z 462 (M+H), 414 (M-MeSH).

Step 5

To an iced solution of (2S,4R)-1-benzyl 2-methyl 4-(biphenyl-4-yl)-4-(methylthio)pyrrolidine-1,2-dicarboxylate (267 mg, 0.578 mmol) in acetonitrile (3 mL) was added iodotrimethylsilane (0.123 mL, 0.868 mmol). The formed light brown solution was stirred at room temperature for 2 h. Cooled with ice bath, quenched with MeOH. The final light brown solution was purified by prep-HPL, and the collected fractions were evaporated on speed-vac system to afford the desired product (2S,4R)-methyl 4-(biphenyl-4-yl)-4-(methylthio)pyrrolidine-2-carboxylate, TFA (174 mg, 0.355 mmol, 61.3% yield) as a light yellow solid. $^1$H NMR (500 MHz, MeOD) δ ppm 1.89 (s, 3H), 2.96 (dd, J=13.73, 10.68 Hz, 1H), 3.13 (d, J=14.04 Hz, 1H), 3.80 (d, J=11.90 Hz, 1H), 3.96 (s, 3H), 4.03 (d, J=11.90 Hz, 1H), 4.76-4.81 (m, 1H), 7.38 (t, J=7.48 Hz, 1H), 7.44-7.50 (m, 4H) 7.65 (d, J=8.24 Hz, 2H) 7.70 (d, J=7.63 Hz, 2H). LC-MS (retention time: 2.36 min, method B), MS m/z 328 (M+H).

Step 6

To an iced slurry of (2S,4R)-methyl 4-(biphenyl-4-yl)-4-(methylthio)pyrrolidine-2-carboxylate, TFA (174 mg, 0.394 mmol), (S)-2-(tert-butoxycarbonylamino)-3,3-dimethylbutanoic acid (100 mg, 0.434 mmol), and HATU (225 mg, 0.591 mmol) in DCM (5 mL) was added N,N-Diisopropylethylamine (0.207 mL, 1.182 mmol). The formed colorless slurry was stirred at room temperature overnight. Diluted with DCM, quenched with 5% citric acid. The organic layer was washed with 0.1 M NaOH and brine, dried over $MgSO_4$, filtered, evaporated in vacuo. The residue was purified by BIOTAGE® column, eluted with 5~35% etOAc-hexane to yield the desired product (2S,4R)-methyl 4-(biphenyl-4-yl)-1-((S)-2-(tert-butoxycarbonylamino)-3,3-dimethylbutanoyl)-4-(methylthio)pyrrolidine-2-carboxylate (178 mg, 0.296 mmol, 75% yield) as a white solid. $^1$H NMR (500 MHz, MeOD) δppm 1.12 (s, 9H), 1.46 (s, 9H), 1.86 (s, 3H), 2.60 (dd, J=12.97, 6.87 Hz, 1H), 2.90 (dd, J=12.82, 7.93 Hz, 1H), 3.74 (s, 3H), 4.11 (d, J=11.29 Hz, 1H), 4.35-4.48 (m, 2H), 4.73 (d, J=10.99 Hz, 1H), 7.36 (t, J=7.02 Hz, 1H), 7.42-7.51 (m, 3H), 7.54-7.71 (m, 5H). LC-MS (retention time: 3.34 min, method B), MS m/z 541 (M+H).

Step 7

To a solution of (2S,4R)-methyl 4-(biphenyl-4-yl)-1-((S)-2-(tert-butoxycarbonylamino)-3,3-dimethylbutanoyl)-4-(methylthio)pyrrolidine-2-carboxylate (164 mg, 0.303 mmol) in THF (2 mL) and MeOH (2.000 mL) was added pre-made solution of Lithium hydroxide monohydrate (25.5 mg, 0.607 mmol) in water (2 mL). The resulting cloudy solution was stirred at room temperature overnight. Quenched with 5% citric acid, extracted with EtOAc. The organic layer was washed with brine, dried over $MgSO_4$, filtered, evaporated, to afford the desired product (2S,4R)-4-(biphenyl-4-yl)-1-((S)-2-(tert-butoxycarbonylamino)-3,3-dimethylbutanoyl)-4-(methylthio)pyrrolidine-2-carboxylic acid (136 mg, 0.232 mmol, 77% yield) as a white foam. LC-MS (retention time: 3.25 min, method B), MS m/z 527 (M+H).

Step 8

To an iced slurry of (2S,4R)-4-(biphenyl-4-yl)-1-((S)-2-(tert-butoxycarbonylamino)-3,3-dimethylbutanoyl)-4-(methylthio)pyrrolidine-2-carboxylic acid (26 mg, 0.049 mmol), (1R,2S)-1-amino-N-(cyclopropylsulfonyl)-2-vinylcyclopropanecarboxamide, p-toluenesulfonate salt, H$_2$O (24.85 mg, 0.059 mmol), and HATU (28.1 mg, 0.074 mmol) in DCM (1 mL) was added N,N-diisopropylethylamine (0.026 mL, 0.148 mmol). The formed colorless slurry was stirred at room temperature overnight (it became light yellow solution). Diluted with DCM, quenched with 5% citric acid. The separated organic layer was washed with sat. sodium citrate and brine, dried over MgSO$_4$, filtered, evaporated in vacuo. The residue was purified by prep-HPLC to afford the desired product tert-butyl (S)-1-((2S,4R)-4-(biphenyl-4-yl)-2-((1R,2S)-1-(cyclopropylsulfonylcarbamoyl)-2-vinylcyclopropylcarbamoyl)-4-(methylthio)pyrrolidin-1-yl)-3,3-dimethyl-1-oxobutan-2-ylcarbamate (18 mg, 0.024 mmol, 49.3% yield) as a white solid. $^1$H NMR (500 MHz, MeOD) δppm 1.03-1.12 (m, 11H), 1.25 (d, J=3.36 Hz, 2H), 1.43-1.48 (m, 1H), 1.50 (s, 9H), 1.88 (dd, J=8.09, 5.34 Hz, 1H), 1.92 (s, 3H), 2.16-2.27 (m, 1H), 2.38 (t, J=11.29 Hz, 1H), 2.82 (dd, J=11.90, 6.10 Hz, 1H), 2.90-2.99 (m, 1H), 3.97-4.04 (m, 2H), 4.48-4.53 (m, 1H), 5.03 (d, J=10.99 Hz, 1H), 5.13 (d, J=10.68 Hz, 1H), 5.30 (d, J=17.40 Hz, 1H), 5.70-5.81 (m, 1H), 7.37 (t, J=7.02 Hz, 1H), 7.46 (t, J=7.48 Hz, 2H), 7.57-7.64 (m, 4H), 7.64-7.73 (m, 2H). LC-MS (retention time: 3.28 min, method B), MS m/z 739 (M+H).

Example 9

Compound 9

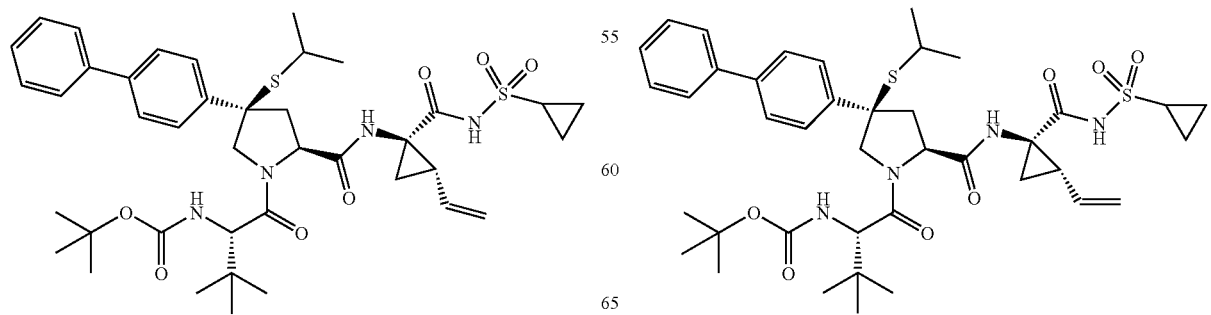

Compound 9

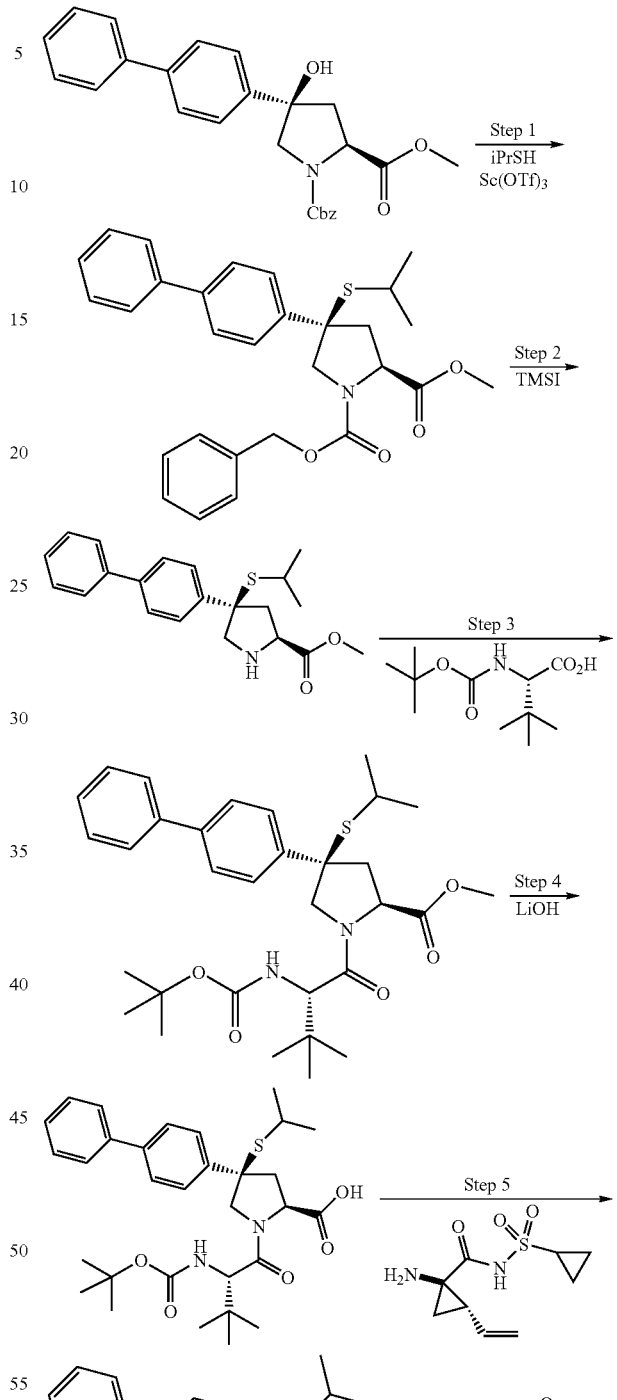

Scheme 6

Step 1

To a clear solution of (2S,4R)-1-benzyl 2-methyl 4-(biphenyl-4-yl)-4-hydroxypyrrolidine-1,2-dicarboxylate (1.82 g, 4.22 mmol) and 2-propanethiol (0.470 mL, 5.06 mmol) in acetonitrile (20 mL) was added Scandium(III) trifluoromethanesulfonate (0.208 g, 0.422 mmol) as solid by one portion at room temperature. The formed pink solution was stirred at this temperature for 26 h. TLC analysis showed starting material was completely consumed. Quenched with sat. ammonium chloride, extracted with EtOAc. Washed the organic with brine, dried over MgSO$_4$, filtered, evaporated in vacuo. The residue was purified by BIOTAGE® column, eluted with gradient 5~40% EtOAc-hexane to afford the mixture of diastereomers 1.44 g (70%). This oily mixture was purified by BIOTAGE® again, eluted with gradient 0~20% EtOAc-toluene to yield the by-product (2S,4S)-1-benzyl 2-methyl 4-(biphenyl-4-yl)-4-(isopropylthio)pyrrolidine-1,2-dicarboxylate (1.05 g, 1.930 mmol, 45.8% yield) as a white foam and the desired product (2S,4R)-1-benzyl 2-methyl 4-(biphenyl-4-yl)-4-(isopropylthio)pyrrolidine-1,2-dicarboxylate (450 mg, 0.827 mmol, 19.61% yield) as a white foam. $^1$H NMR (500 MHz, MeOD) δppm 0.96 (d, J=6.71 Hz, 1.5H, rotamer), 1.00 (d, J=6.71 Hz, 1.5H, rotamer), 1.07 (d, J=7.02 Hz, 3H), 2.48-2.57 (m, 1H), 2.57-2.68 (m, 1H), 2.97-3.07 (m, 1H), 3.65 (s, 1.5H, rotamer), 3.77 (s, 1.5H, rotamer), 3.82-3.91 (m, 1H), 4.26-4.42 (m, 2H), 5.00-5.28 (m, 2H), 7.25-7.72 (m, 14H). LC-MS (retention time: 3.39 min, method B), MS m/z 490 (M+H).

Step 2

To an iced solution of (2S,4R)-1-benzyl 2-methyl 4-(biphenyl-4-yl)-4-(isopropylthio)pyrrolidine-1,2-dicarboxylate (372 mg, 0.760 mmol) in acetonitrile (4 mL) was added iodotrimethylsilane (0.162 mL, 1.140 mmol). The formed light brown solution was stirred at room temperature for 2 h. Cooled with ice bath, quenched with MeOH. The final light brown solution was purified by prep-HPLC. The collected fractions were evaporated on speed-vac system to afford the desired product (2S,4R)-methyl 4-(biphenyl-4-yl)-4-(isopropylthio)pyrrolidine-2-carboxylate, TFA (259 mg, 0.496 mmol, 65.3% yield) as a brown foam. LC-MS (retention time: 2.52 min, method B), MS m/z 356 (M+H).

Step 3

To an iced slurry of (2S,4R)-methyl 4-(biphenyl-4-yl)-4-(isopropylthio)pyrrolidine-2-carboxylate, TFA (255 mg, 0.543 mmol), (S)-2-(tert-butoxycarbonylamino)-3,3-dimethylbutanoic acid (138 mg, 0.597 mmol), and HATU (309 mg, 0.814 mmol) in DCM (8 mL) was added N,N-diisopropylethylamine (0.285 mL, 1.629 mmol). The formed colorless slurry was stirred at room temperature overnight. Diluted with DCM, quenched with 5% citric acid. The organic layer was washed with 0.1 M NaOH and brine, dried over MgSO$_4$, filtered, evaporated in vacuo. The residue was purified by BIOTAGE® column, eluted with 5~35% EtOAc-hexane to yield the desired product (2S,4R)-methyl 4-(biphenyl-4-yl)-1-((S)-2-(tert-butoxycarbonylamino)-3,3-dimethylbutanoyl)-4-(isopropylthio)pyrrolidine-2-carboxylate (240 mg, 0.380 mmol, 69.9% yield) as a white foam. $^1$H NMR (500 MHz, MeOD) δppm 1.06 (d, 3H), 1.09-1.13 (m, 12H), 1.48 (s, 9H), 2.48 (dd, J=12.82, 8.24 Hz, 1H), 2.53-2.62 (m, 1H), 2.97 (dd, J=12.51, 7.63 Hz, 1H), 3.73 (s, 3H), 4.03 (d, J=11.29 Hz, 1H), 4.25 (t, J=7.93 Hz, 1H), 4.45 (s, 1H), 4.88-4.91 (m, 1H), 7.36 (t, J=7.32 Hz, 1H), 7.45 (t, J=7.78 Hz, 2H), 7.58-7.73 (m, 6H). LC-MS (retention time: 3.50 min, method B), MS m/z 569 (M+H).

Step 4

To a solution of (2S,4R)-methyl 4-(biphenyl-4-yl)-1-((S)-2-(tert-butoxycarbonylamino)-3,3-dimethylbutanoyl)-4-(isopropylthio)pyrrolidine-2-carboxylate (208 mg, 0.366 mmol) in THF (2 mL) and MeOH (2.000 mL) was added pre-made solution of Lithium hydroxide monohydrate (30.7 mg, 0.731 mmol) in water (2 mL). The resulting cloudy solution was stirred at room temperature overnight. Quenched with 5% citric acid, extracted with EtOAc. The organic layer was washed with brine, dried over MgSO$_4$, filtered, evaporated, to afford the desired product (2S,4R)-4-(biphenyl-4-yl)-1-((S)-2-(tert-butoxycarbonylamino)-3,3-dimethylbutanoyl)-4-(isopropylthio)pyrrolidine-2-carboxylic acid (202 mg, 0.328 mmol, 90% yield) as a white foam. LC-MS (retention time: 3.39 min, method B), MS m/z 555 (M+H).

Step 5

To an iced slurry of (2S,4R)-4-(biphenyl-4-yl)-1-((S)-2-(tert-butoxycarbonylamino)-3,3-dimethylbutanoyl)-4-(isopropylthio)pyrrolidine-2-carboxylic acid (28 mg, 0.050 mmol), (1R,2S)-1-amino-N-(cyclopropylsulfonyl)-2-vinylcyclopropanecarboxamide, pTSA, 0.68H$_2$O (23.03 mg, 0.056 mmol), and HATU (28.5 mg, 0.075 mmol) in DCM (1 mL) was added N,N-Diisopropylethylamine (0.035 mL, 0.202 mmol). The formed light brown solution was stirred at room temperature overnight. Diluted with EtOAc, washed it with 5% citric acid, and brine, dried over MgSO$_4$, filtered, evaporated. The formed residue was purified by prep-HPLC to afford the desired product tert-butyl (S)-1-((2S,4R)-4-(biphenyl-4-yl)-2-((1R,2S)-1-(cyclopropylsulfonylcarbamoyl)-2-vinylcyclopropylcarbamoyl)-4-(isopropylthio)pyrrolidin-1-yl)-3,3-dimethyl-1-oxobutan-2-ylcarbamate (23 mg, 59% yield) as a white solid. $^1$H NMR (500 MHz, MeOD) δppm 1.03-1.07 (m, 3H), 1.09-1.12 (m, 11H), 1.21-1.28 (m, 4H), 1.40-1.51 (m, 2H), 1.52 (s, 9H), 1.87 (dd, J=7.93, 5.49 Hz, 1H), 2.20 (q, J=8.85 Hz, 1H), 2.30 (t, J=11.60 Hz, 1H), 2.54-2.62 (m, 1H), 2.81 (dd, J=12.05, 6.26 Hz, 1H), 2.90-2.98 (m, 1H), 3.87 (dd, J=10.99, 6.41 Hz, 1H), 3.97 (d, J=0.99 Hz, 1H), 4.51 (d, J=9.77 Hz, 1H), 5.08-5.19 (m, 2H), 5.29 (d, J=17.09 Hz, 1H), 5.69-5.81 (m, 1H), 7.37 (t, J=7.32 Hz, 1H), 7.46 (t, J=7.78 Hz, 2H), 7.60 (dd, J=10.68, 7.93 Hz, 4H), 7.71 (d, J=8.55 Hz, 2H). LC-MS (retention time: 3.42 min, method B), MS m/z 767 (M+H).

Example 10

Compound 10

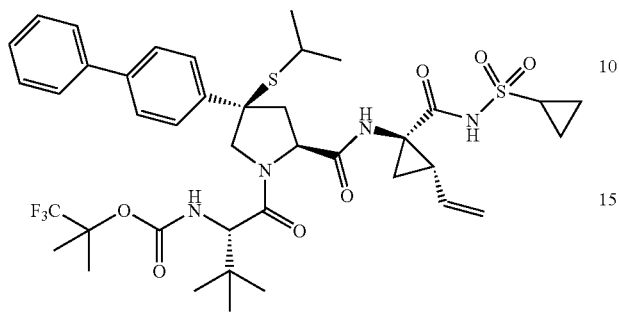

Compound 10

Scheme 7

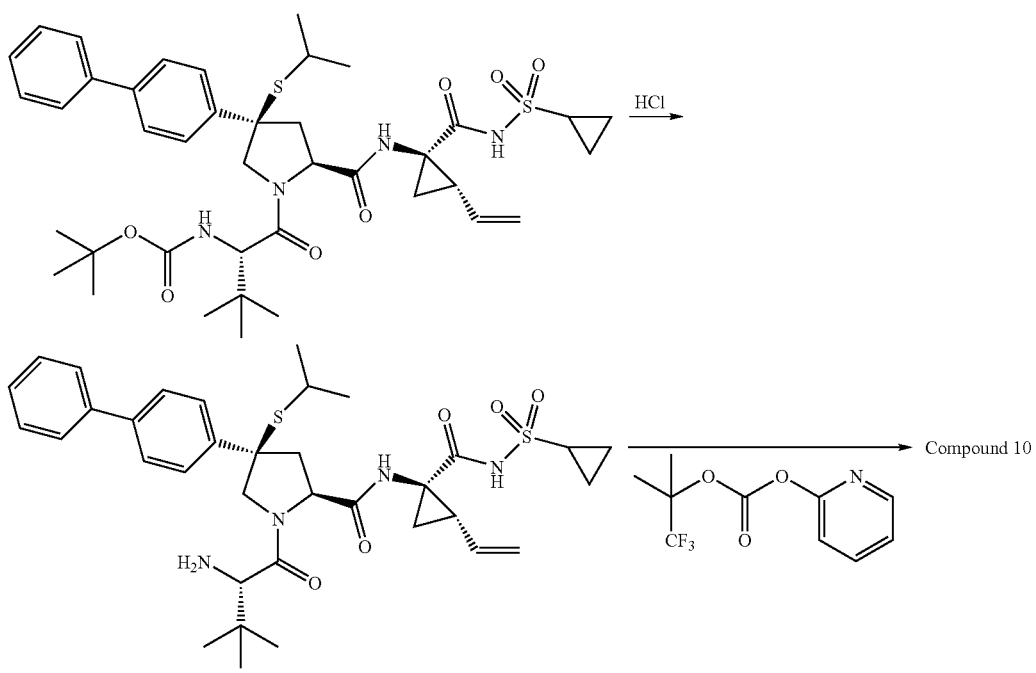

Step 1

4.0M HCl in dioxane (3.1 mL, 12.47 mmol) was added to tert-butyl (S)-1-((2S,4R)-4-(biphenyl-4-yl)-2-((1R,2S)-1-(cyclopropylsulfonylcarbamoyl)-2-vinylcyclopropylcarbamoyl)-4-(isopropylthio)pyrrolidin-1-yl)-3,3-dimethyl-1-oxobutan-2-ylcarbamate (155 mg, 0.202 mmol) and stirred at r.t. for 2 h. The reaction was concentrated and dried under vacuum to afford the desired product (2S,4R)-1-((S)-2-amino-3,3-dimethylbutanoyl)-4-(biphenyl-4-yl)-N-((1R,2S)-1-(cyclopropylsulfonylcarbamoyl)-2-vinylcyclopropyl)-4-(isopropylthio)pyrrolidine-2-carboxamide, HCl (141 mg, 0.180 mmol, 89% yield) as a light yellow powder. LC-MS (retention time: 2.77 min, method B), MS m/z 667 (M+H).

Step 2

To a slurry of (2S,4R)-1-((S)-2-amino-3,3-dimethylbutanoyl)-4-(biphenyl-4-yl)-N-((1R,2S)-1-(cyclopropylsulfonylcarbamoyl)-2-vinylcyclopropyl)-4-(isopropylthio)pyrrolidine-2-carboxamide, HCl (14 mg, 0.020 mmol) and pyridin-2-yl 1,1,1-trifluoro-2-methylpropan-2-yl carbonate (7.44 mg, 0.030 mmol) in THF (1 mL) at 0° C. was added N,N-diisopropylethylamine (0.014 mL, 0.080 mmol) dropwise. The formed light yellow solution was stirred at rt overnight. Diluted with EtOAc, washed with 5% citric acid and brine, dried over MgSO$_4$, filtered. The filtrate was concentrate in vacuo. The white residue was purified by prep-HPLC to yield the desired product 1,1,1-trifluoro-2-methylpropan-2-yl (S)-1-((2S,4R)-4-(biphenyl-4-yl)-2-((1R,2S)-1-(cyclopropylsulfonylcarbamoyl)-2-vinylcyclopropylcarbamoyl)-4-

(isopropylthio)pyrrolidin-1-yl)-3,3-dimethyl-1-oxobutan-2-ylcarbamate (11 mg, 0.013 mmol, 65.3% yield) as a white solid. $^1$H NMR (500 MHz, MeOD) δppm 0.99-1.15 (m, 13H) 1.15-1.34 (m, 6H) 1.36-1.50 (m, 1H) 1.72 (dd, J=12.36, 6.26 Hz, 5H) 1.80-1.94 (m, 1H) 2.15-2.23 (m, 1H) 2.26-2.38 (m, 1H) 2.49-2.63 (m, 1H) 2.86 (br. s., 1H) 2.93 (td, J=8.32, 4.12 Hz, 1H) 3.84-3.92 (m, 1H) 3.93-4.03 (m, 1H) 4.46-4.54 (m, 1H) 4.60 (d, J=6.41 Hz, 2H) 5.02-5.18 (m, 2H) 5.20-5.35 (m, 1H) 5.65-5.82 (m, 1H) 7.37 (t, J=7.32 Hz, 1H) 7.41-7.53 (m, 3H) 7.55-7.66 (m, 4H) 7.66-7.77 (m, 2H). LC-MS (retention time: 3.47 min, method B), MS m/z 821 (M+H).

Example 11

Compound 11

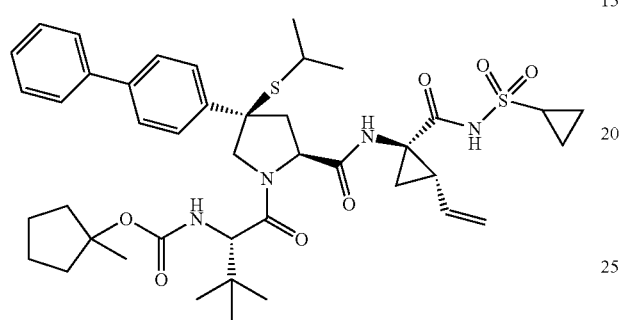

To a slurry of (2S,4R)-1-((S)-2-amino-3,3-dimethylbutanoyl)-4-(biphenyl-4-yl)-N-((1R,2S)-1-(cyclopropylsulfonylcarbamoyl)-2-vinylcyclopropyl)-4-(isopropylthio)pyrrolidine-2-carboxamide, HCl (14 mg, 0.020 mmol) and 1-methylcyclopentyl pyridin-2-yl carbonate (13.21 mg, 0.060 mmol) in THF (1 mL) at 0° C. was added N,N-diisopropylethylamine (0.017 mL, 0.100 mmol) dropwise. The formed light yellow solution was stirred at rt overnight. Diluted with EtOAc, washed with 5% citric acid and brine, dried over MgSO$_4$, filtered. The filtrate was concentrate in vacuo. The white residue was purified by prep-HPLC to yield the desired product 1-methylcyclopentyl (S)-1-((2S,4R)-4-(biphenyl-4-yl)-2-((1R,2S)-1-(cyclopropylsulfonylcarbamoyl)-2-vinylcyclopropylcarbamoyl)-4-(isopropylthio)pyrrolidin-1-yl)-3,3-dimethyl-1-oxobutan-2-ylcarbamate (8.5 mg, 10.40 μmol, 52.2% yield) as a white solid. $^1$H NMR (500 MHz, MeOD) δppm 0.98-1.17 (m, 14H) 1.24 (t, J=6.10 Hz, 5H) 1.44 (dd, J=9.46, 5.19 Hz, 1H) 1.58-1.83 (m, 9H) 1.88 (dd, J=7.93, 5.49 Hz, 1H) 2.06-2.39 (m, 4H) 2.54-2.66 (m, 1H) 2.82 (dd, J=11.75, 5.95 Hz, 1H) 2.89-3.01 (m, 1H) 3.80-3.94 (m, 1H) 3.92-4.04 (m, 1H) 4.47-4.58 (m, 1H) 4.58-4.66 (m, 1H) 5.13 (d, J=10.07 Hz, 2H) 5.23-5.37 (m, 1H) 5.75 (dt, J=17.17, 9.58 Hz, 1H) 6.90-7.03 (m, 1H) 7.33-7.43 (m, 1H) 7.46 (t, J=7.63 Hz, 2H) 7.56-7.68 (m, 4H) 7.71 (d, J=8.55 Hz, 2H).

Example 12

Compound 12

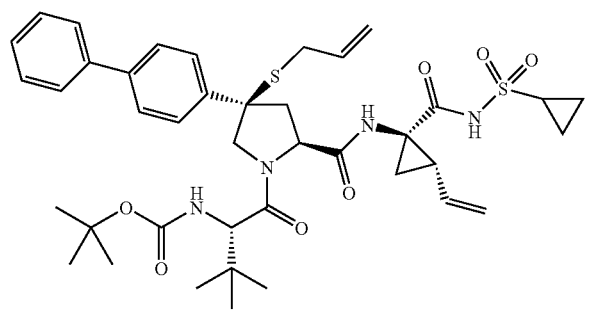

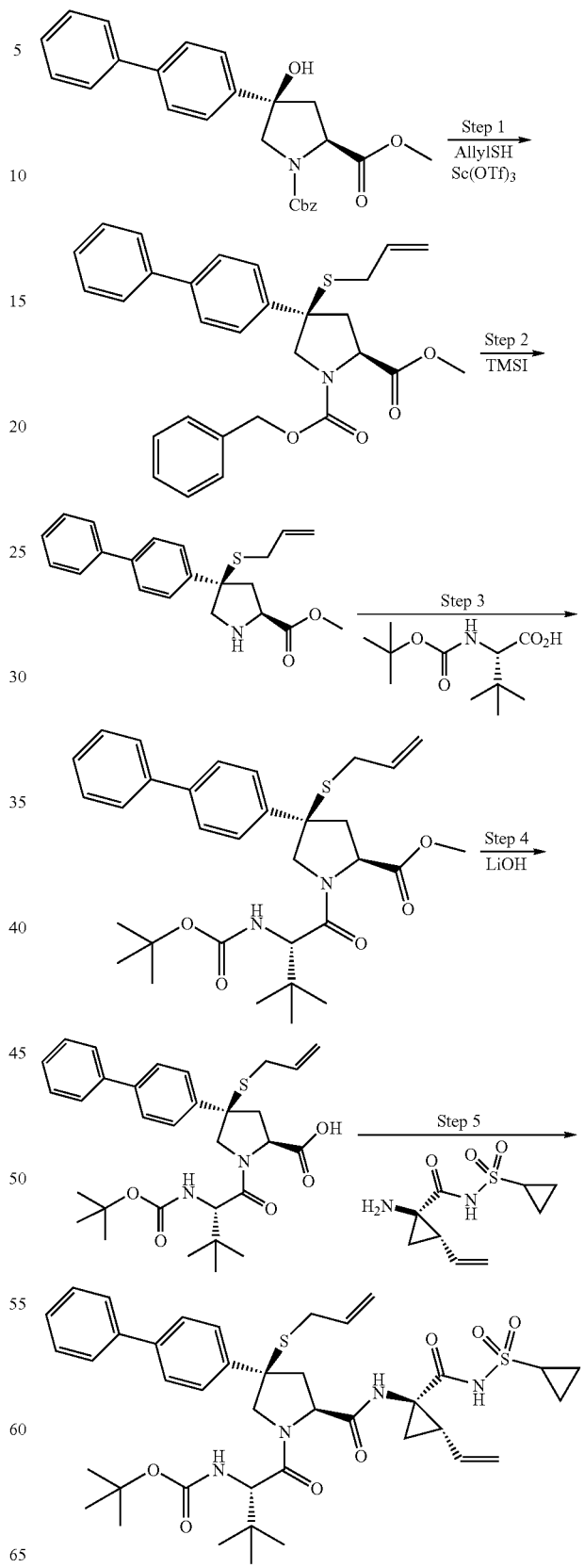

Scheme 8

Step 1

To a clear solution of (2S,4R)-1-benzyl 2-methyl 4-(biphenyl-4-yl)-4-hydroxypyrrolidine-1,2-dicarboxylate (6.48 g, 15.02 mmol) and prop-2-ene-1-thiol (3.18 g, 30.0 mmol) in acetonitrile (70 mL) was added Scandium(III) trifluoromethanesulfonate (0.739 g, 1.502 mmol) as solid by one portion at room temperature. The formed pink solution was stirred at this temperature for 20 h. LC/MS and TLC analysis showed starting material was completely consumed and the desired product was formed. Quenched with sat. ammonium chloride, extracted with EtOAc. Washed the organic with brine, dried over $MgSO_4$, filtered, evaporated in vacuo. The residue was purified by BIOTAGE® column, eluted with 5%~50% EtOAc-hexane to afford mixture and diastereomers (2.88 g, 79%) and starting material (0.600 g, 18%). This mixture was purified by BIOTAGE® column again, eluted with 2%~8% EtOAc-Toluene to afford the desired product (2S,4R)-1-benzyl 2-methyl 4-(allylthio)-4-(biphenyl-4-yl)pyrrolidine-1,2-dicarboxylate (1.85 g, 3.41 mmol, 22.74% yield) as an viscous oil and the undesired diastereomer plus some overlapped fraction (1.80 g) as an viscous oil. $^1$H NMR (500 MHz, CHLOROFORM-d) δ ppm 2.59-2.75 (m, 1H) 2.77-2.94 (m, 3H) 3.55, 3.80 (s, 3H) 3.92 (d, J=11.60 Hz, 1H) 4.19-4.31 (m, 1H) 4.35-4.50 (m, 1H) 4.89-5.07 (m, 3H) 5.09-5.25 (m, 2H) 5.51-5.76 (m, 1H) 5.63 (ddd, J=17.01, 9.69, 7.17 Hz, 1H) 7.22-7.41 (m, 7H) 7.40-7.49 (m, 3H) 7.48-7.66 (m, 12H) 7.49-7.66 (m, 4H). LC-MS (retention time: 3.32 min, method A), MS m/z 488 (M+H).

Step 2

To an iced solution of (2S,4R)-1-benzyl 2-methyl 4-(allylthio)-4-(biphenyl-4-yl)pyrrolidine-1,2-dicarboxylate (1.85 g, 3.79 mmol) in acetonitrile (20 mL) was added iodotrimethylsilane (0.810 mL, 5.69 mmol). The formed light brown solution was stirred at room temperature for 2 h. Cooled with ice bath, quenched with methyl alcohol (7.68 mL, 190 mmol). The formed light brown solution was purified by prep-HPL, and the collected fractions were evaporated on speed-vac system. The yellow residue was taken up in DCM, washed with sat. $Na_2CO_3$ and brine, dried over $MgSO_4$, filtered, evaporated in vacuo to afford the desired product (2S,4R)-methyl 4-(allylthio)-4-(biphenyl-4-yl)pyrrolidine-2-carboxylate (664 mg, 1.878 mmol, 49.5% yield) as a viscous oil. $^1$H NMR (500 MHz, MeOD) δ ppm 2.93-3.08 (m, 3H) 3.11-3.20 (m, 1H) 3.77-3.88 (m, 1H) 3.92-3.99 (m, 3H) 4.04 (d, J=12.21 Hz, 1H) 4.72-4.80 (m, 1H) 5.02 (d, J=9.77 Hz, 1H) 5.09 (dd, J=16.94, 1.37 Hz, 1H) 5.54-5.70 (m, 1H) 7.35-7.42 (m, 1H) 7.43-7.56 (m, 4H) 7.60-7.68 (m, 2H) 7.69-7.77 (m, 2H). LC-MS (retention time: 2.21 min, method A), MS m/z 354 (M+H).

Step 3

To a slurry of (2S,4R)-methyl 4-(allylthio)-4-biphenyl-4-yl)pyrrolidine-2-carboxylate (355 mg, 1.004 mmol), (S)-2-(tert-butoxycarbonylamino)-3,3-dimethylbutanoic acid (256 mg, 1.105 mmol), and HATU (573 mg, 1.506 mmol) in DCM (10 mL) was added N,N-diisopropylethylamine (0.526 mL, 3.01 mmol). The formed solution was stirred at room temperature overnight. Washed with 1M HCl, 1M NaOH, and brine, dried over $MgSO_4$, filtered, evaporated. The residue was purified by BIOTAGE® column, eluted with gradient 5%~50% acetone-hexane to afford the desired product (2S,4R)-methyl 4-(allylthio)-4-(biphenyl-4-yl)-1-((S)-2-(tert-butoxycarbonylamino)-3,3-dimethylbutanoyl)pyrrolidine-2-carboxylate (416 mg, 0.661 mmol, 65.8% yield) as a white foam. $^1$H NMR (500 MHz, MeOD)) δppm 1.10 (s, 8H) 1.41-1.54 (m, 9H) 2.54 (dd, J=12.80, 7.78 Hz, 1H) 2.85-3.02 (m, 3H) 3.63-3.80 (m, 3H) 4.00-4.13 (m, 1H) 4.30 (t, J=7.65 Hz, 1H) 4.37-4.49 (m, 1H) 4.92-5.14 (m, 2H) 5.63-5.79 (m, 1H) 7.30-7.39 (m, 1H) 7.44 (t, J=7.53 Hz, 2H) 7.56-7.70 (m, 6H). LC-MS (retention time: 3.09 min, method B), MS m/z 567 (M+H).

Step 4

To a solution of (2S,4R)-methyl 4-(allylthio)-4-(biphenyl-4-yl)-1-((S)-2-(tert-butoxycarbonylamino)-3,3-dimethylbutanoyl)pyrrolidine-2-carboxylate (362 mg, 0.639 mmol) in THF (5 mL) and MeOH (5.00 mL) was added pre-made solution of lithium hydroxide hydrate (80 mg, 1.916 mmol) in Water (5 mL). The resulting cloudy solution was stirred at room for 24 h. Quenched with 5% citric acid, extracted with EtOAc. The organic layer was washed with brine, dried over $MgSO_4$, filtered, evaporated, to afford the desired product (2S,4R)-4-(allylthio)-4-(biphenyl-4-yl)-1-((S)-2-(tert-butoxycarbonylamino)-3,3-dimethylbutanoyl)pyrrolidine-2-carboxylic acid (312 mg, 0.553 mmol, 87% yield) as a white solid. LC-MS (retention time: 2.96 min, method B), MS m/z 553 (M+H).

Step 5

To a slurry of (2S,4R)-4-(allylthio)-4-(biphenyl-4-yl)-1-((S)-2-(tert-butoxycarbonylamino)-3,3-dimethylbutanoyl)pyrrolidine-2-carboxylic acid (16 mg, 0.029 mmol), (1R,2S)-1-amino-N-(cyclopropylsulfonyl)-2-vinylcyclopropanecarboxamide, pTSA, $0.68H_2O$ (15.01 mg, 0.036 mmol), and HATU (16.51 mg, 0.043 mmol) in DCM (1 mL) was added N,N-diisopropylethylamine (0.025 mL, 0.145 mmol). The formed solution was stirred at room temperature overnight. Diluted with DCM, washed with 1M HCl and brine, dried over $MgSO_4$, filtered, evaporated. The residue was purified by BIOTAGE® column, eluted with gradient 5%~50% acetone-hexane to afford the desired product tert-butyl (S)-1-((2S,4R)-4-(allylthio)-4-(biphenyl-4-yl)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylcarbamate (13 mg, 0.016 mmol, 55.2% yield) as a white foam. $^1$H NMR (500 MHz, MeOD) δppm 0.99-1.15 (m, 10H) 1.24 (d, J=4.52 Hz, 2H) 1.42 (dd, J=9.41, 5.40 Hz, 1H) 1.49 (s, 9H) 1.86 (dd, J=8.03, 5.52 Hz, 1H) 2.19 (q, J=8.78 Hz, 1H) 2.34 (t, J=41.54 Hz, 1H) 2.81 (dd, J=12.17, 6.40 Hz, 1H) 2.87-3.07 (m, 3H) 3.89 (dd, J=10.54, 6.27 Hz, 1H) 3.97 (d, J=11.04 Hz, 1H) 4.48 (d, J=9.79 Hz, 1H) 4.97-5.15 (m, 4H) 5.27 (d, J=17.07 Hz, 1H) 5.64-5.88 (m, 2H) 6.75 (d, J=9.79 Hz, 1H) 7.30-7.40 (m, 1H) 7.45 (t, J=7.53 Hz, 2H) 7.54-7.63 (m, 4H) 7.64-7.74 (m, 2H). LC-MS (retention time: 3.00 mm, method B), MS m/z 765 (M+H).

LC/MS conditions for Method A:
Start % B 0
Final % B=100
Gradient Time=3 min
Stop Time=4 min
Flow Rate=4 ml/min
Wavelength=220
Solvent A=90% Water-10% Methanol-0.1% TFA
Solvent B=10% Water-90% Methanol-0.1% TFA
Column 3=(3) PHENOMENEX®-LUNA 4.6×50 nm S10
LC/MS conditions for Method B:
Start % B=30
Final % B=100

Gradient Time=3 min
Stop Time=4 min
Flow Rate=4 ml/min
Wavelength=220
Solvent A=90% Water-10% Methanol-0.1% TFA
Solvent B=10% Water 90% Methanol-0.1% TEA
Column 3=(3) PHENOMENEX®-LUNA 4.6×50 mm S10

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS13 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See Simmonds, P. et al., *J. Clin. Microbiol.*, 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in GEN-BANK® (AAB67036, see Yanagi, M. et al., *Proc. Natl. Acad. Sci. U.S.A.*, 94(16):8738-8743 (1997); AF054247, see Yanagi, M. et al., *Virology*, 244(1):161-172 (1998)).

The H77 and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari, P. et al, *Biochemistry*, 38(17):5620-5632 (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari, P. et al., *J. Virol.*, 72(8):6758-6769 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-hydroxyethyl)piperazine-N'-(2-ethane sulfonic acid) (HEPES), pH 7.5, 20% glycerol, 500 mM sodium chloride (NaCl), 0.5% Triton X-100, 1 microgram/milliliter ("µg/mL") lysozyme, 5 mM magnesium chloride ($MgCl_2$), 1 µg/ml DnaseI, 5 mM β-mercaptoethanol (βME), protease inhibitor-ethylenediamine tetraacetic acid (EDTA) free (Roche), homogenized and incubated for 20 minutes (min) at 4° C. The homogenate was sonicated and clarified by ultra-centrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991) (FRET peptide), described by Taliani et al. in *Anal. Biochem.*, 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a CYTOFLUOR® Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from BioRad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the CYTOFLUOR® Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100 - [(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+((B-A)/(1+((C/x)^D)))$.

All of the compounds tested were found to inhibit the activity of the NS3/4A protease complex with $IC_{50}$'s of 73 nM or less. Further, compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using a fluorometric Amino-Methyl-Coumarin (AMC) substrate specific for each enzyme was used as described previously (PCT Patent Application No. WO 00/09543) with some modifications to the serine protease assays. All enzymes were purchased from Sigma, EMDbiosciences while the substrates were from Bachem, Sigma and EMDbiosciences.

Compound concentrations varied from 100 to 0.4 µM depending on their potency. The enzyme assays were each initiated by addition of substrate to enzyme-inhibitor pre-incubated for 10 min at room temperature and hydrolysis to 15% conversion as measured on CYTOFLUOR®.

The final conditions for each assay were as follows:
50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with 5 µM LLVY-AMC and 1 nM Chymotrypsin.
50 mM Tris-HCl, pH 8.0, 50 mM NaCl, 0.1 mM DETA, 3% DMSO, 0.02% Tween-20, 5 µM succ-AAPV-AMC and 20 nM HNE or 8 nM PPE;
100 mM NaOAC (Sodium Acetate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 µM Z-FR-AMC diluted in $H_2O$.

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration ($IC_{50}$) was calculated by the use of Excel XLfit software.

Generation of HCV Replicon

An HCV replicon whole cell system was established as described by Lohmann, V. et al., Science, 285(5424):110-113 (1999). This system enabled us to evaluate the effects of our HCV Protease compounds on HCV RNA replication. Briefly, using the HCV strain 1b sequence described in the Lohmann paper (Accession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomysin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnostic Systems) for a $CC_{50}$ reading. The toxicity of compound ($CC_{50}$) was determined by adding $1/10^{th}$ volume of alamar Blue to the media incubating the cells. After 4 h, the fluorescence signal from each well was read, with an excitation wavelength at 530 nm and an emission wavelength of 580 nm, using the CYTOFLUOR® Series 4000 (Perspective Biosystems). Plates were then rinsed thoroughly with Phosphate-Buffered Saline (PBS) (3 times 150 µl). The cells were lysed with 25 µl of a lysis assay reagent containing an HCV protease substrate (5× cell Luciferase cell culture lysis reagent (PROMEGA® #E153A) diluted to 1× with distilled water, NaCl added to 150 mM final, the FRET peptide substrate (as described for the enzyme assay above) diluted to 10 µM final from a 2 mM stock in 100% DMSO. The plate was then placed into the CYTOFLUOR® 4000 instrument which had been set to 340 nm excitation/490 nm emission, automatic mode for 21 cycles and the plate read in a kinetic mode. $EC_{50}$ determinations were carried out as described for the $IC_{50}$ determinations.

HCV Replicon Luciferase Reporter Assay

As a secondary assay, $EC_{50}$ determinations from the replicon FRET assay were confirmed in a replicon luciferase reporter assay. Utilization of a replicon luciferase reporter assay was first described by Krieger et al (Krieger, N. et al., *J. Virol.*, 75(10):4614-4624 (2001)). The replicon construct described for our FRET assay was modified by inserting cDNA encoding a humanized form of the *Renilla* luciferase gene and a linker sequence fused directly to the 3'-end of the luciferase gene. This insert was introduced into the replicon construct using an Asc1 restriction site located in core, directly upstream of the neomycin marker gene. The adaptive mutation at position 1179 (serine to isoleucine) was also introduced (Blight, K. J. et al., *Science*, 290(5498):1972-1974). A stable cell line constitutively expressing this HCV replicon construct was generated as described above. The luciferase reporter assay was set up as described for the HCV replicon FRET assay with the following modifications. Following 4 days in a 37° C./5% $CO_2$ incubator, cells were analyzed for *Renilla* Luciferase activity using the Promega DUAL-GLO® Luciferase Assay System. Media (100 µl) was removed from each well containing cells. To the remaining 50 µl of media, 50 µl of DUAL-GLO® Luciferase Reagent was added, and plates rocked for 10 min to 2 h at room temperature. DUAL-GLO® Stop & Glo Reagent (50 µl) was then added to each well, and plates were rocked again for an additional 10 min to 2 h at room temperature. Plates were read on a Packard TOPCOUNT® NXT using a luminescence program.

The percentage inhibition was calculated using the formula below:

$$\% \text{ control} = \frac{\text{average luciferase signal in experimental wells (+ compound)}}{\text{average luciferase signal in } DMSO \text{ control wells (- compound)}}$$

The values were graphed and analyzed using XLfit to obtain the $EC_{50}$ value.

Representative compounds of the disclosure were assessed in the HCV enzyme assays, HCV replicon cell assay and/or in several of the outlined specificity assays. For example, Compound 1 was found to have an $IC_{50}$ of 4.6 nanomolar (nM) against the NS3/4A BMS strain in the enzyme assay. Similar potency values were obtained with the published H77 ($IC_{50}$ of 1.7 nM) and J4L6S ($IC_{50}$ of 1.1 nM) strains. The $EC_{50}$ value in the replicon FRET assay was 7.3 nM and 6.0 nM in the replicon Luciferase assay.

In the specificity assays, the same compound was found to have the following activity: HLE>12.1 µM; PPE>25 µM; Chymotrypsin=13.2 µM; Cathepsin B 7.5 µM. These results indicate this family of compounds is highly specific for the NS3 protease and many of these members inhibit HCV replicon replication.

The compounds of the current disclosure were tested and found to have activities as follows:

$IC_{50}$ Activity Range (NS3/4A BMS Strain): A is >0.2 µM; B is 0.02-0.2 µM; C is 1-20 nM.

$EC_{50}$ Activity Ranges (for compounds tested): A is >1 µM; B is 0.1-1 µM; C is 6-100 nM.

TABLE 2

| Example Number | IC50 | EC50 |
|---|---|---|
| 1 | 3.0 nM | 7.2-22 nM |
| 2 | C | C |
| 3 | 1.0 nM | 6.6 nM |
| 4 | C | C |
| 5 | C | C |
| 6 | 2.0 nM | 18-36 nM |
| 7 | C | C |
| 8 | C | C |
| 9 | C | C |
| 10 | C | C |
| 11 | C | C |
| 12 | C | C |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound of formula (I)

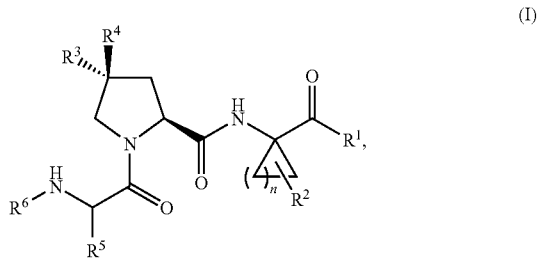

or a pharmaceutically acceptable salt thereof, wherein
n is 1, 2, or 3;
$R^1$ is selected from hydroxy and —$NHSO_2R^7$;
$R^2$ is selected from hydrogen, alkenyl, alkyl, and cycloalkyl; wherein the alkenyl, the alkyl, and the cycloalkyl are optionally substituted with one, two, three, or four halo groups;
$R^3$ is selected from alkenyl, alkyl, aryl, arylalkyl, cycloalkyl, (cycloalkyl)alkyl, heterocyclyl, and heterocyclylalkyl;
$R^4$ is selected from —S—$R^8$, —S(O)—$R^8$, and —S(O)$_2$—$R^8$;
$R^5$ is selected from hydrogen, alkenyl, alkoxyalkyl, alkoxycarbonylalkyl, alkyl, arylalkyl, carboxyalkyl, cyanoalkyl, cycloalkyl, (cycloalkyl)alkyl, haloalkoxyalkyl, haloalkyl, hydroxyalkyl, (NR$^a$R$^b$)alkyl, and NR$^a$R$^b$)carbonylalkyl;

R$^6$ is selected from hydrogen, alkoxycarbonyl, alkyl, alkylcarbonyl, alkylsulfonyl, cycloalkyloxycarbonyl, cycloalkyl, haloalkoxycarbonyl, haloalkyl, haloalkylcarbonyl, (R$^a$R$^b$)carbonyl, and (NR$^a$R$^b$)sulfonyl; or R$^6$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substituents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, NR$^g$R$^h$, (NR$^j$R$^k$)carbonyl, (NR$^j$R$^k$)sulfonyl, and oxo;

R$^7$ is selected from alkyl, aryl, cycloalkyl, (cycloalkyl)alkyl, heterocyclyl, and —NR$^c$R$^d$; wherein the cycloalkyl is optionally substituted with one group selected from alkyl, halo, and haloalkyl;

R$^8$ is selected from alkoxyalkyl, alkyl, arylalkyl, cycloalkyl, (cycloalkyl)alkyl, haloalkoxyalkyl, and haloalkyl;

R$^a$ and R$^b$ are independently selected from hydrogen, alkoxy, alkoxyalkyl, alkyl, aryl, arylalkyl, cycloalkyl, haloalkoxyalkyl, haloalkyl, heterocyclyl, and heterocyclylalkyl;

R$^c$ and R$^d$ are independently selected from alkoxy, alkyl, aryl, arylalkyl, cycloalkyl, (cycloalkyl)alkyl, heterocyclyl, and heterocyclylalkyl; or R$^c$ and R$^d$ together with the nitrogen atom to which they are attached form a five or six-membered monocyclic heterocyclic ring;

R$^g$ and R$^h$ are independently selected from hydrogen, alkoxyalkyl, alkoxycarbonyl, alkyl, alkylcarbonyl, arylalkyl, and haloalkyl; and R$^j$ and R$^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

2. A compound of claim 1 wherein R$^1$ is —NHSO$_2$R$^7$.

3. A compound of claim 2, or a pharmaceutically acceptable salt thereof, wherein n is 1;

R$^2$ is selected from alkenyl, alkyl, and cycloalkyl; wherein the alkenyl, the alkyl, and the cycloalkyl are optionally substituted with one, two, three, or four halo groups;

R$^3$ is selected from alkenyl, alkyl, aryl, arylalkyl, cycloalkyl, (cycloalkyl)alkyl, heterocyclyl, and heterocyclylalkyl;

R$^4$ is selected from —S—R$^8$, —S(O)—R$^8$, and —S(O)$_2$—R$^8$;

R$^5$ is selected from alkenyl, alkyl, and arylalkyl;

R$^6$ is selected from alkoxycarbonyl, cycloalkyloxycarbonyl, haloalkoxycarbonyl, (NR$^a$R$^b$)carbonyl;

R$^7$ is unsubstituted cycloalkyl; and

R$^8$ is alkyl.

4. A compound of claim 3, or a pharmaceutically acceptable salt thereof, wherein R$^5$ is alkyl.

5. A compound of claim 4, or a pharmaceutically acceptable salt thereof, wherein R$^3$ is aryl.

6. A compound selected from

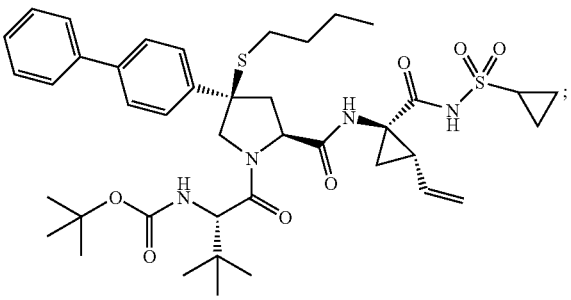

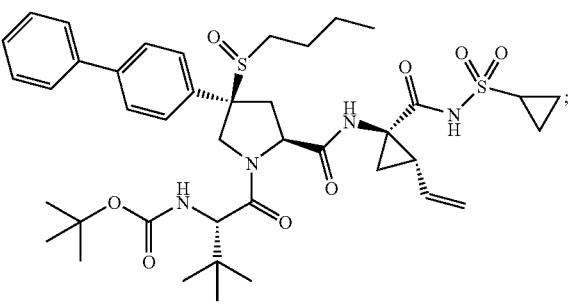

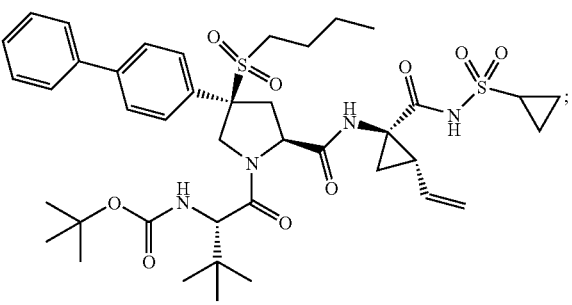

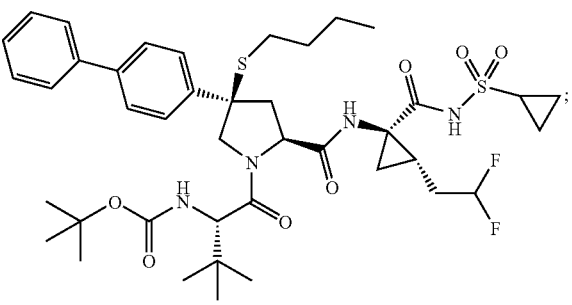

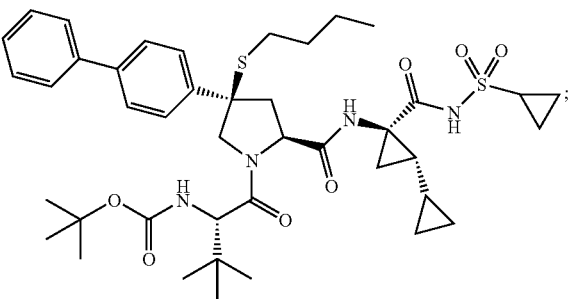

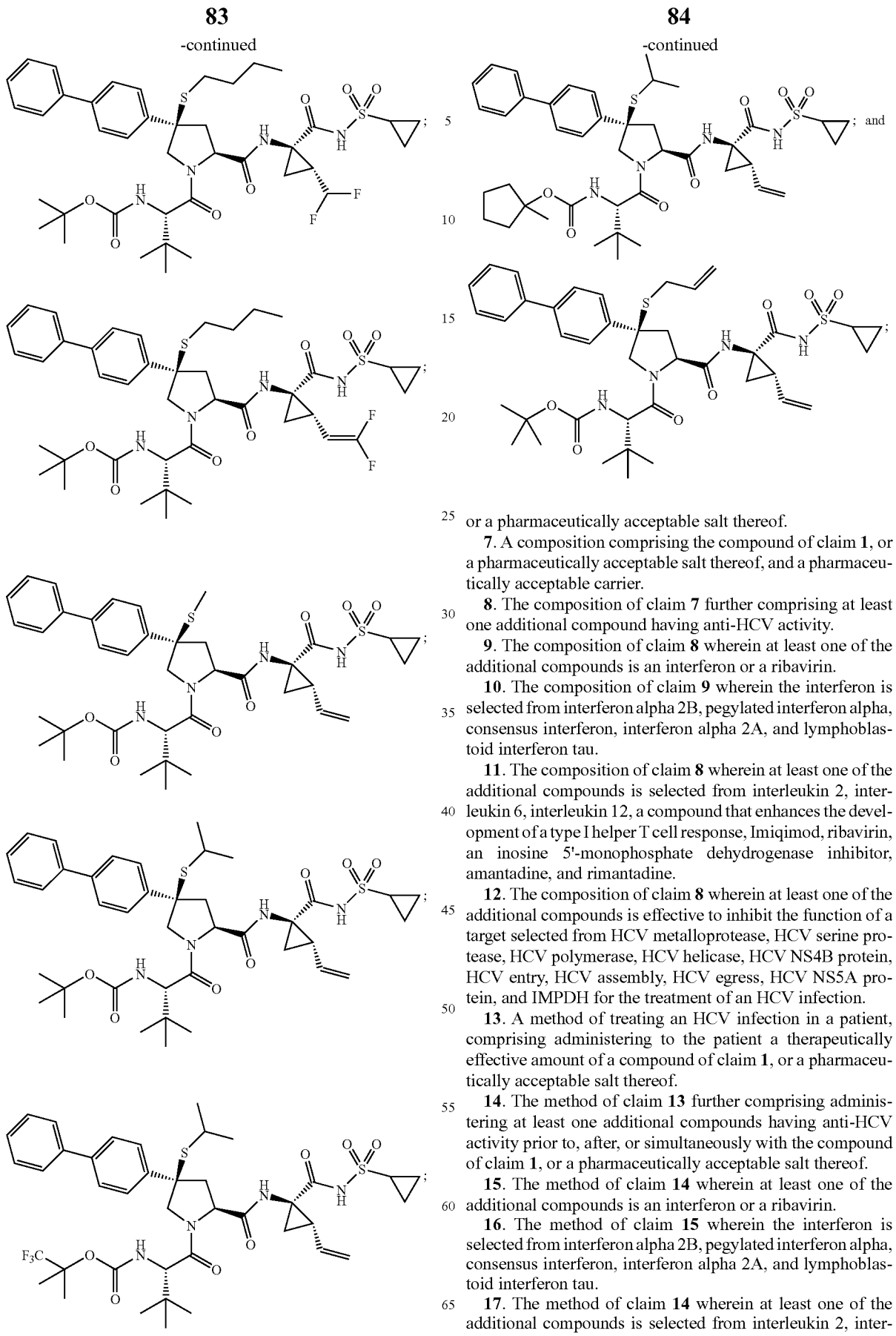

or a pharmaceutically acceptable salt thereof.

7. A composition comprising the compound of claim 1, or a pharmaceutically acceptable salt thereof, and a pharmaceutically acceptable carrier.

8. The composition of claim 7 further comprising at least one additional compound having anti-HCV activity.

9. The composition of claim 8 wherein at least one of the additional compounds is an interferon or a ribavirin.

10. The composition of claim 9 wherein the interferon is selected from interferon alpha 2B, pegylated interferon alpha, consensus interferon, interferon alpha 2A, and lymphoblastoid interferon tau.

11. The composition of claim 8 wherein at least one of the additional compounds is selected from interleukin 2, interleukin 6, interleukin 12, a compound that enhances the development of a type I helper T cell response, Imiqimod, ribavirin, an inosine 5'-monophosphate dehydrogenase inhibitor, amantadine, and rimantadine.

12. The composition of claim 8 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

13. A method of treating an HCV infection in a patient, comprising administering to the patient a therapeutically effective amount of a compound of claim 1, or a pharmaceutically acceptable salt thereof.

14. The method of claim 13 further comprising administering at least one additional compounds having anti-HCV activity prior to, after, or simultaneously with the compound of claim 1, or a pharmaceutically acceptable salt thereof.

15. The method of claim 14 wherein at least one of the additional compounds is an interferon or a ribavirin.

16. The method of claim 15 wherein the interferon is selected from interferon alpha 2B, pegylated interferon alpha, consensus interferon, interferon alpha 2A, and lymphoblastoid interferon tau.

17. The method of claim 14 wherein at least one of the additional compounds is selected from interleukin 2, interleukin 6, interleukin 12, a compound that enhances the development of a type 1 helper T cell response, Imiqimod, ribavirin, an inosine 5'-monophosphate dehydrogenase inhibitor, amantadine, and rimantadine.

18. The method of claim 14 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO. : 7,964,560 B2
APPLICATION NO. : 12/473188
DATED : June 21, 2011
INVENTOR(S) : Alan Xiangdong Wang et al.

It is certified that error appears in the above-identified patent and that said Letters Patent is hereby corrected as shown below:

In the Specification:

Column 4, line 18, change "Imiqimod" to -- Imiquimod --.

Column 4, line 57, change "Imiqimod" to -- Imiquimod --.

In the Claims:

Claim 1:

Column 81, line 7, change "$(R^aR^b)$carbonyl" to -- $(NR^aR^b)$carbonyl --.

Column 81, line 17, change "$NR^gR^h$" to -- $—NR^gR^h$ --.

Claim 11:

Column 84, line 41, change "type I" to -- type 1 --.

Column 84, line 41, change "Imiqimod" to -- Imiquimod --.

Claim 17:

Column 85, line 1, change "Imiqimod" to -- Imiquimod --.

Signed and Sealed this
Seventh Day of February, 2012

David J. Kappos
*Director of the United States Patent and Trademark Office*